US012577297B2

(12) United States Patent
Garidel et al.

(10) Patent No.: US 12,577,297 B2
(45) Date of Patent: Mar. 17, 2026

(54) ANTI-IL-23p19 ANTIBODY FORMULATIONS

(71) Applicant: Boehringer Ingelheim International GmbH, Ingelheim am Rhein (DE)

(72) Inventors: Patrick Garidel, Biberach an der Riss (DE); Torsten Schultz-Fademrecht, Aepfingen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 537 days.

(21) Appl. No.: 17/014,399

(22) Filed: Sep. 8, 2020

(65) Prior Publication Data

US 2021/0070852 A1      Mar. 11, 2021

Related U.S. Application Data

(60) Provisional application No. 62/897,930, filed on Sep. 9, 2019.

(51) Int. Cl.
| | |
|---|---|
| *C07K 16/24* | (2006.01) |
| *A61K 9/00* | (2006.01) |
| *A61K 9/08* | (2006.01) |
| *A61K 39/00* | (2006.01) |
| *A61K 39/395* | (2006.01) |
| *A61K 47/12* | (2006.01) |
| *A61K 47/26* | (2006.01) |

(52) U.S. Cl.
CPC .......... *C07K 16/244* (2013.01); *A61K 9/0019* (2013.01); *A61K 9/08* (2013.01); *A61K 39/3955* (2013.01); *A61K 47/12* (2013.01); *A61K 47/26* (2013.01); *A61K 2039/505* (2013.01); *A61K 2039/54* (2013.01); *C07K 2317/24* (2013.01); *C07K 2317/51* (2013.01); *C07K 2317/515* (2013.01); *C07K 2317/94* (2013.01)

(58) Field of Classification Search
CPC .............. C07K 16/244; C07K 2317/24; C07K 2317/515; C07K 2317/94; A61K 9/0019; A61K 9/08; A61K 39/3955
See application file for complete search history.

(56) References Cited

U.S. PATENT DOCUMENTS

| | | | |
|---|---|---|---|
| 4,179,337 | A | 12/1979 | Davis et al. |
| 4,275,149 | A | 6/1981 | Litman et al. |
| 4,301,144 | A | 11/1981 | Iwashita et al. |
| 4,318,980 | A | 3/1982 | Boguslaski et al. |
| 4,419,446 | A | 12/1983 | Howley et al. |
| 4,485,045 | A | 11/1984 | Rogen |
| 4,496,689 | A | 1/1985 | Mitra |
| 4,544,545 | A | 10/1985 | Ryan et al. |
| 4,560,655 | A | 12/1985 | Baker |
| 4,601,978 | A | 7/1986 | Karin |
| 4,640,835 | A | 2/1987 | Shimizu et al. |
| 4,657,866 | A | 4/1987 | Kumar |
| 4,670,417 | A | 6/1987 | Iwasaki et al. |
| 4,737,456 | A | 4/1988 | Weng et al. |
| 4,741,900 | A | 5/1988 | Alvarez et al. |
| 4,767,704 | A | 8/1988 | Cleveland et al. |
| 4,791,192 | A | 12/1988 | Nakagawa et al. |
| 4,816,567 | A | 3/1989 | Cabilly et al. |
| 4,927,762 | A | 5/1990 | Darfler |
| 4,965,199 | A | 10/1990 | Capon et al. |
| 4,975,278 | A | 12/1990 | Senter et al. |
| 5,013,556 | A | 5/1991 | Woodle et al. |
| 5,122,469 | A | 6/1992 | Mather et al. |
| 5,888,809 | A | 3/1999 | Allison |
| 6,037,454 | A | 3/2000 | Jardieu et al. |
| 6,054,297 | A | 4/2000 | Carter et al. |
| 6,060,284 | A | 5/2000 | Bazan |
| 6,407,213 | B1 | 6/2002 | Carter et al. |
| 6,479,634 | B1 | 11/2002 | Bazan |
| 6,495,667 | B1 | 12/2002 | Bazan |
| 6,610,285 | B1 | 8/2003 | Hirata |
| 6,756,481 | B2 | 6/2004 | Chirica et al. |
| 6,835,825 | B1 | 12/2004 | Bazan |
| 7,090,847 | B1 | 8/2006 | Oppmann et al. |
| 7,183,382 | B2 | 2/2007 | Oppmann et al. |
| 7,252,967 | B2 | 8/2007 | Hirata |
| 7,282,204 | B2 | 10/2007 | Oft et al. |
| 7,332,156 | B2 | 2/2008 | Bowman et al. |
| 7,411,041 | B2 | 8/2008 | Chirica et al. |
| 7,422,743 | B2 | 9/2008 | Chirica et al. |

(Continued)

FOREIGN PATENT DOCUMENTS

| | | |
|---|---|---|
| CN | 101600456 A | 12/2009 |
| DE | DD-266710 A3 | 4/1989 |

(Continued)

OTHER PUBLICATIONS

Kang, J.; Lin, K.; Penera, J.; Rapid Formulation Development for Monoclonal Antibodies. Apr. 12, 2016. (Year: 2016).*

(Continued)

*Primary Examiner* — Jeffrey Stucker
*Assistant Examiner* — Laura Ann Essex
(74) *Attorney, Agent, or Firm* — Foley & Lardner LLP

(57) ABSTRACT

The present disclosure inter alia provides a liquid pharmaceutical formulation comprising a) 150 mg/ml of an anti-IL-23p19 antibody, wherein the antibody comprises a light chain amino acid sequence according to SEQ ID NO: 1 and a heavy chain amino acid sequence according to SEQ ID NO: 2;

b) a polyol; and c) a surfactant.

The disclosed high concentration formulations are advantageously storage stable and suitable for subcutaneous administration.

8 Claims, 2 Drawing Sheets

Specification includes a Sequence Listing.

(56) References Cited

U.S. PATENT DOCUMENTS

| 7,427,402 | B2 | 9/2008 | Kastelein et al. |
|---|---|---|---|
| 7,491,391 | B2 | 2/2009 | Benson et al. |
| 7,501,247 | B2 | 3/2009 | Kastelein et al. |
| 7,510,709 | B2 | 3/2009 | Gurney |
| 7,510,853 | B2 | 3/2009 | Chirica et al. |
| 7,575,741 | B2 | 8/2009 | Bowman et al. |
| 7,608,690 | B2 | 10/2009 | Bazan |
| 7,740,848 | B2 | 6/2010 | Kastelein et al. |
| 7,749,718 | B2 | 7/2010 | Chirica et al. |
| 7,750,126 | B2 | 7/2010 | Hirata |
| 7,754,214 | B2 | 7/2010 | Chirica et al. |
| 7,790,862 | B2 | 9/2010 | Lewis et al. |
| 7,807,160 | B2 | 10/2010 | Presta et al. |
| 7,807,414 | B2 | 10/2010 | Benson et al. |
| 7,820,168 | B2 | 10/2010 | Cua et al. |
| 7,872,102 | B2 | 1/2011 | Beidler et al. |
| 7,883,695 | B2 | 2/2011 | Oppmann et al. |
| 7,887,806 | B2 | 2/2011 | Chirica et al. |
| 7,893,215 | B2 | 2/2011 | Bowman et al. |
| 7,910,703 | B2 | 3/2011 | Lewis et al. |
| 7,935,344 | B2 | 5/2011 | Benson et al. |
| 7,993,645 | B2 | 8/2011 | Benson et al. |
| 8,106,177 | B2 | 1/2012 | Benson et al. |
| 8,778,346 | B2 | 7/2014 | Barrett et al. |
| 9,441,036 | B2 | 9/2016 | Barrett et al. |
| 10,155,039 | B2 | 12/2018 | Manning et al. |
| 10,202,448 | B2 | 2/2019 | Barrett et al. |
| 10,507,241 | B2 | 12/2019 | Visvanathan et al. |
| 11,078,265 | B2 | 8/2021 | Nabozny et al. |
| 11,572,385 | B2 | 2/2023 | Garidel et al. |
| 2004/0219150 | A1 | 11/2004 | Cua et al. |
| 2004/0258686 | A1 | 12/2004 | Chirica et al. |
| 2005/0039222 | A1 | 2/2005 | Habu et al. |
| 2005/0100917 | A1 | 5/2005 | Chirica et al. |
| 2005/0100918 | A1 | 5/2005 | Chirica et al. |
| 2005/0100965 | A1 | 5/2005 | Ghayur et al. |
| 2005/0208052 | A1 | 9/2005 | Katsikis et al. |
| 2005/0244874 | A1 | 11/2005 | Kastelein et al. |
| 2005/0287593 | A1 | 12/2005 | Kastelein et al. |
| 2006/0088523 | A1 | 4/2006 | Andya et al. |
| 2006/0140958 | A1 | 6/2006 | Hogan et al. |
| 2007/0009526 | A1 | 1/2007 | Benson et al. |
| 2007/0218060 | A1 | 9/2007 | Long et al. |
| 2008/0199460 | A1 | 8/2008 | Cua et al. |
| 2008/0200655 | A1 | 8/2008 | Sek |
| 2008/0254026 | A1 | 10/2008 | Long et al. |
| 2008/0311043 | A1 | 12/2008 | Hoffman et al. |
| 2009/0060906 | A1 | 3/2009 | Barry et al. |
| 2009/0068195 | A1 | 3/2009 | Vugmeyster et al. |
| 2009/0092604 | A1 | 4/2009 | Cua et al. |
| 2009/0123479 | A1 | 5/2009 | Bembridge et al. |
| 2009/0156788 | A1 | 6/2009 | Presta et al. |
| 2009/0291062 | A1 | 11/2009 | Fraunhofer et al. |
| 2010/0003251 | A1 | 1/2010 | Oft et al. |
| 2010/0041144 | A1 | 2/2010 | Bazan |
| 2010/0111950 | A1 | 5/2010 | Cua et al. |
| 2010/0111954 | A1 | 5/2010 | Cua et al. |
| 2010/0111966 | A1 | 5/2010 | Presta et al. |
| 2010/0135998 | A1 | 6/2010 | Bowman et al. |
| 2010/0143357 | A1 | 6/2010 | Cua et al. |
| 2010/0172862 | A1 | 7/2010 | Correia et al. |
| 2010/0254991 | A1 | 10/2010 | Kastelein et al. |
| 2010/0261273 | A1 | 10/2010 | Chirica et al. |
| 2010/0266582 | A1 | 10/2010 | Gurney |
| 2010/0266583 | A1 | 10/2010 | Gurney |
| 2010/0272731 | A1 | 10/2010 | Presta et al. |
| 2010/0291084 | A1 | 11/2010 | Kopf et al. |
| 2010/0322863 | A1 | 12/2010 | Benson et al. |
| 2011/0002942 | A1 | 1/2011 | Presta et al. |
| 2011/0059087 | A1 | 3/2011 | Lewis et al. |
| 2011/0135597 | A1 | 6/2011 | Bowman et al. |
| 2011/0142831 | A1 | 6/2011 | Cua et al. |
| 2011/0142853 | A1 | 6/2011 | Presta et al. |
| 2011/0159589 | A1 | 6/2011 | Lewis et al. |
| 2011/0177022 | A1 | 7/2011 | Oppmann et al. |
| 2011/0195455 | A1 | 8/2011 | Benson et al. |
| 2011/0206686 | A1 | 8/2011 | Bembridge et al. |
| 2011/0212104 | A1 | 9/2011 | Beaumont et al. |
| 2011/0229490 | A1 | 9/2011 | Li et al. |
| 2011/0250201 | A1 | 10/2011 | Smith |
| 2011/0311527 | A1 | 12/2011 | Stern et al. |
| 2012/0128689 | A1 | 5/2012 | Clarkson et al. |
| 2012/0195885 | A1 | 8/2012 | Correia et al. |
| 2012/0277799 | A1 | 11/2012 | Winslow et al. |
| 2012/0282269 | A1 | 11/2012 | Barrett et al. |
| 2013/0004501 | A1 | 1/2013 | Towne et al. |
| 2013/0028907 | A1 | 1/2013 | Parshad et al. |
| 2013/0115166 | A1 | 5/2013 | Clarke et al. |
| 2013/0216525 | A1 | 8/2013 | Chen |
| 2014/0046063 | A1 | 2/2014 | Moussy et al. |
| 2014/0178383 | A1 | 6/2014 | Brige et al. |
| 2014/0178401 | A1 | 6/2014 | Nabozny et al. |
| 2014/0303357 | A1 | 10/2014 | Lim et al. |
| 2014/0363444 | A1 | 12/2014 | Barrett et al. |
| 2016/0060338 | A1 | 3/2016 | Barrett et al. |
| 2016/0222102 | A1 | 8/2016 | Arndt et al. |
| 2016/0304602 | A1 | 10/2016 | Arndt et al. |
| 2016/0333091 | A1 | 11/2016 | Barrett et al. |
| 2017/0022294 | A1 | 1/2017 | Singh et al. |
| 2017/0081402 | A1 | 3/2017 | Boecher et al. |
| 2017/0157246 | A1 | 6/2017 | Visvanathan et al. |
| 2017/0298126 | A1 | 10/2017 | Baum et al. |
| 2018/0009887 | A1 | 1/2018 | Arndt-Schmitz et al. |
| 2018/0105588 | A1 | 4/2018 | Baum et al. |
| 2018/0334501 | A1 | 11/2018 | Arndt-Schmitz et al. |
| 2019/0309016 | A1 | 10/2019 | Garidel et al. |
| 2020/0299378 | A1 | 9/2020 | Baum et al. |
| 2020/0308271 | A1 | 10/2020 | Baum et al. |
| 2020/0376117 | A1 | 12/2020 | Visvanathan et al. |
| 2021/0198355 | A1 | 7/2021 | Barrett et al. |
| 2021/0317201 | A1 | 10/2021 | Nabozny et al. |

FOREIGN PATENT DOCUMENTS

| EP | 0 736 57 | A1 | 3/1983 |
|---|---|---|---|
| EP | 0 183 070 | A2 | 6/1986 |
| EP | 0 244 234 | A2 | 11/1987 |
| EP | 0 402 226 | A1 | 12/1990 |
| EP | 1 072 610 | A1 | 1/2001 |
| EP | 2 786 746 | A1 | 10/2014 |
| JP | 2015-517465 | A | 6/2015 |
| WO | WO-81/01145 | A1 | 4/1981 |
| WO | WO-87/00195 | A1 | 1/1987 |
| WO | WO-88/07378 | A1 | 10/1988 |
| WO | WO-90/03430 | A1 | 4/1990 |
| WO | WO-90/13646 | A1 | 11/1990 |
| WO | WO-94/04188 | A1 | 3/1994 |
| WO | WO-94/11026 | A2 | 5/1994 |
| WO | WO-96/24369 | A1 | 8/1996 |
| WO | WO-96/32478 | A1 | 10/1996 |
| WO | WO-99/05280 | A1 | 2/1999 |
| WO | WO-99/40195 | A1 | 8/1999 |
| WO | WO-99/54357 | A1 | 10/1999 |
| WO | WO-01/18051 | A2 | 3/2001 |
| WO | WO-01/85790 | A2 | 11/2001 |
| WO | WO-03/039485 | A2 | 5/2003 |
| WO | WO-2004/042009 | A2 | 5/2004 |
| WO | WO-2004/058178 | A2 | 7/2004 |
| WO | WO-2004/071517 | A2 | 8/2004 |
| WO | WO-2004/081190 | A2 | 9/2004 |
| WO | WO-2005/044294 | A2 | 5/2005 |
| WO | WO-2005/052157 | A1 | 6/2005 |
| WO | WO-2005/079837 | A1 | 9/2005 |
| WO | WO-2005/108616 | A1 | 11/2005 |
| WO | WO-2006/036922 | A2 | 4/2006 |
| WO | WO-2006/068987 | A2 | 6/2006 |
| WO | WO-2007/005647 | A2 | 1/2007 |
| WO | WO-2007/005955 | A2 | 1/2007 |
| WO | WO-2007/024846 | A2 | 3/2007 |
| WO | WO-2007/027714 | A2 | 3/2007 |
| WO | WO-2007/027761 | A2 | 3/2007 |
| WO | WO-2007/076523 | A2 | 7/2007 |
| WO | WO-2007/076524 | A2 | 7/2007 |
| WO | WO-2007/147019 | A2 | 12/2007 |

(56) References Cited

FOREIGN PATENT DOCUMENTS

| WO | WO-2007/149814 A1 | 12/2007 | |
|----|----|----|----|
| WO | WO-2008/101145 A1 | 8/2008 | |
| WO | WO-2008/103432 A1 | 8/2008 | |
| WO | WO-2008/103473 A1 | 8/2008 | |
| WO | WO-2008/106131 A2 | 9/2008 | |
| WO | WO-2008/153610 A2 | 12/2008 | |
| WO | WO-2009/032954 A1 | 3/2009 | |
| WO | WO-2009/043933 A1 | 4/2009 | |
| WO | WO-2009/053493 A1 | 4/2009 | |
| WO | WO-2009/055936 A1 | 5/2009 | |
| WO | WO-2009/073569 A2 | 6/2009 | |
| WO | WO-2009/082624 A2 | 7/2009 | |
| WO | WO-2010/017598 A1 | 2/2010 | |
| WO | WO-2010/027766 A1 | 3/2010 | |
| WO | WO-2010/115092 A2 | 10/2010 | |
| WO | WO-2010/115786 A1 | 10/2010 | |
| WO | WO-2011/011797 A2 | 1/2011 | |
| WO | WO-2011/056600 A1 | 5/2011 | |
| WO | WO-2011/066369 A2 | 6/2011 | |
| WO | WO-2011/070339 A1 | 6/2011 | |
| WO | WO-2011/103105 A1 | 8/2011 | |
| WO | WO-2011/104381 A2 | 9/2011 | |
| WO | WO-2011/109365 A2 | 9/2011 | |
| WO | WO-2011/159655 A2 | 12/2011 | |
| WO | WO-2011/159750 A1 | 12/2011 | |
| WO | WO-2012/009760 A1 | 1/2012 | |
| WO | WO-2012/032181 A2 | 3/2012 | |
| WO | WO-2012/061448 A1 | 5/2012 | |
| WO | WO-2012/093254 A1 | 7/2012 | |
| WO | WO-2012/103345 A1 | 8/2012 | |
| WO | WO-2013165791 A1 * | 11/2013 | ....... A61K 39/39591 |
| WO | WO-2013/186230 A1 | 12/2013 | |
| WO | WO-2014/004436 A2 | 1/2014 | |
| WO | WO-2014/093203 A1 | 6/2014 | |
| WO | WO-2014/143540 | 9/2014 | |
| WO | WO-2014/149425 A1 | 9/2014 | |
| WO | WO-2016/014775 A1 | 1/2016 | |
| WO | WO-2016/036918 A1 | 3/2016 | |
| WO | WO-2016/126638 A1 | 8/2016 | |
| WO | WO-2017/048901 A1 | 3/2017 | |
| WO | WO-2017/097407 A1 | 6/2017 | |
| WO | WO-2018011404 A1 * | 1/2018 | ........... A61K 31/704 |
| WO | WO-2018/071504 A2 | 4/2018 | |
| WO | WO-2019246271 A1 * | 12/2019 | ......... A61K 31/4035 |
| WO | WO-2024/085697 | 4/2024 | |

OTHER PUBLICATIONS

Bordwell, Frederick G. Acc. Chem. Res. 1988, 21, 456-463. (Year: 1988).*

PubChem. Bethesda (MD): National Library of Medicine (US), National Center for Biotechnology Information; 2004-. PubChem Compound Summary for , Risankizumab. Available from: https:// pubchem.ncbi.nlm.nih.gov/compound/Risankizumab (Year: 2004).*

He F, Woods CE, Litowski Jr., Roschen LA, Gadgil HS, Razinkov VI, Kerwin BA. Effect of sugar molecules on the viscosity of high concentration monoclonal antibody solutions. Pharm Res. Jul. 2011;28(7):1552-60. doi: 10.1007/s11095-011-0388-7. Epub May 15, 2011. PMID: 21573867. (Year: 2011).*

"A Phase III, Multicenter Study of the Efficacy and Safety of Adalimumab Treatment in Subjects With Moderate to Severe Chronic Plaque Psoriasis," Adis Insight Trial Profile, Abbott GmbH & Co. KG, latest information update Jul. 26, 2022, 10 pages.

"A Randomised, Double-Blind, Placebo-controlled, Proof-of-concept, Dose-ranging Study of BI 655066/ABBV-066/ Risankizumab in Patients With Active Psoriatic Arthritis," Adis Insight Trial Profile, AbbVie; Boehringer Ingelheim, latest information update Nov. 6, 2021, 10 pages.

"An Open Label, Single Group, Long Term Safety Extension Trial of BI 655066/ABBV-066 (Risankizumab) in Patients With Moderately to Severely Active Crohn's Disease," Adis Insight Trial Profile, AbbVie; Boehringer Ingelheim, latest information update Sep. 17, 2021, 13 pages.

"BI 655066 Versus Ustekinumab and Placebo Comparators in a Randomized Double Blind trial for Maintenance Use in Moderate to Severe Plaque Type Psoriasis-2 (UltIMMa-2)," Adis Insight Trial Profile, AbbVie; Boehringer Ingelheim, latest information update Nov. 23, 2022, 18 pages.

"Bi 655066/ABBV-066 (Risankizumab) Versus Adalimumab in a Randomized, Double Blind, Parallel Group Trial in Moderate to Severe Plaque Psoriasis to Assess Safety and Efficacy After 16 Weeks of Treatment and After Inadequate Adalimumab Treatment response (IMMvent)," Adis Insight Trial Profile, AbbVie; Boehringer Ingelheim Pharma KG, latest information update Nov. 23, 2022, 15 pages.

"Bi 655066/ABBV-066 (Risankizumab) Versus Placebo In a Multicenter Randomized Double-blind Study in Patients With Moderate to Severe Chronic Plaque Psoriasis Evaluating the Efficacy and Safety With Randomized Withdrawal and Re-treatment (IMMhance)," Adis Insight Trial Profile, AbbVie; Boehringer Ingelheim; Boehringer Ingelheim Pharma KG, latest information update Dec. 29, 2021, 14 pages.

"Bi 655066/ABBV-066 (risankizumab) Versus Ustekinumab and placebo comparators in a randomized double blind trial for Maintenance use in Moderate to severe plaque type psoriasis (UltIMMa-1)," Adis Insight Trial Profile, AbbVie; Boehringer Ingelheim, latest information update Nov. 23, 2022, 18 pages.

"Boehringer Ingelheim Reports Results of Phase II Head-to-Head Psoriasis Study of BI 655066," Close-Up Media, Inc., Oct. 15, 2015, 1 page.

"Boehringer Ingelheim Updates on Phase II Psoriasis Study of BI 655066," Close-Up Media, Inc., Mar. 25, 2015, 1 page.

"Boehringer Ingelheim's Investigational Biologic Cleared Skin Better than Ustekinumab in Head-to- Head Phase II Psoriasis Study," Mar. 20, 2015, 14 pages.

"Efficacy and Safety of BI 655066/ABBV-066 (Risankizumab) in Patients With Severe Persistent Asthma," ClinicalTrials.gov, last update posted Apr. 10, 2019, 20 pages.

"Phase IIa, Randomized, Double-blind, Placebo Controlled, Parallel Group Study to Assess the Safety and Efficacy of Subcutaneously Administered BI 655066/ABBV-066 (Risankizumab) as add-on Therapy Over 24 Weeks in Patients With Severe Persistent Asthma," Adis Insight Trial Profile, AbbVie; Boehringer Ingelheim, latest information update Nov. 8, 2021, 11 pages.

"Safety, Tolerability, and Pharmacokinetics of Single Rising s.c. (Stage 1) and i.v. (Stage 2) Doses of BI 655066/ABBV-066 (Risankizumab) in Healthy Asian and Caucasian Male Volunteers (Double- blind, Randomized, Placebo-controlled Within Dose Groups)," Adis Insight Trial Profile, AbbVie; Boehringer Ingelheim, latest information update Jan. 16, 2020, 7 pages.

Aggarwal et al., "Interleukin-23 Promotes a Distinct CD4 T Cell Activation State Characterized by the Production of Interleukin-17*," Journal of Biological Chemistry, 2003, 278(3): 1910-1914.

Alegre et al., "A Non-Activating "Humanized" Anti-CD3 Monoclonal Antibody Retains Immunosuppressive Properties in Vivo," Transplantation; Jun. 1994, 57(11):1537-1543.

Alunno et al., "Targeting the IL-23/IL-17 axis for the treatment of psoriasis and psoriatic arthritis," Expert Opinion on Biological Therapy, 2015, 15(12):1727-1737.

Anonymous: "A 52-Week, Phase 3, Randomized, Active Comparator and Placebo-Controlled, Parallel Design Study to Evaluate the Efficacy and Safety/Tolerability of Subcutaneous SCH 9000222/ MK-3222, Followed by an Optional Long-Term Safety Extension Study, in Subjects with Moderate-to-Severe Chronic Plaque Psoriasis" Dec. 30, 2014, 4 pages, Clinical Trials Identifier: NCT01729754, Clinicaltrials.gov.

Anonymous: "A Phase 2 Multicenter, Randomized, Pacebo- and Active-Comparator-Controlled, Dose-Ranging Trial to Evaluate CNTO 1959 For the Treatment of Subjects with Moderate to Sever Plaque-type Psoriasis (X-PLORE)" Mar. 10, 2014, 4 pages, Clinical Trials Identifier NCT01483599, Clinicaltrials.gov.

Anonymous: "A Phase 2a, Multicenter, Randomized, Double-blind, Placebo-controlled Study Evaluating the Efficacy and Safety of Guselkumab in the Treatment of Subjects with Active Psoriatic Arthritis," Jan. 26, 2015, 4 pages, Clinical Trials Identifier: NCT02319759, Clinicaltrials.gov.

(56) References Cited

OTHER PUBLICATIONS

Baerveldt et al., "Ustekinumab improves psoriasis-related gene expression in noninvolved psoriatic skin without inhibition of the antimicrobial response," British Journal of Dermatology, 2013, 168:990-998.

Bahrenburg et al., "Buffer-free therapeutic antibody preparations provide a viable alternative to conventionally buffered solutions: From protein buffer capacity prediction to bioprocess applications," Biotechnology Journal, 2015, 10:610-622.

Bandzar et al., "Crohn's disease: A review of treatment options and current research," Cellular Immunology, 2013, 286:45-52.

Bankhead et al., "Novel IL-23 Inhibitor Shows Promise in Psoriasis—Interleukin-23 inhibitor has 'high efficacy, quiet safety signal'," Medpage Today, Mar. 22, 2015.

Bauer et al., "Rational optimization of a monoclonal antibody improves the aggregation propensity and enhances the CMC properties along the entire pharmaceutical process chain," MABS, 2020, 12(1):e1787121, 1-14.

Beyer et al., "Crystal Structures of the Pro-Inflammatory Cytokine Interleukin-23 and its Complex with a High-Affinity Neutralizing Antibody," Journal of Molecular Biology, 2008, 382:942-955.

Bhambhani et al., "Formulation Design and High-Throughput Excipient Selection Based on Structural Integrity and Conformational Stability of Dilute and Highly Concentrated IgG1 Monoclonal Antibody Solutions," Journal of Pharmaceutical Sciences, 2012, 101(3):1120-1135.

BioPorto Product Catalog, 2010, 28 pps.

Bjorkesten, Clas-Goran af, "Monitoring treatment response in Crohn's disease," Dissertation, Helsinki, Finland, Feb. 28, 2014, 88 pages.

Boehringer Ingelheim, BI 655066 Dose Ranging in Psoriasis, Active Comparator Ustekinumab. Available from: https://clinicaltrials. gov/ct2/show/NCT02054481. NLM identifier. NCT 02054481. First posted Feb. 4, 2014.

Boulet-Audet et al., "High-Throughput Thermal Stability Analysis of a Monoclonal Antibody by Attenuated Total Reflection FT-IR Spectroscopic Imaging," Analytical Chemistry, 2014, 86:9786-9793.

Brodmerkel et al., "The Skin and Circulating Immune Profile of Therapeutic IL-12/23 Blockade in Psoriasis Patients Treated with Ustekinumab," Clinical Immunology, Academic Press, Jan. 1, 2009, 131:S5, Abstract.

Campa et al., "A Review of Biologic Therapies Targeting IL-23 and IL-17 for Use in Moderate-to- Severe Plaque Psoriasis," Dermatology Therapy, 2016, 6:1-12.

Cao et al., "Anti-IL-23 antibody blockade of IL-23/IL-17 pathway attenuates airway obliteration in rat orthotopic tracheal transplantation," International Immunopharmacology, 2011, 11:569-575.

Capelle et al., "High throughput screening of protein formulation stability: Practical considerations," European Journal of Pharmaceutics and Biopharmaceutics, 2007, 65:131-148.

Carr et al., "Eosinophilic and Noneosinophilic Asthma," Am J. Respir Crit. Care Med., 2018, 197(1):22-37.

Casset et al., "A peptide mimetic of an anti-CD4 monoclonal antibody by rational design," Biochemical and Biophysical Research Communications, 2003, 307:198-205.

Castro et al., "Reslizumab for Poorly Controlled, Eosinophilic Asthma, A Randomized, Placebo-controlled Study," Am. J. Respir. Crit. Care Med., 2011, 184:1125-1132.

Catalog No. AF1716. "Anti-human IL-23 p19 Antibody," Lot No. JMB01., R&D Systems, Inc., Dec. 17, 2003.

Chan et al., "Therapeutic antibodies for autoimmunity and inflammation," Nature Reviews, Immunology, May 2010, 10:301-316.

Chang et al., "Practical Approaches to Protein Formulation Development," Rational Design of Stable Protein Formulations—Theory and Practice (Carpenter et al., eds.,), Kluwer Academic/Plenum Publishers, New York, 2002, 1-25.

Chi et al., "Physical Stability of Proteins in Aqueous Solution: Mechanism and Driving Forces in Nonnative Protein Aggregation," Pharmaceutical Research, Sep. 2003, 20(9):1325-1336.

Chiricozzi et al., Role of IL-23 in the pathogenesis of psoriasis: a novel potential therapeutic target?, Expert Opinion Ther. Targets, 2014, 18:1-13.

Choy et al., "Th2 and Th17 inflammatory pathways are reciprocally regulated in asthma," www.ScienceTranslationalMedicine.org, 2015, 7(301):301ra129, 11 pages.

Ciprandi et al., "Serum IL-23 in Asthmatic Children," Journal of Biological Regulators & Homeostatic Agents, 2012, 26(1(S)):53-61.

Ciprandi et al., "Serum IL-23 Strongly and Inversely Correlates with FEV1 in Asthmatic Children," International Archives of Allergy and Immunology, 2012, 159(2):183-186.

CircuLex Main Products Catalog, 3 pp., 2010.

ClinicalTrials.gov study NCT01018810, published Nov. 24, 2009, (downloaded from https://clinicaltrials.gov/ct2/history/ NCT01018810, 6 pages.

ClinicalTrials.gov study NCT01483599, published Nov. 29, 2011 (downloaded from https://clinicaltrials.gov/ct2/history/ NCT01483599, 6 pages.

ClinicalTrials.gov study NCT01729754, published Nov. 14, 2012 (downloaded from https://clinicaltrials.gov/ct2/history/ NCT01729754, 7 pages.

ClinicalTrials.gov study NCT02031276, published Jan. 8, 2014, 7 pages.

ClinicalTrials.gov study NCT02319759, published Dec. 15, 2014 (downloaded from https://clinicaltrials.gov/ct2/history/ NCT02319749), 7 pages.

Croxford et al., IL-12 and IL-23 in health and disease,: Cytokine & Growth Factor Reviews, 2014, 25:415-421.

Cui et al., "Immunoregulatory Effects of IL-23 on Inflammatory Bowel Disease," World Chinese Journal of Digestology, Jun. 8, 2009, 17(16):1649-1654, English translation.

Cui et al., "Monoclonal Antibodies: Formulations of Marketed Products and Recent Advances in Novel Delivery," Drug Development and Industrial Pharmacy, 2017, 43(4):519-530.

Daugherty et al., "Formulation and delivery issues for monoclonal antibody therapeutics," Advanced Drug Delivery Reviews, 2006, 58:686-706.

Declaration of Dr. Patrick Garidel filed in EP 17208896.5, executed Aug. 1, 2019, 1 page.

Deechongkit et al., "Physical and Biophysical Effects of Polysorbate 20 and 80 on Darbepoetin Alfa," Journal of Pharmaceutical Sciences, Sep. 2009, 98(9):3200-3217.

Demain et al., "Production of recombinant proteins by microbes and higher organisms," Biotechnology Advances, 2009, 27:297-306.

Ebioscience, Anti-Mouse IL-23 p 19 Purified; Catalog No. 14-7232; Clone G23-8; According to all information that could be obtained from publicly available sources by Applicants, G23-8 antibody was available for purchase in 2005.

Ebioscience, Anti-Mouse IL-23 p 19 Purified; Catalog No. 14-7233; Clone 5B2; According to all information that could be obtained from publicly available sources by Applicants, 5B2 antibody was available for purchase in 2007.

Ebioscience, Mouse IL-23 ELISA Ready-SET-Go! ELISA Kit, Catalog No. 88-7923, 6 pages. According to all information that could be obtained from publicly available sources by Applicants, Mouse IL-23 ELISA Ready-SET-Go! ELISA Kit was available for purchase in 2007.

Eijnden, Serge Vanden et al., "Preferential production of the IL-12(p40)/ IL-23(19) heterodimer by dendritic cells from human newborns," Eur. J. Immunol., 2006, 36:21-26.

Emami et al., "Drying Technologies for the Stability and Bioavailability of Biopharmaceuticals," Pharmaceutics, Aug. 17, 2018, 10:131, 1-22.

Erstad et al., "Osmolality and Osmolarity: Narrowing the Terminology Gap," Pharmacotherapy, 2003, 23(9):1085-1086.

Eu et al., "Direct Visualization of Protein Adsorption to Primary Containers by Gold Nanoparticles," Journal of Pharmaceutical Sciences, May 2011, 100(5):1663-1670.

Fahy, John V., "Eosinophilic and Neutrophilic Inflammation in Asthma, Insights from Clinical Studies," Proceedings of the American Thoracic Society, 2009, 6:256-259.

(56)          References Cited

OTHER PUBLICATIONS

Feagan et al., "Efficacy and Safety of Induction Therapy With the Selective IL-23 Inhibitor BI 655066, in Patients With Moderate-to-Severe Crohn's Disease: Results of a Randomized, Double-Blind, Placebo-Controlled Phase II Study," Gastroenterology, Apr. 2016, 150(4: Suppl. 1), S-1266.

Ferrara et al., "Recombinant renewable polyclonal antibodies," mABs, 2015, 7(1):32-41.

Fichtner-Feigl et al., "Treatment of murine Th1- and Th2-mediated inflammatory bowel disease with NF-κB decoy oligonucleotides," Journal of Clinical Investigation, Nov. 2005, 115(11):3057-3071.

Frokjaer et al., "Protein Drug Stability: A Formulation Challenge," Nature Reviews Drug Discovery, 2005, 4:298-306.

Gaffen et al., "The IL-23-IL-17 immune axis: from mechanisms to therapeutic testing," Nature Reviews, 2014, 14:585-600.

Garrett et al., Eds., Biochemistry, 2nd Ed., 1999, Chapter 5, Proteins: Their Biological Functions and Primary Structure, 107-150.

Gokarn et al., "Self-Buffering Antibody Formulations," Journal of Pharmaceutical Sciences, Aug. 2008, 97(8):3051-3066.

Goldberg et al., "Formulation Development of Therapeutic Monoclonal Antibodies Using High-Throughput Fluorescence and Static Light Scattering Techniques: Role of Conformational and Colloidal Stability," Journal of Pharmaceutical Sciences, Apr. 2011, 100(4):1306-1315.

Gordon et al., "A Phase 2 Trial of Guselkumab versus Adalimumab for Plaque Psoriasis," New England Journal of Medicine, 2015, 373(2):136-144.

Gras, J., "Guselkumab," Drugs of the Future, 2017, 42(2):81-86.

Gudjonsson et al., "Assessment of the Psoriatic Transcriptome in a Large Sample: Additional Regulated Genes and Comparisons with In Vitro Models," Journal of Investigative Dermatology, 2010, 130:1829-1840.

Haldar et al., "Mepolizumab and Exacerbations of Refractory Eosinophilic Asthma," The New England Journal of Medicine, 2009, 360:973-984.

Happel et al., "Divergent roles of IL-23 and IL-12 in host defense against Klebsiella pneumoniae" Journal of Experimental Medicine, Sep. 2005, 202(6):761-769.

Hartl et al., "Characterizing protein-protein-interaction in high-concentration monoclonal antibody systems with the quartz crystal microbalance," Phys. Chem. Chem. Phys., 2017, 19:32698-32707.

Hawe et al., "Forced Degradation of Therapeutic Proteins," Journal of Pharmaceutical Sciences, Mar. 2012, 101(3):895-913.

Hegazi et al., "Carbon monoxide ameliorates chronic murine colitis through a heme oxygenase 1-dependent pathway," Journal of Experimental Medicine, Dec. 2005, vol. 202, No. 12, pp. 1703-1713.

Hegyi et al., "Vitamin D Analog Calcipotriol Suppresses the Th17 Cytokine-Induced Proinflammatory S100 'Alarmins' Psoriasin (S100A7) and Koebnerisin (S100A15) in Psoriasis," Journal of Investigative Dermatology, 2012, 132:1416-1424.

Higgins et al., "Carbohydrate analysis throughout the development of a protein therapeutic," Glycoconj. J., 2010, 27:211-225.

Hoeve et al., "IL-12 receptor deficiency revisited: IL-23-mediated signaling is also impaired in human genetic IL-12 receptor ?1deficiency," Eur. J. Immunol., 2003, 33:3393-3397.

Hu et al., "Information contributed by meta-analysis in exposure-response modeling: application to phase 2 does selection of guselkumab in patients with moderate-to-severe psoriasis," Journal of Pharmacokinet. Pharmacodyn., 2014, 41:239-250.

HUMIRA label, Apr. 2017, 100 pages.

HUMIRA label, Dec. 2011, 70 pages.

HUMIRA label, Jun. 2016, 100 pages.

HUMIRA label, Nov. 2015, 90 pages.

HUMIRA label, Oct. 2016, 95 pages.

INN risankizumab, WHO Drug Information, Jul. 10, 2015, 29(2):195, 196, 254 and 255.

International Preliminary Report on Patentability and Written Opinion for PCT/US2015/041706 dated Feb. 2, 2017.

International Preliminary Report on Patentability and Written Opinion for PCT/US2017/027332 dated Oct. 16, 2018.

International Preliminary Report on Patentability dated Mar. 17, 2022 in PCT PCT/IB2020/058347.

International Preliminary Report on Patentability for PCT/US2011/058869 dated May 7, 2013.

International Search Report & Written Opinion for PCT/US2011/058869, dated Feb. 27, 2012.

International Search Report and Written Opinion dated Jul. 28, 2017, in PCT/US2017/027332.

International Search Report and Written Opinion dated Oct. 26, 2017 in PCT/US2016/027263.

International Search Report and Written Opinion in PCT/IB2020/058347 dated Jan. 28, 2021.

International Search Report for PCT/US2013/038109 dated Apr. 25, 2013.

International Search Report for PCT/US2015/041706 dated Oct. 15, 2015.

International Search Report for PCT/US2016/016061 dated May 18, 2016.

International Search Report for PCT/US2016/027263 dated Jun. 29, 2016.

International Search Report for PCT/US2016/051844 dated Jan. 10, 2017.

Irvin et al., "Increased frequency of dual-positive TH2/TH17 cells in bronchoalveolar lavage fluid characterizes a population of patients with severe asthma," Journal of Allergy and Clinical Immunology, 2014, 134(5):1175-1186.

Jabbari et al., "Transcriptional Profiling of Psoriasis Using RNA-seq Reveals Previously Unidentified Differentially Expressed Genes," Journal of Investigative Dermatology, 2012 (online Aug. 2011), 132:246-249.

Kamerzell et al., "Protein-excipient interactions: Mechanisms and biophysical characterization applied to protein formulation development," Advanced Drug Delivery Reviews, 2011, 63:1118-1159.

Kamerzell et al., "The Complex Inter-Relationships Between Protein Flexibility and Stability," Journal of Pharmaceutical Sciences, Sep. 2008, 97(9):3494-3517.

Karon, A., "IL-23 inhibitor topped ustenkinumab against psoriasis," M Dedge™ Rheumatology, Retrieved from www.mdedge.com/rheumatology, 3 pages, dated Apr. 2, 2015.

Karow et al., "Buffer Capacity of Biologics—From Buffer Salts to Buffering by Antibodies," Biotechnol. Prog., 2013, 29:480-492.

Kastelein et al., "Discovery and Biology of IL-23 and IL-27: Related but Functionally Distinct Regulators of Inflammation," Annual Reviews Immunology, 2007, 25: 221-242.

Katdare et al., Eds., Excipient Development for Pharmaceutical, Biotechnology, and Drug Delivery Systems, 2006, Chapter 17, Excipients for Protein Drugs, 291-307.

Kerdel et al., "An evolution in switching therapy for psoriasis patients who fail to meet treatment goals," Dermatologic Therapy, 2015, 28:390-403.

Khatri et al., "Paradigms in the identification and treatment of severe persistent asthma in adults," Medscape Education Pulmonary Medicine, 2012, 1-17.

Kidoya et al., "Fas Ligand Induces Cell-Autonomous IL-23 Production in Dendritic Cells, a Mechanism for Fas Ligand-Induced IL-17 Production," Journal of Immunology, 2005, 8024-8031.

Kikly et al., "The IL-23/Th17 axis: Therapeutic targets for autoimmune inflammation," Current Opinion in Immunology, 2006, 18:670-675.

Kim et al., "Diagnosis and management of psoriasis," Canadian Family Physician, 2017, 63:278-285.

Kofoed et al "New Drugs and Treatment Targets in Psoriasis," Acta Derm. Venereol., 2015, 95:133-139.

Kopp et al., "Clinical improvement in psoriasis with specific targeting of interleukin-23," Nature, 2015, 521(7551):222-226.

Krishnan et al., "Development of Formulations for Therapeutic Monoclonal Antibodies and Fc Fusion Proteins," Formulation and Process Development Strategies for Manufacturing Biopharmaceuticals, 2010, Chapter 16, 383-427.

Krueger et al., "Anti-IL-23A mAb BI 655066 for treatment of moderate-to-severe psoriasis: Safety, efficacy, pharmacokinetics,

(56) References Cited

OTHER PUBLICATIONS and biomarker results of a single-rising-dose, randomized, double-blind, placebo-controlled trial," Journal of Allergy and Clinical Immunology, Jul. 2015, 136:116-124.

Krueger et al., "IL-17A is essential for cell activation and inflammatory gene circuits in subjects with psoriasis," J. Allergy Clin. Immunol., 2012, 130:145-154.

Kuwashima et al., "Delivery of Dendritic Cells Engineered to Secrete IFN-? into Central Nervous System Tumors Enhances the Efficacy of Peripheral Tumor Cell Vaccines: Dependence on Apoptotic Pathways," Journal of Immunology, 2005, 175: 2730-2740.

Lahlou et al., "Mechanically-induced aggregation of the monoclonal antibody cetuximab," Annales Pharmaceutiques Francaises, 2009, 67:340-352.

Lalovic et al., "PK-PD Analysis of PASI with Data at Boundary: BI 655066 an Anti-IL-23 mAb for the Treatment of Psoriasis," Journal of Pharmacokinetics and Pharmacodynamics, Oct. 2015, 42(1:Suppl. 1), S64. Abstract No. T-49, 1 page.

Langowski et al,. "IL-23 promotes tumour incidence and growth," Nature, Jul. 2006, 442(27):461-465.

Le Brun et al., "A critical evaluation of self-interaction chromatography as a predictive tool for the assessment of protein-protein interactions in protein formulation development: A case study of a therapeutic monoclonal antibody," European Journal of Pharmaceutics and Biopharmaceutics, 2010, 75:16-25.

Lee et al., "Increased Expression of Interleukin 23 p19 and p40 in Lesional Skin of Patients with Psoriasis Vulgaris," Journal of Experimental Medicine, 2004, 199(1):125-130.

Lee et al., "Molecular Origins of Surfactant-Mediated Stabilization of Protein Drugs," Adv. Drug Delivery Reviews, 2011, 63:1160-1171.

Leonardi et al., "Efficacy and safety of ustekinumab, a human interleukin-12/23 monoclonal antibody, in patients with psoriasis: 76-weeks results form a randomised, double-blind, placebo- controlled trail (PHOENIX 1)," The Lancet, 2008, 371:1665-1674.

Li et al., "Silencing IL-23 expression by a small hairpin RNA protects against asthma in mice," Experimental and Molecular Medicine, 2011, 43(4):197-204.

Luo et al., "Chemical Modifications in Therapeutic Protein Aggregates Generated under Different Stress Conditions," The Journal of biological Chemistry, Jul. 15, 2011, 286(28):25134-25144.

MacCallum et al., "Antibody-antigen Interactions: Contact Analysis and Binding Site Topography," J. Mol. Biol., 1996, 262:732-745.

Mahler et al., "Protein Aggregation: Pathways, Induction Factors and Analysis," Journal of Pharmaceutical Sciences, Sep. 2009, 98(9):2909-2934.

Mallbris et al., "Neutrophil gelatinase-associated lipocalin is a marker for dysregulated keratinocyte differentiation in human skin" Experimental Dermatology, 2002, 11:584-591.

Manning et al., "Stability of Protein Pharmaceuticals: An Update," Pharmaceutical Research, Apr. 2010, 27(4):544-575.

McInnes et al., "Efficacy and safety of secukinumab, a fully human anti-interleukin-17A monoclonal antibody, in patients with moderate-to-severe psoriatic arthritis: a 24-week, randomised, double-blind, placebo-controlled, phase II proof-of-concept trail," Ann. Rheum. Dis., 2014, 73:349-356.

McKinley et al., "TH17 Cells Mediate Steroid-Resistant Airway Inflammation and Airway Hyperresponsiveness in Mice," The Journal of Immunology, 2008, 181:4089-4097.

Morelli et al., "CD4+ T Cell Responses Elicted by Different Subsets of Human Skin Migratory Dendritic Cells," The Journal of Immunology, 2005, 175:7905-7915.

Mortezavi et al., "IL12/IL23 Inhibition in the Treatment of Psoriatic Arthritis," Curr. Treat. Options in Rheum., 2015, 1:197-209.

Naji et al., "T Helper 17 Cells and Related Cytokines after Allergen Inhalation Challenge in Allergic Asthmatics," International Archives of Allergy & Immunology, 2014, 165:27-34.

Nakajima et al., "Role of IL-23 and Th17 Cells in Airway Inflammation in Asthma," Immune Network, 2010, 10(1):1-4.

Narasimhan et al., "High-dose monoclonal antibodies via the subcutaneous route: challenges and technical solutions, an industry perspective," Therapeutic Delivery, 2012, 3(7):889-900.

Nema et al., "Excipients and Their Role in Approved Injectable Products: Current Usage and Future Directions," PDA Journal of Pharmaceutical Science and Technology, 2011, 65:287-332.

Noda et al., "The translational revolution and use of biologics in patients with inflammatory skin diseases," J. Allergy Clin. Immunol., 2015, 135:324-336.

Nony et al., "Impact of osmolality on burning sensations during and immediately after intramuscular injection of 0.5 ml of vaccine suspension in healthy adults," Vaccine, 2001, 19:3645-3651.

Oppmann et al., Novel p19 Protein Engages IL-12p40 to Form a Cytokine, IL-23, with Biological Activities Similar as Well as Distinct from IL-12,$201D Immunity, 2000, 13:715-725.

Osmola-Mankowska, Angieszka, "Generalised pustular psoriasis—a case report and review of therapeutic approaches," Przegl. Dermatol., 2014, 6(101):473-476.

Ota et al., "Phase 3 study of guselkumab, a human mAb directed against the p19 subunit of IL23, in Japanese subjects with generalized pustular psoriasis and erythrodermic psoriasis," J. Am. Acad. Dermatol., Jun. 2017, 76(6):AB196, abstract 4526.

Otzen, Daniel, "Protein-surfactant interactions: A tale of many states," Biochimica et Biophysica Acta, 2011, 1814:562-591.

Papp et al., "Efficacy and Safety of Different Dose Regimens of a Selective IL-23p19 Inhibitor (BI 655066) Compared with Ustekinumab in Patients with Moderate-to-Severe Plaque Psoriasis with and without Psoriatic Arthritis," ACR Concurrent Abstract Session, Nov. 9, 2015 (first publication Sep. 29, 2015), 2 pages.

Papp et al., "Tildrakizumab (MK-3222) an anti-interleukin-23p19 monoclonal antibody, improves psoriasis in a phase IIb randomized placebo-controlled trial," British Journal of Dermatology, 2015, 173:930-939.

Papp, Kim A., "Superior Onset and Duration of BI-655066 Compared to Ustekinumab," European Academy of Dermatology and Venereology (EADV) 24th Annual Congress, Oct. 7-11, 2015, 767-769.

Parham et al., "A Receptor for the Heterodimeric Cytokine IL-23 is Composed of IL-12Rβ1 and a Novel Cytokine Receptor Subunit, IL-23R," Journal of Immunology, 2002, 168:5699-5708.

Parrini et al., "Abnormal Oral Mucosal Light Reflectance in Infantile Hypertrophic Pyloric Stenosis," Journal of Pediatric and Gastroenterology and Nutrition, Jul. 2004, 39:53-55.

Partial European Search Report dated Aug. 16, 2019 in EP 19176173.3.

Patel et al., "Emerging Therapies for the Treatment of Psoriasis,," Dermatol Ther. (Heidelb), 2012, 2:16, 10 pages.

Paul, William E., M.D., Fundamental Immunology, 3rd Ed., Raven Press, New York, Chapter 8, 1993, 292-295.

Perkins, Mark, "Recombinant Albumin Facilitates Formulation Design of Stable Drug Products," BioPharm International, 2012, 25:40-44.

Pirhonen et al., "Regulation of Virus-Induced IL-12 and IL-23 Expression in Human Macrophages," Journal of Immunology, 2002, 5673-5678.

Piskin et al., "Clinical Improvement in chronic plaque-type psoriasis lesions after narrow-band UVB therapy is accompanied by a decrease in the expression of IFN-γ inducers—IL-12, IL-18, and IL-23," Experimental Dermatology, 2004, 13:764-772.

Piskin, Gamze "IL-23 Expression by Keratinocytes," Effects of Therapies on Cytokine Patterns of Psoriasis, 2004, Chapter 7, 114-131.

PROLIA label, Jun. 2010, 18 pages.

R&D Systems New Products, Jun. 2005. 12 pgs. www.RnDSystems.com.

R&D Systems, de novo newsletter, Mar. 2004, 10 pgs. www.rndsystems.com.

Rasch et al., "24th European Academy of Dermatology and Venereology," Immunotherapy, Mar. 14, 2016, 8(4):395-397.

Rouet et al., "Stability engineering of the human antibody repertoire," FEBS Letters, 2014, 588:269-277.

Sacha et al., "Practical fundamentals of glass, rubber, and plastic sterile packaging systems," Pharmaceutical Development and Technology, Feb. 2010, 15(1):6-34.

(56)                    References Cited

OTHER PUBLICATIONS

Sandborn et al., "Ustekinumab Induction and Maintenance Therapy in Refractory Crohn's Disease," The New England Journal of Medicine, 2012, 367(16):1519-1528.

Sands et al., "A randomized, double-blind placebo-controlled phase 2a induction study of MEDI2070 (anti-p19 antibody) in patients with active Crohn's disease who have failed anti-TNF antibody therapy," Journal of Crohn's and Colitis, Feb. 1, 2015, 9(Supp_1):S15-S16, OP025.

Savage et al. "Ustekinumab in the Treatment of Psoriasis and Psoriatic Arthritis," Rheumatol. Ther., 2015, 2:1-16.

Sehy et al., Abstract 560.34 "Unambiguous Detection of IL-23 (p19/p40) Protein in Native Samples Using a Novel Enzyme-Linked Immunosorbent Assay," Experimental Biology, 2005, A945-A946, International Congress of Physiological Sciences.

Sharma et al., "The Formulation and Delivery of Monoclonal Antibodies," Chapter 30 in Therapeutic Monoclonal Antibodies: From Bench to Clinic, Zhiquang An, Ed., 2009, 675-709.

Shi et al., "Biophysical Characterization and Stabilization of the Recombinant Albumin Fusion Protein sEphB4-HSA," Journal of Pharmaceutical Sciences, Jun. 2012, 101(6):1969-1984.

Shire et al., "Challenges in the Development of High Protein Concentration Formulations," Journal of Pharmaceutical Sciences, Jun. 2004, 93(6):1390-1402.

Shire, Steven J., Monoclonal Antibodies: Meeting the Challenges in Manufacturing, Formulation, Delivery and Stability of Final Drug Product, 2015.

Shukla et al., "Understanding the Synergistic Effect of Arginine and Glutamic Acid Mixtures on Protein Solubility," The Journal of Physical Chemistry B, 2011, 115:11831-11839.

SIGMA Life Science, Products for Life Science Research, 2008-2009, 6 pages.

Singh et al., "Selective targeting of the IL23 pathway: Generation and characterization of a novel high-affinity humanized anti-IL23A antibody," MABS, Apr. 23, 2015, 7(4):778-791.

Sofen et al., "Guselkumab (an IL-23-specific mAb) demonstrates clinical and molecular response in patients iwth moderate-to-severe psoriasis," Journal of Allergy and Clinical Immunology, 2014,133:1032-1040.

Sola et al., "Effects of Glycosylation on the Stability of Protein Pharmaceuticals," Journal of Pharmaceutical Sciences, Apr. 2009, 98(4):1223-1245.

Strickley et al., "A review of formulations of commercially available antibodies," Journal of Pharmaceutical Sciences, 2021, 110:2590-2608.

Strober, B., "Interleukin-23 inhibition for the treatment of psoriasis: the next frontier for high-efficacy biologic therapy," British Journal of Dermatology, 2015, 173:886-895.

Suarez-Farinas et al., "Expanding the Psoriasis Disease Profile: Interrogation of the Skin and Serum of Patients with Moderate-to-Severe Psoriasis," Journal of Investigative Dermatology, 2012, 132:2552-2564.

Supplementary European Search Report dated Jun. 2, 2022 in EP 21191271.2.

Tang et al., "Interleukin-23: as a drug target for autoimmune inflammatory diseases," Immunology, 2011, 135:112-124.

Tian et al., "Meta-Analysis Derived (MAD) Transcriptome of Psoriasis Defines the "Core" Patheogenesis of Disease," PLOS One, 2012, 7(9):e44274, 15 pages.

Tonel et al., "Cutting Edge: A Critical Functional Role for IL-23 in Psoriasis," The Journal of Immunology, 2010, 185:5688-5691.

Usui, T., "The relationship between oral mucosal immunity and activity of dental caries after prolonged strenuous exercise," Descente Sports Science, 2014, 35:37-43.

Vajdos et al., "Comprehensive Functional Maps of the Antigen-binding Site of an Anti-ErbB2 Antibody Obtained with Shotgun Scanning Mutagenesis", J. Mol. Biol., Jul. 5, 2002, 320:415-428.

Van Berkel et al., "N-Linked Glycosylation is an Important Parameter for Optimal Selection of Cell Lines Producing Biopharmaceutical Human IgG," Biotechnol. Prog., 2009, 25(1):244-251.

Verreck et al., "Human IL-23-producing type 1 macrophages promote but IL-10 producing type 2 macrophages subvert immunity to (myco)bacteria," PNAS, 2004, 101(13):4560-4565.

Visvanathan et al., "IL-23 pathway inhibition by risankizumab differentially modulates the molecular and histopathological profile in psoriatic skin compared with ustekinumab," Experimental Dermatology, 2016, 25(Suppl. 4):3-51, Abstract P061.

Wakashin et al., "IL-23 and Th17 Cells Enhance Th2-Cell-mediated Eosinophilic Airway Inflammation in MIce" American Journal of Respiratory and Critical Care Medicine, 2008, 178:1023-1032.

Wang et al,. "Antibody Structure, Instability, and Formulation," Journal of Pharmaceutical Sciences, Jan. 1, 2007, 96(1):1-26.

Wang et al., Aggregation of Therapeutic Proteins, 2010.

Wang, Wei, "Review: Instability, stabilization, and formulation of liquid protein pharmaceuticals," International Journal of Pharmaceutics, 1999, 185:129-188.

Wenzel, Sally, "Severe asthma: from characteristics to phenotypes to endotypes," Clinical & Experimental Allergy, 2012, 42:650-658.

Wikipedia entry for "Guselkumab," 5 pages, downloaded May 29, 2018.

Wong et al., "Simultaneous High-Throughput Conformational and Colloidal Stability Screening Using a Fluorescent Molecular Rotor Dye, 4-(4-(Dimethylamino)styryl)-N-Methylpyridinium Iodide (DASPMI)," Journal of Biomolecular Screening, 2016, 21(8):842-850.

Woodle et al., "Phase I Trial of a Humanized, Fc Receptor Non-binding OKT3 Antibody, huOKT3?1(Ala-Ala) In the Treatment of Acute Renal Allograft Rejection," Transplantation, 1999, 68(5):608-616.

Written Opinion dated Aug. 17, 2017, in PCT/US2016/016061.

Yannam et al., "IL-23 in Infections, Inflammation, Autoimmunity and Cancer: Possible Role in HIV-1 and AIDS," Journal of Neuroimmune Pharmacology, 2012, 7:95-112.

Yeilding et al., "Development of the IL-12/23 antagonist ustekinumab in psoriasis: past, present and future perspectives," Annals of the New York Academy of Sciences, 2011, 1222:30-39.

Zakharova et al., "Paradoxical Anti-Inflammatory Actions of TNF-a: Inhibition of IL-12 and IL-23 via TNF Receptor 1 in Macrophages and Dendritic Cells" Journal of Immunology, 2005, 175:5024-5033.

Zheng et al., "Influence of pH, buffer species, and storage temperature on physicochemical stability of a humanized monoclonal antibody LA298," International Journal of Pharmaceutics, 2006, 308:46-51.

Zheng et al., "The impact of glycosylation on monoclonal antibody conformation and stability," MABS, Nov./Dec. 2011, 3(6):568-576.

"Internal Medicine—Crohn's Disease and Chronic Ulcerative Colon," https://doctor.get.com.tw/m/Journal/detail.aspx?no=402782, with English machine translation, accessed May 30, 2022, 3 pages.

Abdo et al. "Interleukin 23 and autoimmune diseases: current and possible future therapies," Inflammation Research, May 2020, 69(5):463-480.

Al-Lazikani et al., "Standard conformations for the canonical structures of immunoglobulins," J. Mol. Biol., 1997, 273:927-948.

Altschul et al., "Basic Local Alignment Search Tool," J. Mol. Biol., (1990), 215:403-410.

Altschul et al., "Gapped BLAST and PSI-BLAST: a new generation of protein database search programs," Nucleic Acids Res., (1997), 25:3389-3402.

Bachelez, Herve, M.D., PhD., "Pustular variants of psoriasis: an update," BI 655066 Psoriasis Advisory Board Meeting, New York, Sep. 4, 2015-; 2015, 104 pages.

Barnes et al., "Methods for Growth of Cultured Cells in Serum-Free Medium," Anal. Biochem., 1980, 102, 255-270.

Baylot et al., "TCTP Has a Crucial Role in the Different Stages of Prostate Cancer Malignant 4 Progression 5," Results and Problems in Cell Differentiation, 2017, 64:255-261.

Botkin et al., "Targeted therapy for psoriatic disease," Russian Journal of Clinical Dermatology and Venereology, 2017, 17(4):18-29, with English machine translation.

Brennan et al., "Preparation of bispecific antibodies by chemical recombination of monoclonal immunoglobulin G1 fragments," Science, 1985, 229:81-83.

(56)　　　　　References Cited

OTHER PUBLICATIONS

Buchwald et al., "Long-term, continuous intravenous heparin administration by an implantable infusion pump in ambulatory patients with recurrent venous thrombosis," Surgery, Oct. 1980, 88:507-516.

Caron et al., "Engineered humanized dimeric forms of IgG are more effective antibodies," J. Exp. Med., Oct. 1992, 176:1191-1195.

Carter et al., "High level Escherichia coli expression and production of a bivalent humanized antibody fragment," Bio/Technology, Feb. 1992, 10:163-167.

Chothia et al., "Canonical Structures for the Hypervariable Regions of Immunoglobulins," J. Mol. Biol., 1987, 196:901-917.

Chothia et al., "Domain Association in Immunoglobulin Molecules— The Packing of Variable Domains," J. Mol. Biol., 1985, 186:651-663.

Clackson et al., "Making antibody fragments using phage display libraries," Nature, 1991, 352:624-628.

Cunningham et al., "High-resolution epitope mapping of hGH-receptor interactions by alanine-scanning mutagenesis," Science, Jun. 2, 1989, 244:1081-1085.

D'Haens et al., Risankizumab as induction therapy for Crohn's disease: results from the phase 3 ADVANCE and MOTIVATE induction trials, Lancet, 2022, 399:2015-2030.

During et al., "Controlled release of dopamine from a polymeric brain implant: in vivo characterization," Ann. Neurol., Apr. 1989, 25(4):351-356.

Edge et al., "Deglycosylation of glycoproteins by trifluoromethanesulfonic acid," Anal. Biochem., 1981, 118:131-137.

Edwards et al., "The remarkable flexibility of the human antibody repertoire; isolation of over one thousand different antibodies to a single protein, BLyS", Journal of Molecular Biology, Sep. 24, 2003, 334(1):103-118.

Epstein et al., "Biological activity of liposome-encapsulated murine interferon gamma is mediated by a cell membrane receptor," Proc. Natl. Acad. Sci. USA, Jun. 1985, 82:3688-3692.

Evan et al., "Isolation of monoclonal antibodies specific for human c-myc proto-oncogene product," Molecular and Cellular Biology, Dec. 1985, 5(12):3610-3616.

Feagan et al., "Efficacy and safety of induction therapy with the selective IL-23 inhibitor risankizumab (BI 655066) in patients with moderate-to-severe Crohn's disease: results of a randomized, double-blind, placebo-controlled phase II study," Digestive Disease Week (DDW) 2016, San Diego, May 31, 2016-May 24, 2016; 2016, 23 pages.

Feagan et al., "Efficacy and safety of re-induction treatment with the selective IL-23 inhibitor risankizumab in patients with moderate-to-severe Crohn's disease," 24th United Eur Gastroenterology Week (UEGW), Vienna, Oct. 15, 2016-Oct. 19, 2016; 2016, 14 pages.

Feagan et al., "Efficacy and safety of re-induction treatment with the selective IL-23 inhibitor risankizumab in patients with moderate-to-severe Crohn's disease," 24th United Eur Gastroenterology Week (UEGW), Vienna, Oct. 15, 2016-Oct. 19, 2016; United Eur Gastroenterol J; 2016; 4(6); Abstr LB17; 806-807.

Field et al., "Purification of RAS-Responsive Adenylyl Cyclase Complex from Saccharomyces cerevisiae by Use of an Epitope Addition Method," Mol. Cell. Biol., May 1988, 8(5):2159-2165.

Fleer et al., "Stable multicopy vectors for high-level secretion of recombinant human serum albumin by Kluyveromyces yeasts," Bio/Technology, Oct. 1991, 9:968-975.

Gabizon et al., "Pharmacokinetics and Tissue Distribution of Doxorubicin Encapsulated in Stable Liposomes with Long Circulation Times," J. National Cancer Inst., 1989, 81(19):1484-1488.

Goel et al., "Plasticity within the Antigen-Combining Site May Manifest as Molecular Mimicry in the Humoral Immune Response," The Journal of Immunology, Dec. 15, 2004, 173(12):7358-7367.

Gooderham et al., "Shifting the focus—the primary role IL-23 in psoriasis and other inflammatory disorders," J. Eur. Acad. Dermatol. Venereol., 2018, 32(7):1111-1119.

Graham et al., "Characteristics of a human cell line transformed by DNA from human adenovirus type 5," J. Gen. Virol., 1977, 36:59-74.

Guss et al., "Structure of the IgG-binding regions of streptococcal protein G,"EMBO J., 1986, 5:1567-1575.

Hakimuddin et al., "A chemical method for the deglycosylation of proteins," Arch. Biochem. Biophys., Nov. 15, 1987, 259, 52-57.

Ham et al., "Media and growth requirements," Meth. Enz., 1979, 58, 44-93.

Hezareh et al., "Effector Function Activities of a Panel of Mutants of a Broadly Neutralizing Antibody against Human Immunodeficiency Virus Type 1," Journal of Virology, Dec. 2001, vol. 75, No. 24 (pp. 12161-12168).

Higgins et al., "Using CLUSTAL for Multiple Sequence Alignments," Methods Enzymol., 1996, 266:383-402.

Holliger et al., "'Diabodies': Small bivalent and bispecific antibody fragments," Proc. Natl. Acad. Sci. USA, Jul. 1993, 90:6444-6448.

Howard et al., "Intracerebral drug delivery in rats with lesion-induced memory deficits," J. Neurosurg., Jul. 1989, 71(1):105-112.

Hwang et al., "Hepatic uptake and degradation of unilamellar sphingomyelin/cholesterol liposomes: a kinetic study," Proc. Natl. Acad. Sci. USA, Jul. 1980, 77:4030-4034.

Ishikawa et al., "Influence of pH on heat-induced aggregation and degradation of therapeutic monoclonal antibodies," Biol. Pharm. Bull., 2010, 33(8):1413-1417.

Janeway et al., Immunobiology, 3rd edition, 1997, Garland Publishing Inc., pp. 3:1-3:11.

Jones, Elizabeth W., "Proteinase Mutants of Saccharomyces cerevisiae," Genetics, Jan. 1977, 85:23-33.

Jorgensen et al., "Recent trends in stabilising peptides and proteins in pharmaceutical formulation—considerations in the choice of excipients," Expert Opin. Drug Deliv., 2009, 6(11):1219-1230.

Kabat et al., Sequences of Proteins of Immunological Interest, 1991, NIH Publ., I, 5th Ed., No. 91, 3242:647-669.

Kanyavuz et al., "Breaking the law: unconventional strategies for antibody diversification," Nature Reviews: Immunology, Jun. 2019, 19:355-368.

Karlin et al., "Applications and statistics for multiple high-scoring segments in molecular sequences," Proc. Natl. Acad. Sci. USA, Jun. 1993, 90, 5873-5877.

Karlin et al., "Methods for assessing the statistical significance of molecular sequence features by using general scoring schemes," Proc. Natl. Acad. Sci. USA, Mar. 1990, 87:2264-2268.

Kastelein et al., "Discovery and Biology of IL-23 and IL-27: Related but Functionally Distinct Regulators of Inflammation," Annu. Rev. Immunol., 2007, 25:221-242.

Koehler et al., "Continuous cultures of fused cells secreting antibody of predefined specificity," Nature, Aug. 7, 1975, 256:495-497.

Lalovic et al., "PK-PD analysis of PASI with data at boundary: BI 655066, an anti-IL-23A mAb for the treatment of psoriasis," AcoP6, 6th American Conf on Pharmacometrics of the International Society of Pharmacometrics (IsoP), Crystal City, Oct. 4, 2015-Oct. 7, 2015; 2015, 5 pages.

Langer et al., "Chemical and Physical Structure of Polymers as Carriers for Controlled Release of Bioactive Agents: A Review," Macromol. Sci. Rev. Macromol. Chem., 1983, 23, 61-126.

Langer, Robert, "New methods of drug delivery," Science, Sep. 28, 1990, 249:1527-1533.

Leonardi, Craig L., M.D., "Antibodies in the treatment of psoriasis: IL-12/23 p40 and IL-17a," Semin Cutan Med Surg; 2016; 35(Suppl 4); S74-S77.

Levy et al., "Inhibition of calcification of bioprosthetic heart valves by local controlled-release diphosphonate," Science, Apr. 12, 1985, 228, 190-192.

Lindmark et al., "Binding of immunoglobulins to protein A and immunoglobulin levels in mammalian sera," J. Immunol. Meth., 1983, 62:1-13.

Lloyd et al., "Modelling the human immune response: performance of a 10" human antibody repertoire against a broad panel of therapeutically relevant antigens", Protein Engineering, Design & Selection, Mar. 2009 (online Oct. 29, 2008), 22(3):159-168.

Louis et al., "Risankizumab Induction Therapy in Patients With Moderately to Severely Active Ulcerative Colitis: Efficacy and

(56)           References Cited

OTHER PUBLICATIONS

Safety in the Randomized Phase 3 INSPIRE Study," United European Gastroenterology Week (UEGW), Oct. 14-17, 2023, Copenhagen, Denmark, 16 pages.

Maas et al., "PK-PD of Crohn's disease activity index after treatment with risankizumab, an IL-23 inhibitor," ACoP7, 7th American Conf on Pharmacometrics of the International Society of Pharmacometrics (ISoP), Bellevue, Oct. 23, 2016-Oct. 26, 2016; 2016, 5 pages.

Marks et al., "By-passing Immunization: Human Antibodies from V-gene Libraries Displayed on Phage," J. Mol. Biol., 1991, 222:581-597.

Martin et al., "Irreversible coupling of immunoglobulin fragments to preformed vesicles. An improved method for liposome targeting," J. Biol. Chem., Jan. 10, 1982, 257:286-288.

Mather et al., "Culture of testicular cells in hormone-supplemented serum-free medium," Annals N.Y. Acad. Sci., 1982, 383:44-68.

Mather, Jennie P., "Establishment and characterization of two distinct mouse testicular epithelial cell lines," Biol. Reprod., 1980, 23:243-251.

Morimoto et al., "Single-step purification of F(ab')2 fragments of mouse monoclonal antibodies (immunoglobulins G1) by hydrophobic interaction high performance liquid chromatography using TSKgel Phenyl-5PW," Journal of Biochemical and Biophysical Methods, 1992, 24:107-117.

Morrison et al., "Chimeric human antibody molecules: Mouse antigen-binding domains with human constant region domains"; Proc. Natl. Acad. Sci. USA Nov. 1984, 81:6851-6855.

Nasti et al., "IL-23 Inhibits Melanoma Development by Augmenting DNA Repair and Modulating T-cell Subpopulations," J. Immunol., Jan. 15, 2017, 198(2):950-961.

Neuberger et al., "Recombinant antibodies possessing novel effector functions"; Nature, Dec. 13, 1984, 312:604-608.

Ngiow et al., "A balance of interleukin-12 and -23 in cancer," Trends in Immunology, Nov. 2013, 34(11):548-555.

O'Sullivan et al., "Methods for the Preparation of Enzyme-Antibody Conjugates for use in Enzyme Immunoassay," Methods in Enzymology, 1981, 73:147-166.

Paborsky et al., "Mammalian cell transient expression of tissue factor for the production of antigen," Protein Engineering, 1990, 3(6):547-553.

Papp et al., "Clinical response following re-treatment with a selective IL-23p19 inhibitor risankizumab (BI 655066) or switching from ustekinumab to risankizumab in patients with moderate-to-severe chronic plaque psoriasis," 25th Cong of the European Academy of Dermatology and Venereology (EADV), Vienna, Sep. 28, 2016-Oct. 2, 2016; 2016, 32 pages.

Papp et al., "Comparison of a selective IL-23p19 inhibitor (BI 655066) with ustekinumab in patients with moderate-to-severe plaque psoriasis: analysis of scalp, palmoplantar, and nail psoriasis subgroups," 74th Ann Mtg of the American Academy of Dermatology (AAD), Washington, Mar. 4, 2016-Mar. 8, 2016; 2016, 11 pages.

Papp et al., "Comparison of a selective IL-23p19 inhibitor (BI 655066) with ustekinumab in patients with moderate-to-severe plaque psoriasis: analysis of scalp, palmoplantar, and nail psoriasis subgroups," 74th Ann Mtg of the American Academy of Dermatology (AAD), Washington, Mar. 4, 2016-Mar. 8, 2016; J Am Acad Dermatol; 2016; 74(5)(Suppl 1); Abstr 3433; AB240, 1 page.

Papp et al., "Efficacy and safety of different dose regimens of a novel selective IL-23p19 inhibitor (BI 655066) compared with ustekinumab in patients with moderate-to-severe plaque psoriasis," 73rd Ann Mtg of the American Academy of Dermatology (AAD), San Francisco, Mar. 21, 2015-Mar. 24, 2015; 2015, 59 pages.

Papp et al., "Efficacy and safety of different dose regimens of a selective IL-23p19 inhibitor (BI 655066) compared with ustekinumab in patients with moderate-to-severe plaque psoriasis with and without psoriatic arthritis," ACR/ARHP Sci Mtg 2015, 79th Ann Mtg of the American College of Rheumatology and 50th Ann Mtg of the Association of Rheumatology Health Professionals, San Francisco, Nov. 6, 2015-Nov. 11, 2015; 2015, 22 pages.

Papp et al., "Onset and duration of clinical response following treatment with a selective IL-23p19 inhibitor (BI 655066) compared with ustekinumab in patients with moderate-to-severe chronic plaque psoriasis," 24th Cong of the European Academy of Dermatology and Venereology (EADV), Copenhagen, Oct. 7, 2015-Oct. 11, 2015; 2015, 34 pages.

Papp et al., "Selective blockade of IL-23p19 with BI 655066 is associated with clinical responses superior to ustekinumab in patients with moderate-to-severe plaque psoriasis: results from a 48-week phase II study," 74th Ann Mtg of the American Academy of Dermatology (AAD), Washington, Mar. 4, 2016-Mar. 8, 2016; 2016, 11 pages.

Papp et al., "Selective blockade of IL-23p19 with BI 655066 is associated with clinical responses superior to ustekinumab in patients with moderate-to-severe plaque psoriasis: results from a 48-week phase II study," 74th Ann Mtg of the American Academy of Dermatology (AAD), Washington, Mar. 4, 2016-Mar. 8, 2016; J Am Acad Dermatol; 2016; 74(5)(Suppl 1); Abstr 3362; AB274, 1 page.

Papp et al., "Selective blockade of IL-23p19 with BI 655066 is associated with significant improvement in QoL outcomes compared with ustekinumab in patients with moderate-to-severe plaque psoriasis," 74th Ann Mtg of the American Academy of Dermatology (AAD), Washington, Mar. 4, 2016-Mar. 8, 2016; J Am Acad Dermatol; 2016; 74(5)(Suppl 1); Abstr 2787; AB275, 1 page.

Parham et al., "A Receptor for the Heterodimeric Cytokine IL-23 Is Composed of IL-12R$\beta$1 and a Novel Cytokine Receptor Subunit, IL-23R1," The Journal of Immunology, 2002, 168 :5699-5708.

Pearson et al., "Improved tools for biological sequence comparison," Proc. Natl. Acad. Sci. USA, Apr. 1988, 85:2444-2448.

Plueckthun, A., "Antibodies from *Escherichia coli*," Chapter 11 In The Pharmacology of monoclonal Antibodies, Rosenburg and Moore eds., Springer-Verlag, New York, 1994, 113:269-315.

Reyes et al., "Expression of human $\beta$-interferon cDNA under the control of a thymidine kinase promoter from herpes simplex virus," Nature, Jun. 17, 1982, 297:598-601.

Rudikoff et al., "Single amino acid substitution altering antigen-binding specificity," PNAS, Mar. 1982, 79(6):1979-1983.

Saudek et al., "A preliminary trial of the programmable implantable medication system for insulin delivery," New England Journal of Medicine, Aug. 31, 1989, vol. 321 (pp. 574-579).

Sefton, Michael V., "Implantable Pumps," CRC Crit. Ref. Biomed. Eng., 1989, 14(3): 201-240.

Shopes, B., "A genetically engineered human IgG mutant with enhanced cytolytic activity," J. Immunol., 1992, 148:2918-2922.

Siebert et al., "Why did IL-23p19 inhibition fail in AS: a tale of tissues, trials or translation?", Ann. Rheum. Dis., Aug. 2019, 78(8):1015-1018.

Stevenson et al., "A chimeric antibody with dual Fc regions (bisFabFc) prepared by manipulations at the IgG hinge," Anti-Cancer Drug Design, 1989, 3:219-230.

Stinchcomb et al., "Isolation and characterisation of a yeast chromosomal replicator," Nature, Nov. 1, 1979, 282:39-43.

Thotakura et al., "Enzymatic deglycosylation of glycoproteins," Meth, Enzymol, 1987, 138:350-359.

Torelli et al., "ADVANCE and ADAM: two algorithms for the analysis of global similarity between homologous informational sequences," Comput. Appl. Biosci., 1994, 10(1):3-6.

Urlaub et al., "Isolation of Chinese hamster cell mutants deficient in dihydrofolate reductase activity," Proc. Natl. Acad. Sci. USA, Jul. 1980, 77, 4216-4220.

Van den Berg et al., "Kluyveromyces as a Host for Heterologous Gene Expression: Expression and Secretion of Prochymosin," Bio/Technology, Feb. 1990, 8:135-139.

Visvanathan et al., "IL-23 pathway inhibition by risankizumab differentially modulates the molecular and histopathological profile in psoriatic skin compared with ustekinumab," 25th Cong of the European Academy of Dermatology and Venereology (EADV), Vienna, Sep. 28, 2016-Oct. 2, 2016; 2016, 12 pages.

Visvanathan et al., "Selective IL-23 inhibition by risankizumab modulates the molecular profile in the colon of active Crohn's

(56)        References Cited

OTHER PUBLICATIONS disease patients," 24th United Eur Gastroenterology Week (UEGW), Vienna, Oct. 15, 2016-Oct. 19, 2016; 2016, 11 pages.

Vitetta et al., "Redesigning nature's poisons to create anti-tumor reagents," Science, Nov. 20, 1987, 238:1098-1104.

Wang et al., "Instability, stabilization, and formulation of liquid protein pharmaceuticals," International Journal of Pharmaceutics, 1999, 185(2):129-188.

Wolff et al., "Monoclonal Antibody Homodimers: Enhanced Anti-tumor Activity in Nude Mice," Cancer Research, Jun. 1, 1993, 53:2560-2565.

Yaniv, Moshe, "Enhancing elements for activation of eukaryotic promoters," Nature, May 6, 1982, 297:17-18.

Yao et al., "Inhibition of the interleukin-23/interleukin-17 pathway by anti-interleukin-23p19 monoclonal antibody attenuates 2,4,6-trinitrobenzene sulfonic acid-induced Crohn’s disease in rats," Molecular Medicine Reports, 2014, 10:2105-2110.

Zapata et al., "Engineering linear F(ab')2 fragments for efficient production in *Escherichia coli* and enhanced antiproliferative activity," Protein Engineering, 1995, 8(10):1057-1062.

Zola, Heddy, "Using Monoclonal Antibodies: Soluble Antigens," Chapter 6 in Monoclonal Antibodies: A Manual of Techniques, 1987, CRC Press, 147-181.

Carron, et al., "Peripheral manifestations in spondyloarthritis: relevance for diagnosis, classification and follow-up," Curr. Opin. Rheumatol., 2012, 24:370-374.

Dauden et al., "Ustekinumab: effective in a patient with severe recalcitrant generalized pustular psoriasis," British Journal of Dermatology, Dec. 2010, 163(6):1346-1347.

Huang, et al., "The DAVID Gene Functional Classification Tool: a novel biological module-centric algorithm to functionally analyze large gene lists," Genome Biology 2007, 8:R183 (16 pages).

Iezzi, et al., "CD40-CD40L cross-talk integrates strong antigenic signals and microbial stimuli to induce development of IL-17-producing CD4 T cells," Proc Natl Acad Sci U S A., 2009 106:876-81.

Marrakchi et al., "Pathophysiology of Generalized Pustular Psoriasis," American Journal of Clinical Dermatology, Jan. 21, 2022, 23(Suppl. 1):S13-S19.

Massey, R.J., "Catalytic antibodies catching on," Nature 1987, 328:457-458.

Myers, et al., "Approximate matching of regular expressions," Bulletin of mathematical biology vol. 51, 1, (1989): 5-37.

Stella, et al., (1985). "Prodrugs: A Chemical Approach to Targeted Drug Delivery." In: Borchardt, et al., (eds.) Directed Drug Delivery. Experimental Biology and Medicine, vol. 7. Humana Press. https://doi.org/10.1007/978-1-4612-5186-6_14 (Abstract only).

Wilman, (1986), "Prodrugs in Cancer Chemotherapy," In Biochemical Society Transactions, 14, pp. 375-382, 615th Meeting Belfast (Preview Only).

Haugh et al., "Risankizumab: an anti-IL-23 antibody for the treatment of psoriasis," Drug Design, Development and Therapy, 2018, 12:3879-3883.

Langley et al., "The 5-point Investigator's Global Assessment (IGA) Scale: A modified tool for evaluating plaque psoriasis severity in clinical trials," Journal of Dermatological Treatment, 2015, 26(1):23-31.

Pubchem, Bethesda (MD): National Library of Medicine (US), National Center for Biotechnology Information, Oct. 12, 2023, PubChem Compound Summary for Risankizumab, Registry No. 1612838-76-2, https://pubchem.ncbi.nlm.nih.gov/compound/Risankizumab, 14 pages.

Rayaprolu et al., "Excipients in parenteral formulations: selection considerations and effective utilization with small molecules and biologics," Drug Development and Industrial Pharmacy, 2018, 44(10):1565-1571.

* cited by examiner

FIG 1

Light chain amino acid sequence

DIQMTQSPSS LSASVGDRVT ITCKASRDVA IAVAWYQQKP GKVPKLLIYW ASTRHTGVPS RFSGSGSRTD

FTLTISSLQP EDVADYFCHQ YSSYPFTFGS GTKLEIKRTV AAPSVFIFPP SDEQLKSGTA SVVCLLNNFYP

REAKVQWKV DNALQSGNSQ ESVTEQDSKD STYSLSSTLT LSKADYEKHK VYACEVTHQG LSSPVTKSFN

RGEC (SEQ ID NO: 1)

FIG 2

Heavy chain amino acid sequence

QVQLVQSGAEVKKPGSSVKVSCKASGYTFTDQTIHWMRQAPGQGLEWIGYIYPRDDSPKYNENFKGKVTITADK

STSTAYMELSSLRSEDTAVYYCAIPDRSGYAWFIYWGQGTLVTVSSASTKGPSVFPLAPSSKSTSGGTAALGCL

VKDYFPEPVTVSWNSGALTSGVHTFPAVLQSSGLYSLSSVVTVPSSSLGTQTYICNVNHKPSNTKVDKRVEPKS

CDKTHTCPPCPAPEAAGGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRWQQGNVFSCSVMHEALHNHYTQKSL

SLSPG (SEQ ID NO: 2)

FIG 3

| Aim | Week 1 | | | | | | | Week 2 | | | | | | | Week 3 | | | | | | | Week 4 | | | | | | |
|---|---|---|---|---|---|---|---|---|---|---|---|---|---|---|---|---|---|---|---|---|---|---|---|---|---|---|---|---|
| | M | T | W | T | F | S | S | M | T | W | T | F | S | S | M | T | W | T | F | S | S | M | T | W | T | F | S | S |
| 6 freeze/thaw cycles | *1* | *1* | *2* | *2* | *3* | *3* | *4* | *4* | *5* | *5* | *6* | | | | | | | | | | | 6 | | | | | | |
| 3 freeze/thaw cycles | | | | | | | | *1* | *1* | *2* | *2* | *3* | | | | | | | | | | 3 Analyses | | | | | | |
| 1 freeze/thaw cycle | | | | | | | | | | | | | | | | | | | | | *1* | 1 | | | | | | |
| reference stored at 2-8°C | | | | | | | | | | | | | | | | | | | | | | | | | | | | | store at 2-8°C as reference →

*italicized: freeze;* bolded: thaw

ANTI-IL-23p19 ANTIBODY FORMULATIONS

CROSS-REFERENCE TO RELATED APPLICATION

This application claims priority from U.S. Provisional Application No. 62/897,930, filed Sep. 9, 2019, the entire contents of which are incorporated herein.

The instant application contains a Sequence Listing which has been submitted in ASCII format via EFS-WEB and is hereby incorporated by reference in its entirety. Said ASCII copy, created on Sep. 8, 2020 is named sequence.txt and is 5,909 bytes.

FIELD OF THE DISCLOSURE

This invention generally relates to formulations comprising anti-IL-23p19 antibodies, such as risankizumab, which bind the p19 subunit of human IL-23. More specifically, pharmaceutical formulations comprising a high concentration of the anti-IL-23p19 antibody risankizumab, as well as related products and uses for the treatment of various diseases and disorders, are disclosed. Disclosed herein are stable liquid pharmaceutical formulations, comprising 150 mg/ml of the antibody risankizumab.

BACKGROUND

Human IL-23 is composed of a common subunit (p40) with IL-12 and a unique p19 subunit. Despite this shared p40 subunit, the roles for IL-23 and IL-12 are quite different. IL-12 is important for Th1 responses via promotion of Th1 cell differentiation, proliferation and activation. In contrast, IL-23 supports the development and maintenance of a set of CD4+T helper cells termed Th17 cells due to their ability to produce IL-17 and related cytokines. IL-23 is involved in chronic autoimmune inflammation and the modulation of IL-23 activity provides effective therapies against autoimmune diseases.

One of the autoimmune diseases where IL-23 plays a central role is psoriasis, a chronic, immune-mediated inflammatory disease characterized by the hyper proliferation of keratinocytes and skin-infiltrating T-lymphocytes that over-express pro-inflammatory mediators. The disease is a chronic, painful immune-mediated inflammatory skin disease and has a lifelong remitting and relapsing course with varying factors that trigger exacerbations in susceptible individuals, thus making treatment challenging. The uncontrolled inflammation of psoriasis may contribute to commonly associated comorbidities, including cardiovascular (CV) disease (including hypertension and increased risk for myocardial infarction, stroke, and CV death), obesity, type 2 diabetes, arthritis, and chronic renal disease. Psoriasis is also associated with serious psychiatric comorbidities, including depression, anxiety, and suicidality, as well as substance abuse.

A highly efficient and specific inhibitor of IL-23 is the antibody risankizumab. Risankizumab is a humanized immunoglobulin G1 (IgG1) monoclonal antibody that is directed against the p19 subunit of IL-23. Binding of risankizumab to IL-23 p19 inhibits the action of IL-23 to induce and sustain T helper (Th) 17 type cells, innate lymphoid cells, γ&T cells, and natural killer (NK) cells responsible for tissue inflammation, destruction and aberrant tissue repair. Risankizumab is especially effective in the treatment of autoimmune and inflammatory diseases, in particular psoriasis. Clinical studies revealed excellent safety and efficacy of risankizumab in the treatment of plaque psoriasis. The recommended dose approved for treatment of psoriasis is 150 mg which is administered subcutaneously as two 75 mg injections, on week 0, 4 and thereafter every 12 weeks.

The requirement for injection of larger medicament volumes presents a challenge, especially in patients with chronic conditions who have markedly lower rates of drug adherence and persistence than patients with acute conditions. Administration by subcutaneous route is preferred for therapeutic indications where home (self) medication is desirable, for example, for chronic diseases such as psoriasis. The subcutaneous administration route is, however, limited by the injection volume as attributable to tissue backpressure and injection pain. This also depends on the injected formulation. Most drugs that are administered by subcutaneous injection, such as risankizumab, are commonly used in unit dosages with volumes not exceeding 1 ml. Therefore, for higher volumes, such as greater than 2 ml, multiple injections are typically used, but this approach may increase the attrition rate or reduce patient adherence.

Therefore, to allow the administration of a high dose of antibody such as risankizumab with a single injection, there is a need for pharmaceutical formulations with increased antibody concentration. However, increasing the antibody concentration in antibody formulations can cause problems with stability, e.g. aggregation resulting in the formation of high molecular weight species (HMWS) and increased viscosity. Therefore, it is a great challenge to provide a stable high concentration liquid antibody formulation that is suitable for parenteral administration, such as subcutaneous injection.

SUMMARY

The present disclosure provides a liquid antibody formulation that comprises 150 mg/ml of the antibody as defined herein. The antibody is risankizumab or an antibody comprising the same heavy and light chain sequences as risankizumab. No formulations of said antibody having such a high antibody concentration were described or available in the art and by providing such high concentration antibody formulation, the present disclosure makes an important contribution to the art. Despite the high antibody concentration, the formulations according to the present disclosure are stable and are suitable for therapeutic use. As is demonstrated in the examples, the formulations according to the present disclosure comprising 150 mg/ml of the antibody risankizumab provide advantageous stability characteristics and are well suitable for subcutaneous administration. They can provide long-term stability. Advantageously, a 150 mg dose of the antibody can be administered with a single 1 ml injection.

According to a first aspect of the present disclosure, a liquid pharmaceutical formulation is provided comprising 150 mg/ml of an anti-IL-23p19 antibody, wherein the antibody comprises a light chain amino acid sequence according to SEQ ID NO: 1 and a heavy chain amino acid sequence according to SEQ ID NO: 2.

According to a first sub-aspect of this first aspect, the liquid pharmaceutical formulation comprises
- a) 150 mg/ml of an anti-IL-23p19 antibody, wherein the antibody comprises a light chain amino acid sequence according to SEQ ID NO: 1 and a heavy chain amino acid sequence according to SEQ ID NO: 2;
- b) a polyol; and
- c) a surfactant.

This formulation may additionally comprise d) a buffer. Furthermore, the present disclosure provides buffer-free formulations comprising 150 mg/ml of the antibody. As is disclosed herein, the liquid pharmaceutical formulations according to the first sub-aspect are stable.

According to a second sub-aspect of this first aspect, a stable liquid pharmaceutical formulation is provided comprising a) 150 mg/ml of an anti-IL-23p19 antibody, wherein the antibody comprises a light chain amino acid sequence according to SEQ. ID NO: 1 and a heavy chain amino acid sequence according to SEQ ID NO: 2;

b) a tonicity modifier; and c) a surfactant, wherein the formulation has a pH of 5.5-5.9 and the formulation is isotonic.

This formulation may additionally comprise d) a buffer.

The formulations according to the first and second sub-aspect of the 150 mg/ml antibody formulation according to the first aspect may also be provided in lyophilized form.

In related aspects, a sealed container is provided which contains a formulation according to the present disclosure.

In related aspects, the present disclosure pertains to the formulations according to the present disclosure or the container containing a formulation according to the present disclosure for therapeutic treatment of a human subject. The disease to be treated may be selected from psoriasis and inflammatory bowel disease. In further embodiments, the disease to be treated may be selected from psoriatic arthritis and Crohn's disease.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only.

BRIEF DESCRIPTION OF THE FIGURES

FIG. 1 shows the amino acid sequence of the light chain of the antibody (SEQ ID NO: 1).

FIG. 2 shows the amino acid sequence of the heavy chain of the antibody (SEQ ID NO: 2).

FIG. 3 shows an overview of the experimental schedule used to assess freeze-thaw stability of various formulations.

DETAILED DESCRIPTION

150 Mg/Ml Antibody Formulation and Related Aspects

According to a first aspect, a liquid pharmaceutical formulation is provided comprising 150 mg/ml of an anti-IL-23p19 antibody, wherein the antibody comprises a light chain amino acid sequence according to SEQ ID NO: 1 and a heavy chain amino acid sequence according to SEQ ID NO: 2.

According to a first sub-aspect of this first aspect, a liquid pharmaceutical formulation is provided comprising a) 150 mg/ml of an anti-IL-23p19 antibody, wherein the antibody comprises a light chain amino acid sequence according to SEQ ID NO: 1 and a heavy chain amino acid sequence according to SEQ ID NO: 2;

b) a polyol; and c) a surfactant.

The formulation according to this first sub-aspect may additionally comprise d) a buffer. Furthermore, the present disclosure provides buffer-free formulations comprising 150 mg/ml of the antibody. As is disclosed herein, the liquid pharmaceutical formulations according to the first sub-aspect are stable.

According to a second sub-aspect of this first aspect, a stable liquid pharmaceutical formulation is provided comprising a) 150 mg/ml of an anti-IL-23p19 antibody, wherein the antibody comprises a light chain amino acid sequence according to SEQ ID NO: 1 and a heavy chain amino acid sequence according to SEQ ID NO: 2;

b) a tonicity modifier; and c) a surfactant, wherein the formulation has a pH of 5.5-5.9 and the formulation is isotonic.

The stable formulation according to this second sub-aspect may additionally comprise d) a buffer.

The formulation according to the present disclosure comprises a high antibody concentration of 150 mg/ml. Despite this high antibody concentration, the liquid pharmaceutical formulations of the present disclosure are stable and advantageously can provide long-term stability. The formulations according to the present disclosure moreover address core administration challenges for a high concentration antibody formulation that is suitable for injection, by providing inter alia a suitable viscosity and good syringeability, whereby the formulation according to the present disclosure is particularly suitable for injection, such as subcutaneous injection. The advantageous properties of these formulations are demonstrated in the examples. The formulation according to the first aspect solves the challenges facing formulations for injection by providing a stable and robust formulation comprising 150 mg/ml of the antibody, thereby enabling the subcutaneous administration of a 150 mg dose of the antibody using a target volume of only 1 ml.

As disclosed herein, the formulations according to the first aspect can be provided as buffer-free or buffer-containing formulations. According to one core embodiment, the liquid pharmaceutical formulation according to the first aspect comprises d) a buffer. In another embodiment, the liquid pharmaceutical formulation does not contain a buffer as additive.

Subsequently, the components of the 150 mg/ml antibody formulation according to the first aspect are described in further detail. In particular, suitable embodiments and characteristics of components a), b), c) and optionally d) that are comprised in the formulations according to the first sub-aspect and the second sub-aspect are disclosed.

a) the Antibody

The antibody comprised in the formulation comprises a light chain amino acid sequence according to SEQ ID NO: 1 and a heavy chain amino acid sequence according to SEQ ID NO: 2. SEQ ID NO: 1 and 2 are shown in FIG. 1 and FIG. 2. The light and heavy chains of the antibody risankizumab correspond to the light and heavy chain sequences as shown in SEQ ID NO: 1 and 2. According to one embodiment, the antibody has the same light and heavy chains as the antibody risankizumab (see INN risankizumab, WHO Drug Information, Vol. 29, No. 2, 2015) and such antibody is referred to herein as risankizumab. Advantageously, the present disclosure provides stable, high concentration liquid pharmaceutical formulations for the antibody risankizumab, which is approved for the treatment of psoriasis. The whole disclosure provided herein, is specifically directed and applies to the antibody risankizumab that is comprised in the disclosed formulations. Risankizumab may be recombinantly produced in various host cells and suitable cells for recombinant antibody production are known in the art.

In one embodiment, the antibody is recombinantly produced in a mammalian cell. Suitable mammalian cells are known in the art and comprise rodent as well as human cell lines. In one embodiment, the antibody has been recombinantly produced in a hamster cell. In one embodiment, the antibody has been recombinantly produced in a CHO cell.

Component b)

The formulation according to the first sub-aspect of the 150 mg/ml formulation according to the first aspect comprises a polyol as component b). Suitable polyols that can be used as excipient in a pharmaceutical formulation are known in the art and are described herein.

The formulation according to the second sub-aspect of the 150 mg/ml formulation according to the first aspect comprises a tonicity modifier as component b). A tonicity modifier is an agent that is suitable to adjust the tonicity of the formulation. Tonicity modifiers useful for adjusting the tonicity of a pharmaceutical formulation are known in the art, and include compounds such as salts and furthermore polyols, such as sugars and sugar alcohols. Therefore, the tonicity modifier used as component b) in the stable 150 mg/ml formulation according to the second sub-aspect may be a polyol as it is used as component b) in the 150 mg/ml formulation according to the first sub-aspect. According to one embodiment, the tonicity modifier that is comprised in the stable liquid formulation according to the second sub-aspect is thus a polyol, optionally a sugar and/or a sugar alcohol.

The term "polyol" as used herein refers to a substance with multiple hydroxyl groups, and includes sugars (reducing and nonreducing sugars) and sugar alcohols. The polyol may comprise at least three, at least four or at least five hydroxyl groups. In certain embodiments, polyols have a molecular weight that is ≤600 Da (e.g., in the range from 120 to 400 Da). A "reducing sugar" is one that contains a free aldehyde or ketone group and can reduce metal ions or react covalently with lysine and other amino groups in proteins. A "nonreducing sugar" is one that lacks a free aldehyde or ketone group and is not oxidised by mild oxidising agents such as Fehling's or Benedict's solutions. Examples for reducing and nonreducing sugars suitable for use in pharmaceutical formulations are known to the skilled person. Nonreducing sugars include e.g. sucrose and trehalose. The use of trehalose is particularly useful as is disclosed herein. Examples of sugar alcohols suitable for use in pharmaceutical formulations are known to the skilled person and include e.g. mannitol and sorbitol. The polyol may be used as tonicity agent in the formulation.

A polyol can act and may be used as tonicity modifier in order to adjust the tonicity. Certain polyols, e.g. sugars, may also act as stabilizer, thereby supporting the stability of the provided formulation.

As disclosed herein, the polyol may be selected from a sugar and a sugar alcohol. Furthermore, combinations of two or more different polyols may be used as component b), as is also demonstrated in the examples. As is shown in the examples, sugars and sugar alcohols, as well as combinations thereof, can be advantageously used in the 150 mg/ml formulation according to the present disclosure. According to one embodiment, the polyol is selected from trehalose, sucrose, sorbitol, mannitol and combinations thereof. According to one embodiment, the formulation only comprises a polyol that is selected from sugars and/or sugar alcohols as component b). According to one embodiment, the formulation only comprises a single polyol as component b).

In specific embodiments, the polyol is a sugar. The polyol may be selected from trehalose and sucrose. As is shown in the examples, the formulation may comprise trehalose as polyol and the use of trehalose is advantageous. Trehalose can be used either alone or in combination with a further polyol, e.g. a further sugar or a sugar alcohol. According to specific embodiments, the formulation only comprises a single sugar, such as trehalose, as single polyol. Using a single polyol as excipient, e.g. to adjust the tonicity, can be advantageous.

According to one embodiment, the polyol is a sugar alcohol. The sugar alcohol may be selected from sorbitol and mannitol. In embodiments, the formulation comprises mannitol as polyol. In further embodiments, the formulation comprises sorbitol. As disclosed herein, mannitol and sorbitol may either be used as single polyol, or may be used in combination either with each other or in combination with a different polyol, such as a sugar or other sugar alcohol.

Sorbitol can be used to provide a stable formulation according to the present disclosure. In certain embodiments, a sorbitol-free formulation is provided. Sorbitol-free formulations are advantageous for patients with hereditary fructose intolerance. In a specific embodiment, the liquid pharmaceutical formulation therefore does not comprise sorbitol. In certain embodiments, the formulation does not comprise a sugar alcohol.

As is demonstrated in the examples, mannitol and/or trehalose can be used as polyol in the formulation of the present disclosure, in order to adjust the desired osmolality. However, the amount of mannitol within the 150 mg/ml formulation is limited by the mannitol solubility and the amount of stock solution, which can be added during the formulation step. Therefore, in embodiments, mannitol is used in combination with a sugar, such as the highly soluble trehalose. It was found that for the antibody formulation disclosed herein, trehalose is advantageous because it is soluble enough to achieve an isotonic formulation with one excipient. Therefore, in certain embodiments, trehalose is used as polyol and trehalose may be the only polyol in the formulation that is used to adjust the isotonicity.

The polyol can be used to adjust the osmolality. In embodiments, the formulation has an osmolality in a range of 200 mOsm/kg to 400 mOsm/kg, such as in a range of 225 mOsm/kg to 375 mOsm/kg. In embodiments, the osmolality is within a range of 250 mOsm/kg to 350 mOsm/kg, such as 275 mOsm/kg to 330 mOsm/kg or 290 mOsm/kg to 320 mOsm/kg. The formulation may be isotonic, wherein "isotonic" means that the formulation of interest has essentially the same osmotic pressure as human blood. Osmolality can be measured, for example, using a vapor pressure or ice-freezing type osmometer.

The concentration of the polyol in the formulation may be at least 80 mM or at least 95 mM. In embodiments, the concentration of the polyol in the formulation is at least 115 mM, at least 125 mM, at least 135 mM, at least 140 mM, at least 150 mM or at least 160 mM. In embodiments, the concentration of the polyol in the formulation is ≤500 mM, ≤450 mM or ≤400 mM. As disclosed herein, also two or more polyols may be used as excipient b). As disclosed herein, in one core embodiment the polyol is a sugar that is used in such concentration. In one embodiment, the sugar is trehalose. The same applies with respect to the tonicity modifier that is used as component b) in the formulation according to the second sub-aspect. As disclosed herein, the tonicity modifier may be a polyol.

The concentration of the polyol in the formulation according to the first aspect, in particular the first and second sub-aspect thereof, may be in the range of 95 mM to 400 mM, such as 95 mM to 300 mM or 95 mM to 250 mM. Exemplary concentration ranges for a polyol in the formulation include, but are not limited to, 125 mM to 250 mM and 125 mM to 225 mM. The concentration of the polyol in the formulation is in one embodiment in the range of 125 mM to 225 mM. In one embodiment, the concentration of the polyol is in the range of 145 mM to 225 mM. As disclosed herein, in one core embodiment the polyol is a sugar that is used in such a concentration as described herein. In one embodiment, the sugar is trehalose.

According to one embodiment, the polyol is a sugar and wherein the concentration of the sugar is in the range of 125 mM to 250 mM, 150 mM to 250 mM, 150 mM to 200 mM or in the range of 160 mM to 200 mM. In a further embodiment, the concentration of the sugar is in the range of 170 mM to 200 mM. The concentration may be 185 mM. In one embodiment, said sugar is trehalose. Hence, also disclosed herein is a liquid pharmaceutical formulation comprising 150 mg/ml antibody and 185 mM trehalose as polyol. Trehalose may be added e.g. in the form of trehalose dihydrate.

c) Surfactant

The liquid formulation according to the first aspect further comprises a surfactant. As is demonstrated by the examples, incorporating a surfactant in the 150 mg/ml formulation is advantageous. A surfactant is comprised as component c) in the formulation according to the first and second sub-aspect of the 150 mg/ml formulation according to the first aspect.

According to one embodiment, the surfactant is a non-ionic surfactant. Non-ionic surfactants suitable for pharmaceutical formulations are known in the art and are also described herein. The at least one surfactant may be a polysorbate (e.g. polysorbate 20) or a poloxamer (e.g. poloxamer 188). Combinations of surfactants may also be used. In one core embodiment, the surfactant is a polysorbate. The non-ionic surfactant may be selected from polysorbate 20 and/or polysorbate 80. Combinations may also be used. In one embodiment, the surfactant is polysorbate 20. In one embodiment, the formulation according to the present disclosure comprises a single surfactant, such as a single non-ionic surfactant, e.g. a single polysorbate.

In one embodiment, the concentration of the surfactant in the formulation is at least 0.05 mg/ml. The concentration may be at least 0.075 mg/ml. As is demonstrated in the examples, even low amounts of a surfactant provide a benefit. In embodiments, the surfactant concentration in the formulation is at least 0.1 mg/ml, at least 0.125 mg/ml, at least 0.15 mg/ml, at least 0.175 mg/ml or at least 0.185 mg/ml. In embodiments, the concentration of the surfactant in the formulation is ≤1 mg/ml, optionally≤0.75 mg/ml or ≤0.5 mg/ml. In embodiments, the surfactant concentration in the formulation is ≤0.4 mg/ml, ≤0.3 mg/ml or ≤0.25 mg/ml. As disclosed herein, the surfactant may be a non-ionic surfactant. As disclosed herein, in core embodiments the surfactant is a polysorbate, optionally selected from polysorbate 20 and/or polysorbate 80. In embodiments, the surfactant is polysorbate 20. Polysorbate 20 can be advantageously used in such concentrations as disclosed herein as is demonstrated by the examples.

The concentration of the surfactant in the formulation may be in a range of 0.05 mg/ml to 0.75 mg/ml. Exemplary concentration ranges for a surfactant in the formulation include, but are not limited to, 0.05 mg/ml to 0.5 mg/ml, 0.075 mg/ml to 0.4 mg/ml or 0.075 mg/ml to 0.3 mg/ml. In embodiments, the concentration of the surfactant in the formulation is in the range of 0.05 mg/ml to 0.5 mg/ml, 0.075 mg/ml to 0.3 mg/ml or 0.1 mg/ml to 0.3 mg/ml. The concentration of the surfactant in the formulation may be 0.2 mg/ml. As is disclosed herein, the surfactant may be a non-ionic surfactant. In core embodiments the surfactant is a polysorbate, optionally selected from polysorbate 20 and/or polysorbate 80. In embodiments, the surfactant is polysorbate 20 which can be advantageously used in such concentration ranges as is demonstrated by the examples.

In specific embodiments, the formulation of the present disclosure comprises 0.2 mg/ml polysorbate 20 as surfactant. This formulation may comprise a sugar as component b), wherein the concentration of the sugar is in the range of 95 mM to 250 mM, 125 mM to 250 mM or 145 mM to 225 mM. The comprised sugar may be trehalose.

pH

The pH of the liquid pharmaceutical formulation, which in core embodiments is an aqueous formulation, may be in the range of pH 5.0 to 7.5, such as pH 5.0 to 7.0.

The pH of the liquid pharmaceutical formulation may be ≤6.8, such as ≤6.7, ≤6.6, ≤6.5, ≤6.4, ≤6.3 or ≤6.2. In embodiments, the pH of the liquid pharmaceutical formulation is ≤6.1, such as ≤6.0 or ≤5.9. In embodiments, the pH of the liquid pharmaceutical formulation is ≥5.2, such as ≥5.3, ≥5.4 or ≥5.5. Exemplary ranges for the pH of the liquid pharmaceutical formulation which has a pH≥5.2 include but are not limited to 5.2 to 6.8, such as 5.2 to 6.7, 5.2 to 6.6, 5.2 to 6.5, 5.2 to 6.4, 5.2 to 6.3 and 5.2 to 6.2. Exemplary ranges for the pH of the liquid pharmaceutical formulation which has a pH≥5.3 include but are not limited to 5.3 to 6.8, such as 5.3 to 6.7, 5.3 to 6.6, 5.3 to 6.5, 5.3 to 6.4, 5.3 to 6.3 and 5.3 to 6.2. Exemplary ranges for the pH of a liquid pharmaceutical formulation which has a pH≥5.4 include but are not limited to 5.4 to 6.8, such as 5.4 to 6.7, 5.4 to 6.6, 5.4 to 6.5, 5.4 to 6.4, 5.4 to 6.3 and 5.4 to 6.2. Exemplary ranges for the pH of the liquid pharmaceutical formulation which has a pH≥5.5 include but are not limited to 5.5 to 6.8, such as 5.5 to 6.7, 5.5 to 6.6, 5.5 to 6.5, 5.5 to 6.4, 5.5 to 6.3 and 5.5 to 6.2. Exemplary ranges for the pH of the liquid pharmaceutical formulation which has a pH≥5.6 include but are not limited to 5.6 to 6.8, such as 5.6 to 6.7, 5.6 to 6.6, 5.6 to 6.5, 5.6 to 6.4, 5.6 to 6.3 and 5.6 to 6.2. In further embodiments the pH of the formulation is in a range of 5.6 to 6.0 or 5.6 to 5.9.

According to one embodiment, the pH of the liquid pharmaceutical formulation is in the range of 5.2 to 6.5. According to one embodiment, the pH of the liquid pharmaceutical formulation is in the range of 5.2 to 6.2. Lower pH values showed less aggregation during stability and physical stress studies as can be seen from the examples.

According to one embodiment, the pH of the liquid pharmaceutical formulation is in the range of 5.5 to 6.5. In one embodiment, the pH of the liquid pharmaceutical formulation is in a range of 5.5 to 6.2.

According to one embodiment, the pH is 5.5 to 5.9. In one embodiment, the pH is 5.6 to 5.8. 150 mg/ml risankizumab formulations having such pH were tested in the examples and showed favorable characteristics.

In a further embodiment, the pH of the liquid pharmaceutical formulation is 5.7.

In a further embodiment, the pH of the liquid pharmaceutical formulation is 6.2.

As disclosed herein, the pH of the stable liquid pharmaceutical formulation according to the second sub-aspect is 5.5 to 5.9. It may be in the range of 5.5 to 5.8. In embodiments, the pH of the stable 150 mg/ml formulation according to the second sub-aspect is 5.7.

d) Buffer

The 150 mg/ml antibody formulation according to the first aspect can be provided as buffer-free or as buffer-containing formulation. According to one core embodiment disclosed herein, the pharmaceutical formulation comprises d) a buffer. Formulations comprising a buffer showed in experiments less increase in glide forces (max and average) compared to buffer-free formulations. Accordingly, a buffer may be used as component d) in the formulation according to the first and second sub-aspect of the 150 mg/ml risankizumab formulation according to the first aspect.

A buffer can be used to maintain the solution pH of the liquid pharmaceutical formulation. Suitable buffers for pharmaceutical formulations are known in the art and are described herein. The buffer may be an organic buffer. According to one embodiment, the buffer has a pKa within 1.5 or 1 pH unit of the final pH of the liquid pharmaceutical formulation at 25° C. In certain embodiments, the buffer has a pKa in the range of pH 4.2 to 7.2 or 4.5 to 7 at 25° C. The buffer may comprise a combination of buffers. In one embodiment, a single buffer is used in the formulation as component d).

The formulation may comprise a carboxylic acid buffer as buffer d).

According to one embodiment, the buffer is selected from an acetate buffer and a succinate buffer. As is demonstrated by the examples, formulations comprising such buffers provide advantageous stability features for the high concentration formulation of the antibody that is herewith provided. In further embodiments, the buffer is a histidine buffer.

In one embodiment, the buffer is an acetate buffer. An acetate buffer may comprise sodium acetate and acetic acid. Other acetate salts may also be used in the acetate buffer.

Further buffers that may be used include but are not limited to citrate, glutamate, glycine, lactate, maleate, phosphate or tartrate buffer.

The presence of a buffer salt may support the stability of the comprised antibody which is according to the present disclosure risankizumab.

According to one embodiment, the buffer d) comprised in the formulation is not a succinate buffer. In certain embodiments, the formulation is free of a succinate buffer. In certain embodiments, a single buffer is used which is an acetate buffer, e.g. provided by an acetate salt (e.g. sodium acetate) and acetic acid.

When used, the buffer will be included in a sufficient amount to maintain the selected pH of the formulation at storage conditions for the product shelf life.

The liquid pharmaceutical formulation disclosed herein may comprise at least 1 mM, at least 2 mM buffer, at least 3 mM buffer. The buffer concentration may be at least 4 mM, at least 4.5 mM or at least 5 mM. In embodiments, the buffer concentration is 100 mM or less, such as 75 mM or less or 50 mM or less. In embodiments, the buffer concentration in the formulation is 80 mM or less, such as 75 mM or less, 70 mM or less, 60 mM or less or 50 mM or less. In further embodiments, the buffer concentration is 45 mM or less, such as 40 mM or less, 35 mM or less, 30 mM or less or 25 mM or less. In further embodiments, the buffer concentration is 20 mM or less or 15 mM or less. Exemplary concentration ranges for the comprised buffer include but are not limited to 3 mM to 100 mM, such as 4 mM to 75 mM, 4 mM to 60 mM and 4 mM to 50 mM. Further exemplary buffer concentration ranges include but are not limited to 4 mM to 45 mM, such as 5 mM to 40 mM, 5 mM to 35 mM and 5 mM to 30 mM. Still further exemplary buffer concentration ranges include but are not limited to 5 mM to 25 mM, such as 5 mM to 20 mM and 5 mM to 15 mM. In one specific embodiment, the buffer concentration is in the range of 7 mM to 12 mM. Suitable buffers are disclosed herein. In one embodiment, the formulation comprises an acetate buffer in such concentration as described.

In embodiments, the buffer concentration is 20 mM or less or 15 mM or less. In further embodiments the buffer concentration is in the range of 4 mM to 50 mM. The buffer concentration of the formulation may be in the range of 5 mM to 25 mM or 5 mM to 20 mM. The buffer concentration may also be in the range of 5 mM to 15 mM or 7 mM to 12 mM. In embodiments, the buffer concentration is 10 mM.

In certain embodiments, the formulation comprises a single buffer. In specific embodiments the single buffer is an acetate buffer.

Specific Embodiments for Buffer-Containing Formulations Comprising 150 mg/Ml Antibody According to one embodiment, the liquid pharmaceutical formulation comprises a) 150 mg/ml of the antibody;
b) a sugar;
c) a non-ionic surfactant; and
d) a buffer;
optionally wherein the pH of the formulation is in a range of pH 5.2 to pH 6.5, e.g. in the range of 5.2 to 6.2 or 5.5 to 6.2.

Suitable concentrations and embodiments for the excipients b) to d) were described above. In one embodiment, the concentration of the sugar is in the range of 145 mM to 225 mM and/or the concentration of the non-ionic surfactant is in the range of 0.05 mg/ml to 0.5 mg/ml or 0.075 mg/ml to 0.3 mg/ml. The sugar may be trehalose and the non-ionic surfactant may be a polysorbate, such as polysorbate 20. The pH may be 5.7. In a further embodiment the pH is 6.2.

According to one embodiment, the liquid pharmaceutical formulation comprises a) 150 mg/ml of the antibody;
b) trehalose;
c) a polysorbate; and
d) a buffer;
optionally wherein the pH of the formulation is in a range of pH 5.2 to pH 6.5, e.g. in the range of 5.2 to 6.2 or 5.5 to 6.2.

Suitable concentrations and embodiments for the excipients b) to d) were described above. In one embodiment, the concentration of trehalose is in the range of 145 mM to 225 mM and/or the concentration of the polysorbate is in the range of 0.05 mg/ml to 0.5 mg/ml or 0.075 mg/ml to 0.3 mg/ml. The pH may be 5.7. In a further embodiment the pH is 6.2.

The buffer comprised in these liquid pharmaceutical formulations may be acetate or succinate, optionally wherein the buffer concentration is in the range of 5 mM to 25 mM. The polysorbate may be polysorbate 20.

According to one embodiment, the liquid pharmaceutical formulation comprises a) 150 mg/ml of the antibody;
b) 170 mM to 200 mM trehalose;
c) 0.1 mg/ml to 0.3 mg/ml polysorbate, optionally polysorbate 20; and
d) a buffer, optionally wherein the buffer is an acetate buffer.

The pH of this formulation may be in a range of pH 5.2 to pH 6.5, e.g. in the range of 5.2 to 6.2 or 5.5 to 6.2.

According to one embodiment, the liquid pharmaceutical formulation comprises a) 150 mg/ml of the antibody;

b) 185 mM trehalose;

c) 0.2 mg/ml polysorbate 20; and d) 10 mM acetate buffer;

wherein the pH is 5.7.

This liquid formulation may be an aqueous formulation and in one embodiment, does not comprise any further additives.

Specific Embodiments for Buffer-Free Formulations Comprising 150 mg/Ml Antibody

As disclosed herein, also buffer-free liquid pharmaceutical formulations, in particular aqueous formulations, are provided. According to one embodiment, the liquid pharmaceutical formulation comprises a) 150 mg/ml of the antibody;

b) a polyol, optionally wherein the polyol is a sugar or sugar alcohol; and c) a non-ionic surfactant, optionally a polysorbate;

d) no buffer.

As noted above, the present disclosure also provides buffer-free formulations and no buffer is added as excipient. At 150 mg/ml, the antibody having the light and heavy chain sequences as shown in SEQ ID NO: 1 and 2 has a high buffering capacity. Storage-stable buffer-free formulations can be provided based on the disclosure provided herein as is also shown in the examples.

In embodiments, the pH of the buffer-free formulation is in a range of pH 5.2 to pH 6.5. The pH may be in the range of 5.2 to 6.2 or 5.5 to 6.2. In one embodiment, the pH is 5.7. In a further embodiment, the pH is 6.2.

In embodiments, the buffer-free formulation comprises 80 mM to 250 mM polyol. Suitable polyols such as sugars and sugar alcohols were disclosed in detail above and it is referred to this disclosure. In one embodiment, the sugar is trehalose.

According to one embodiment, the concentration of the non-ionic surfactant in the buffer-free formulation is in the range of 0.05 mg/ml to 0.5 mg/ml, 0.075 mg/ml to 0.4 mg/ml or 0.1 mg/ml to 0.3 mg/ml. According to one embodiment, the non-ionic surfactant is a polysorbate. It may be selected from polysorbate 20 and polysorbate 80 and is one embodiment polysorbate 20.

Further Optional Components

In one embodiment, the liquid pharmaceutical formulation according to the present disclosure comprises an amino acid as further additive. Suitable embodiments for amino acids that can be added as excipient to a pharmaceutical formulation are known in the art and are also disclosed in the examples.

In one embodiment, the formulation comprises an amino acid which has a charged side chain, optionally a positive-charged side chain. An example of such amino acid is L-arginine.

According to one embodiment, the formulation comprises an amino acid, wherein the amino acid is present in the formulation as a salt, optionally a hydrochloride (HCl) salt.

According to one embodiment, the formulation comprises methionine. According to one embodiment, the formulation comprises amino acid L-proline.

According to one embodiment, the 150 mg/ml formulation according to the present disclosure does not comprise arginine. It was found that arginine containing formulations showed slightly elevated particle count during freeze/thaw stress studies as well as higher turbidity vales, even though there was no increase in turbidity over time. The viscosity was found to be higher. The amount of aggregates was slightly lower compared to other formulations comprising 150 mg/ml antibody but no arginine.

According to one embodiment, the formulation according to the present disclosure does not comprise an amino acid with a positive-charged side chain as excipient. According to one embodiment, the formulation according to the present disclosure does not comprise an amino acid with a charged side chain as excipient. According to one embodiment, the formulation according to the present disclosure does not comprise methionine as excipient. According to one embodiment, the formulation according to the present disclosure does not comprise an amino acid as additive.

Other excipients known in the art can be used in the formulation, as long as they do not negatively affect the stability.

However, in certain embodiments, no additional excipients are comprised in the formulation of the present disclosure. It is a particular advantage that a storage stable formulation of the antibody risankizumab can be provided with a formulation that consists essentially of or consists of a) the antibody (150 mg/ml); component b); c) a surfactant and optionally d) a buffer. As disclosed herein, it is advantageous that the formulation may comprise only a single polyol, a single surfactant and if present, a single buffer. Thereby a non-complex but nevertheless storage stable formulation is provided for the 150 mg/ml formulation of the antibody risankizumab.

Stability Characteristics

As disclosed herein, advantageously, liquid pharmaceutical formulations comprising 150 mg/ml of the antibody are provided that are stable. Providing such stable, high-concentration formulation of the antibody risankizumab is particularly advantageous for therapeutic uses.

In the embodiments, a stable antibody formulation is a formulation wherein the antibody essentially retains its physical stability and/or biological activity upon storage. Various analytical techniques for measuring protein stability are available in the art and are disclosed herein. Stability can be measured at a selected temperature for a selected time period.

The stability characteristics of different liquid pharmaceutical formulations comprising 150 mg/ml of the antibody according to the present disclosure were tested in the examples and showed advantageous stability characteristics.

In embodiments, the stable liquid pharmaceutical formulation of the present disclosure shows no significant changes at a refrigerated temperature (2-8° C.) for at least 3 months, such as 6 months, or 1 year, or even up to 2 years or longer. A stable liquid formulation includes one that exhibits desired features at temperatures including 25° C. and 40° C. for periods including 1 month, 3 months, 6 months, 12 months, and/or 24 months.

The antibody in particular retains its physical stability in the pharmaceutical formulation, if it shows no significant increase of aggregation, precipitation and/or denaturation upon visual examination of color and/or clarity, or as measured by UV light scattering, size exclusion chromatography (SEC) and/or dynamic light scattering. The changes of protein conformation can be evaluated by fluorescence spectroscopy, which determines the protein tertiary structure, and by FTIR spectroscopy, which determines the protein secondary structure.

The antibody in particular retains its biological activity in the pharmaceutical formulation, if the biological activity of the antibody at a given time is within a predetermined range of the biological activity exhibited at the time the pharmaceutical formulation was prepared. The biological activity of the antibody can be determined, for example, by an antigen binding assay.

Aggregates can differ in origin, size, and type. Aggregates that can affect a biologic product's efficacy or safety are of particular concern, e.g. aggregates that can enhance immune responses and cause adverse clinical effects. High molecular weight aggregates, also called High Molecular Weight Species (HMWS) can be of particular concern. Aggregation can also potentially affect the subcutaneous bioavailability and pharmacokinetics of a therapeutic protein. It is advantageous that the present disclosure provides formulations, wherein the amount of high molecular weight species is low, also over extended storage times. The present disclosure in particular provides stabilized (or stable) aqueous pharmaceutical formulations as demonstrated by the reduced amounts of aggregates and/or reduced aggregate formation rates following storage. As described herein, the stability of such formulations is shown by the reduced amounts of HMWS and/or reduced HMWS formation rates following storage for varied time periods and at varied temperatures. In general, higher stability formulations are associated with lower amounts of HMWS, lower HMWS formation rates, and/or higher antibody main peaks at higher storage temperatures, relative to lower temperatures. As used herein, the term "high molecular weight species" or "HMWS" refers to higher order aggregates of the antibody of the formulations, as well as lower order aggregates of the antibody of the formulations. Lower order aggregates, include, for example, dimer species. The aggregate amounts and rates of formation may be measured or monitored by various techniques, including those disclosed in the examples.

As used herein, the term "low molecular weight species" or "LMWS" in particular refers to fragments of the antibody that are smaller than the monomer, including but not limited to free light chains, free heavy chains, molecules comprising one light chain and one heavy chain, antibody molecules missing one or both light chains, and antibody fragments obtained by cleavage of polypeptide chain(s) such as proteolytic fragments or other enzymatically or chemically degraded antibody molecules.

In certain embodiments, the antibody in the formulation disclosed herein is essentially maintained in monomeric form during storage. In particular embodiments, the formulation may fulfill one or more of the following stability characteristics:

In certain embodiments, following storage at 5° C. for 36 months, at least 94% of the antibody is present as a monomer as measured by UP-SEC, and/or the relative monomer content of the antibody does not decrease by more than 3% or more than 2.5%. In certain embodiments, following storage at 5° C. for 36 months, at least 95% or at least 96% of the antibody is present as a monomer as measured by UP-SEC, and/or the relative monomer content of the antibody does not decrease by more than 2% or more than 1.5%. In certain embodiments, following storage at 5° C. for 24 months, at least 94% of the antibody is present as a monomer as measured by UP-SEC, and/or the relative monomer content of the antibody does not decrease by more than 3% or more than 2.5%. In certain embodiments, following storage at 5° C. for 24 months, at least 95% or at least 96% of the antibody is present as a monomer as measured by UP-SEC, and/or the relative monomer content of the antibody does not decrease by more than 2% or more than 1.5% or more than 1%. In certain embodiments, following storage at 5° C. for 9 months, at least 96% or at least 96.5% of the antibody is present as a monomer as measured by UP-SEC, and/or the relative monomer content of the antibody does not decrease by more than 1.5% or more than 1%. In certain embodiments, following storage at 5° C. for 3 months, at least 96% or at least 97% of the antibody is present as a monomer as measured by UP-SEC, and/or the relative monomer content of the antibody does not decrease by more than 1% or more than 0.7% or more than 0.5%. In certain embodiments, following storage at 25° C. for 12 months, at least 90% or at least 92% of the antibody is present as a monomer as measured by UP-SEC, and/or the relative monomer content of the antibody does not decrease by more than 7% or more than 6% or more than 5%. In certain embodiments, following storage at 25° C. for 3 months, at least 95% of the antibody is present as a monomer as measured by UP-SEC, and/or the relative monomer content of the antibody does not decrease by more than 3% or more than 2%. In certain embodiments, following storage at 25° C. for 1 month, at least 96% of the antibody is present as a monomer as measured by UP-SEC, and/or the relative monomer content of the antibody does not decrease by more than 2% or more than 1%. In certain embodiments, following storage at 40° C. for 3 months, at least 87% or at least 88% of the antibody is present as a monomer as measured by UP-SEC, and/or the relative monomer content of the antibody does not decrease by more than 10% or more than 9% or more than 8%. In certain embodiments, following storage at 40° C. for 1 month, at least 93% or at least 94% of the antibody is present as a monomer as measured by UP-SEC, and/or the relative monomer content of the antibody does not decrease by more than 5% or more than 4%. In certain embodiments, following shaking at 25° C. for 21 days, at least 95% or at least 96% of the antibody is present as a monomer as measured by UP-SEC, and/or the relative monomer content of the antibody does not decrease by more than 2% or more than 1%. The decrease of the relative monomer content is calculated for the indicated storage time and temperature and in particular determined by comparing the relative monomer content at the beginning and at the end of the indicated storage. In particular embodiments, the measurements are performed as is described in the examples.

In certain embodiments, the antibody in the formulation disclosed herein does not form significant amounts of HMWS during storage. In particular, the formulation fulfills one or more of the following stability characteristics:

In certain embodiments, following storage at 5° C. for 36 months, less than 4% or less than 3% of the antibody is present as HMWS as measured by UP-SEC, and/or the relative HMWS content of the antibody does not increase by more than 2% or more than 1.5%. In certain embodiments, following storage at 5° C. for 24 months, less than 4% or less than 3% of the antibody is present as HMWS as measured by UP-SEC, and/or the relative HMWS content of the antibody does not increase by more than 2% or more than 1.5% or more than 1%. In certain embodiments, following storage at 5° C. for 9 months, less than 4% or less than 3% or less than 2.5% of the antibody is present as HMWS as measured by UP-SEC, and/or the relative HMWS content of the antibody does not increase by more than 1% or more than 0.8% or more than 0.6%. In certain embodiments, following storage at 5° C. for 3 months, less than 4% or less than 3% or less than 2.5% of the antibody is present as HMWS as measured by UP-SEC, and/or the relative HMWS content of the antibody does not increase by more than 1% or more than 0.8% or more than 0.6%. In certain embodiments, following storage at 25° C. for 12 months, less than 5% or less than 4% of the antibody is present as HMWS as measured by UP-SEC, and/or the relative HMWS content of the antibody does not increase by more than 3% or more than 2.5% or more than 2%. In certain embodiments, following storage at 25° C. for 3 months, less than 4% or less than 3.5% or less than 3.2% of the antibody is present as HMWS as measured by UP-SEC, and/or the relative HMWS content of the antibody does not increase by more than 2% or more than 1.5%. In certain embodiments, following storage at 25° C. for 1 month, less than 4% or less than 3.5% or less than 3% of the antibody is present as HMWS as measured by UP-SEC, and/or the relative HMWS content of the antibody does not increase by more than 1.5% or more than 1%. In certain embodiments, following storage at 40° C. for 3 months, less than 6.5% or less than 6% or less than 5.5% of the antibody is present as HMWS as measured by UP-SEC, and/or the relative HMWS content of the antibody does not increase by more than 5% or more than 4%. In certain embodiments, following storage at 40° C. for 1 month, less than 5% or less than 4.5% or less than 4% of the antibody is present as HMWS as measured by UP-SEC, and/or the relative HMWS content of the antibody does not increase by more than 2.5% or more than 2%. In certain embodiments, following shaking at 25° C. for 21 days, less than 3% or less than 2% of the antibody is present as HMWS as measured by UP-SEC, and/or the relative HMWS content of the antibody does not increase by more than 2% or more than 1.5% or more than 1%. The increase of the relative HMWS content is calculated for the indicated storage time and temperature and in particular determined by comparing the relative HMWS content at the beginning and at the end of the indicated storage. In particular embodiments, the measurements are performed as is described in the examples.

In further embodiments, the antibody in the formulation disclosed herein does not form significant amounts of LMWS during storage. In particular embodiments, the formulation may fulfill one or more of the following stability characteristics:

In certain embodiments, following storage at 5° C. for 36 months, less than 2% or less than 1.5% of the antibody is present as LMWS as measured by UP-SEC, and/or the relative LMWS content of the antibody does not increase by more than 1.5% or more than 1.5% or more than 0.5%. In certain embodiments, following storage at 5° C. for 24 months, less than 2% or less than 1.5% of the antibody is present as LMWS as measured by UP-SEC, and/or the relative LMWS content of the antibody does not increase by more than 1.5% or more than 1.5% or more than 0.5%. In certain embodiments, following storage at 5° C. for 9 months, less than 2% or less than 1.5% of the antibody is present as LMWS as measured by UP-SEC, and/or the relative LMWS content of the antibody does not increase by more than 1.5% or more than 1.5% or more than 0.5%. In certain embodiments, following storage at 5° C. for 3 months, less than 2% or less than 1.5% or less than 1% of the antibody is present as LMWS as measured by UP-SEC, and/or the relative LMWS content of the antibody does not increase by more than 1% or more than 0.5% or more than 0.25%. In certain embodiments, following storage at 25° C. for 12 months, less than 6% or less than 5% or less than 4.5% of the antibody is present as LMWS as measured by UP-SEC, and/or the relative LMWS content of the antibody does not increase by more than 5% or more than 4% or more than 3%. In certain embodiments, following storage at 25° C. for 3 months, less than 3% or less than 2% or less than 1.8% of the antibody is present as LMWS as measured by UP-SEC, and/or the relative LMWS content of the antibody does not increase by more than 2% or more than 1.5% or more than 1%. In certain embodiments, following storage at 25° C. for 1 month, less than 2% or less than 1.5% or less than 1.2% of the antibody is present as LMWS as measured by UP-SEC, and/or the relative LMWS content of the antibody does not increase by more than 1% or more than 0.6% or more than 0.4%. In certain embodiments, following storage at 40° C. for 3 months, less than 8% or less than 7% or less than 6% of the antibody is present as LMWS as measured by UP-SEC, and/or the relative LMWS content of the antibody does not increase by more than 8% or more than 7% or more than 6%. In certain embodiments, following storage at 40° C. for 1 month, less than 4% or less than 3.5% or less than 3% of the antibody is present as LMWS as measured by UP-SEC, and/or the relative LMWS content of the antibody does not increase by more than 3% or more than 2.5% or more than 2.2%. The increase of the relative LMWS content is calculated for the indicated storage time and temperature and in particular determined by comparing the relative LMWS content at the beginning and at the end of the indicated storage. In particular embodiments, the measurements are performed as is described in the examples.

In certain embodiments, the relative amount of the antibody being in monomeric form, HMWS and/or LMWS is determined using UP-SEC, in particular as described in the examples. For example, an ultra-performance liquid chromatography (UPLC) system such as an Acquity UPLC system of Waters (Milford, MA, USA) comprising a size exclusion chromatography (SEC) column is used. Proteins eluting from the SEC column may be detected by UV absorption at 280 nm and determining of the relative amounts may be done by calculating the area under the curve (AUC) for each elution peak. Peaks may be assigned to the different species by their elution time corresponding to the molecular size of the species. For measuring the relative monomer content, relative HMWS content and/or relative LMWS content of the antibody in the formulation, in particular the monomeric antibody, HMWS and LMWS are separated from each other, if present in the formulation. In particular, the relative content or amount is indicated as a percentage value and the sum of monomeric antibody, HMWS and LMWS is 100%.

In certain embodiments, the turbidity or opalescence of the formulation disclosed herein does not significantly increase during storage. In particular embodiments, the formulation may fulfill one or more of the following stability characteristics:

In certain embodiments, following storage at 5° C. for at least 36 months, the formulation has an opalescence of 12 FNU (Formazin Nephelometry Units) or less or 10 FNU or less, and/or the opalescence does not increase by more than 5 FNU or more than 3 FNU. In certain embodiments, following storage at 5° C. for at least 3, 6, 9, 12, 18 or 24 months, the formulation has an opalescence of 12 FNU (Formazin Nephelometry Units) or less or 10 FNU or less, and/or the opalescence does not increase by more than 5 FNU or more than 3 FNU. In certain embodiments, following storage at 25° C. for at least 1, 3, 6, 9 or 12 months, the formulation has an opalescence of 12 FNU or less or 10 FNU or less, and/or the opalescence does not increase by more than 7 FNU or more than 5 FNU. In certain embodiments, following storage at 40° C. for at least 1 or 3 months, the formulation has an opalescence of 12 FNU or less or 10 FNU or less, and/or the opalescence does not increase by more than 5 FNU or more than 3 FNU. In certain embodiments, following shaking at 25° C. for 21 days, the formulation has an opalescence of 12 FNU or less or 10 FNU or less, and/or the opalescence of the formulation does not increase by more than 3 FNU or more than 2 FNU. The increase of the opalescence is calculated for the indicated storage time and temperature and in particular determined by comparing the opalescence at the beginning and at the end of the indicated storage. In particular embodiments, the measurements are performed as is described in the examples.

In certain embodiments, the opalescence or turbidity is measured according to pharmacopeia or according to industrial standard ISO 7027. In certain embodiments, the opalescence or turbidity of the formulation is determined using a nephelometer such as a HACH Lange opalescence meter of Hach-Lange GmbH (Germany), in particular as described in the examples. Opalescence may be measured at different wavelengths, including at 400-600 nm. In embodiments, the FNA values indicated above are measured at 400-600 nm. Higher FNU values indicate a higher opalescence and turbidity.

In certain embodiments, the antibody in the formulation disclosed herein does not form significant additional amounts of acidic or basic variants during storage. In particular embodiments, the formulation may fulfill one or more of the following stability characteristics:

In certain embodiments, following storage at 5° C. for 36 months, at least 55%, at least 60% or at least 65% of the antibody is present as main peak variants, and/or the relative content of main peak variants of the antibody does not decrease by more than 8% or more than 7% or more than 5%, as determined by ion exchange chromatography (IEC). In certain embodiments, following storage at 5° C. for 24 months, at least 55%, at least 60% or at least 65% of the antibody is present as main peak variants, and/or the relative content of main peak variants of the antibody does not decrease by more than 8% or more than 7% or more than 5%, as determined by ion exchange chromatography (IEC). In certain embodiments, following storage at 5° C. for 6 months, at least 60% or at least 65% of the antibody is present as main peak variants, and/or the relative content of main peak variants of the antibody does not decrease by more than 5% or more than 4%, as determined by ion exchange chromatography (IEC). In certain embodiments, following storage at 5° C. for 3 months, at least 60% or at least 65% of the antibody is present as main peak variants, and/or the relative content of main peak variants of the antibody does not decrease by more than 4% or more than 3% or more than 2%, as determined by ion exchange chromatography (IEC). In certain embodiments, following storage at 25° C. for 12 months, at least 35% or at least 40% or at least 45% of the antibody is present as main peak variants, and/or the relative content of main peak variants of the antibody does not decrease by more than 35% or more than 30% or more than 25%, as determined by ion exchange chromatography (IEC). In certain embodiments, following storage at 25° C. for 3 months, at least 55% or at least 60% of the antibody is present as main peak variants, and/or the relative content of main peak variants of the antibody does not decrease by more than 15% or more than 10%, as determined by ion exchange chromatography (IEC). In certain embodiments, following storage at 25° C. for 1 month, at least 60% or at least 65% of the is present as main peak variants, and/or the relative content of main peak variants of the antibody does not decrease by more than 10% or more than 5%, as storage at 5° C. for 36 months, less than 30% or less than 28% of the antibody is present as acidic peak group variants, and/or the relative content of acidic peak group variants of the antibody does not increase by more than 4% or more than 3% or more than 2%, as determined by ion exchange chromatography (IEC). In certain embodiments, following storage at 5° C. for 24 months, less than 30% or less than 28% of the antibody is present as acidic peak group variants, and/or the relative content of acidic peak group variants of the antibody does not increase by more than 4% or more than 3% or more than 2%, as determined by ion exchange chromatography (IEC). In certain embodiments, following storage at 5° C. for 6 months, less than 30% or less than 28% of the antibody is present as acidic peak group variants, and/or the relative content of acidic peak group variants of the antibody does not increase by more than 4% or more than 3% or more than 2%, as determined by ion exchange chromatography (IEC). In certain embodiments, following storage at 5° C. for 3 months, less than 30% or less than 28% of the antibody is present as acidic peak group variants, and/or the relative content of acidic peak group variants of the antibody does not increase by more than 3% or more than 2% or more than 1%, as determined by ion exchange chromatography (IEC). In certain embodiments, following storage at 25° C. for 12 months, less than 50%, less than 45% or less than 40% of the antibody is present as acidic peak group variants, and/or the relative content of acidic peak group variants of the antibody does not increase by more than 30% or more than 25% or more than 20%, as determined by ion exchange chromatography (IEC). In certain embodiments, following storage at 25° C. for 3 months, less than 40% or less than 35% or less than 30% of the antibody is present as acidic peak group variants, and/or the relative content of acidic peak group variants of the antibody does not increase by more than 10% or more than 8% or more than 6%, as determined by ion exchange chromatography (IEC). In certain embodiments, following storage at 25° C. for 1 month, less than 35% or less than 30% or less than 28% of the antibody is present as acidic peak group variants, and/or the relative content of acidic peak group variants of the antibody does not increase by more than 4% or more than 3%, as determined by ion exchange chromatography (IEC). In certain embodiments, following storage at 5° C. for 36 months, less than 20%, less than 17%, less than 15% or less than 13% of the antibody is present as basic peak group variants, and/or the relative content of basic peak group variants of the antibody does not increase by more than 10% or more than 8% or more than 6%, as determined by ion exchange chromatography (IEC). In certain embodiments, following storage at 5° C. for 24 months, less than 20%, less than 17%, less than 15% or less than 13% of the antibody is present as basic peak group variants, and/or the relative content of basic peak group variants of the antibody does not increase by more than 10% or more than 8% or more than 6%, as determined by ion exchange chromatography (IEC). In certain embodiments, following storage at 5° C. for 6 months, less than 15% or less than 10% of the antibody is present as basic peak group variants, and/or the relative content of basic peak group variants of the antibody does not increase by more than 4% or more than 3% or more than 2%, as determined by ion exchange chromatography (IEC). In certain embodiments, following storage at 5° C. for 3 months, less than 15% or less than 10% of the antibody is present as basic peak group variants, and/or the relative content of basic peak group variants of the antibody does not increase by more than 3% or more than 2%, as storage at 25° C. for 12 months, less than 30% or less than 25% or less than 22% of the antibody is present as basic peak group variants, and/or the relative content of basic peak group variants of the antibody does not increase by more than 25% or more than 20% or more than 15%, as determined by ion exchange chromatography (IEC). In certain embodiments, following storage at 25° C. for 3 months, less than 20% or less than 15% or less than 12% of the antibody is present as basic peak group variants, and/or the relative content of basic peak group variants of the antibody does not increase by more than 9% or more than 7% or more than 5%, as determined by ion exchange chromatography (IEC). In certain embodiments, following storage at 25° C. for 1 month, less than 15% or less than 10% or less than 9% of the antibody is present as basic peak group variants, and/or the relative content of basic peak group variants of the antibody does not increase by more than 3% or more than 2%, as determined by ion exchange chromatography (IEC). The decrease of the relative content of the main peak variants and the increase of the relative content of the acidic and basic peak group variants are calculated for the indicated storage time and temperature and in particular determined by comparing the relative content of the respective peak variants at the beginning and at the end of the indicated storage. In particular embodiments, the measurements are performed as is described in the examples.

In certain embodiments, the relative amount of the antibody being main peak variants, acidic peak variants and/or basic peak variants is determined using ion exchange chromatography (IEC), in particular as described in the examples. In particular, weak cation exchange chromatography (WCX) is used. For example, a high-performance liquid chromatography (HPLC) system such as an Alliance HPLC system of Waters (Milford, MA, USA) comprising a WCX column is used. Proteins eluting from the WCX column may be detected by UV absorption at 280 nm and determining of the relative amounts may be done by calculating the area under the curve (AUC) for each elution peak or each group of elution peaks. Peaks may be assigned to the different species by their elution conditions corresponding to the surface charge of the antibody species. The main peak is the largest peak in an IEC chromatogram of the non-degraded antibody. For the stability analysis, the measurement can be performed after preparation of the formulation (T0) and then after the indicated storage time under the indicated storage condition. The acidic peak group (ΔPG) includes all peaks prior to the main peak. These peaks include antibody variants which are more acidic than the native antibody variants of the main peak, and/or which have more negative charges on their surface under the chromatography conditions. The basic peak group includes all peaks after the main peak. These peaks include antibody variants which are more acidic than the native antibody variants of the main peak, and/or which have more positive charges on their surface under the chromatography conditions. For measuring the relative amount of main peak variants, acidic peak group variants and/or basic peak group variants of the antibody in the formulation, in particular the main peak is separated from the acidic peak group and the basic peak group, if present in the formulation. In particular, the relative content or amount is indicated as a percentage value and the sum of main peak variants, acidic peak group variants and basic peak group variants is 100%.

In certain embodiments, the antibody in the formulation disclosed herein essentially maintains its specific binding activity to human IL-23 during storage. In particular embodiments, the formulation fulfills one or more of the following stability characteristics:

In certain embodiments, following storage at 5° C. for 36 months, at least 95% or at least 97% of the specific binding activity to IL-23 is measured compared to a reference antibody, wherein the reference antibody has not been stored. In certain embodiments, following storage at 5° C. for 4, 6, 9, 12, 18 or 24 months, at least 95% or at least 97% of the specific binding activity to IL-23 is measured compared to a reference antibody, wherein the reference antibody has not been stored. In certain embodiments, following storage at 25° C. for 2, 3, 4, 6, 9, 12, or 18 months, at least 93% or at least 96% of the specific binding activity to IL-23 is measured compared to a reference antibody, wherein the reference antibody has not been stored. In certain embodiments, following storage at 40° C. for 3, 4 or 6 months, at least 90% or at least 95% of the specific binding activity to IL-23 is measured compared to a reference antibody, wherein the reference antibody has not been stored. In particular embodiments, the measurements are performed as is described in the examples.

In certain embodiments, the specific binding activity to human IL-23 of the antibody in the formulation is determined using surface plasmon resonance measurements, for example using a Biacore instrument such as Biacore T200 of GE Healthcare Life Science (United Kingdom), in particular as described in the examples.

Further Characteristics of the Liquid Pharmaceutical Formulation According to the First Aspect In advantageous embodiments, the liquid pharmaceutical formulation of the present disclosure is an aqueous formulation. All liquid formulations disclosed herein are in one embodiment an aqueous formulation. The following description applies to the 150 mg/ml formulation according to the first aspect and therefore, also applies to the formulations according to the first and second sub-aspect as disclosed herein, unless the specific context indicates otherwise.

According to one embodiment the dynamic viscosity of the liquid pharmaceutical formulation according to the first aspect measured at 20° C. is ≤30 mPas (mPa·s), such as ≤25 mPas or ≤20 mPas. In embodiments, the dynamic viscosity of the formulation measured at 20° C. is ≤18 mPas, such as ≤16 mPas, ≤15 mPas, ≤14 mPas, ≤13 mPas or ≤12 mPas. In specific embodiments, the dynamic viscosity is such that the formulation is suitable for subcutaneous administration, as is also shown in the examples. The dynamic viscosity may be determined as described in the examples.

According to one embodiment, the formulation of the present disclosure has a conductivity in a range of 0.8 to 5 mS/cm. In embodiments, the conductivity range is 1 to 2 mS/cm or 1.2 to 1.8 mS/cm. In embodiments, the formulation is characterized in that the change of conductivity over a storage time of at least 12 months at 25° C. is ≤1 mS/cm, such as ≤0.75 mS/cm, ≤0.5 mS/cm or ≤0.3 mS/cm.

The liquid formulation according to the present disclosure is a pharmaceutical formulation. A pharmaceutical formulation in particular refers to compositions which are in such form as to permit the active ingredient (here the antibody comprising a light chain as shown in SEQ ID NO: 1 and a heavy chain as shown in SEQ ID NO: 2) to be effective, and which contains no additional components which are toxic to the subjects to which the formulation would be administered.

The formulations according to the first aspect disclosed herein are advantageously suitable for parenteral delivery. Parenteral administration includes e.g. subcutaneous, intramuscular, intradermal, intramedullary injections, as well as intrathecal, direct intraventricular, intravenous, intraperitoneal and intravitreal. Drugs can be administered in a variety of conventional ways, such as intraperitoneal, parenteral, intraarterial or intravenous injection. In one embodiment, the disclosed formulation is an injectable formulation. The formulation disclosed herein is in embodiments suitable for subcutaneous, intravenous, or intramuscular administration. Advantageously, the disclosed formulation is suitable for subcutaneous injection. The 150 mg/ml formulation disclosed herein is particularly advantageous, because overall characteristics are achieved which makes the formulation particularly suitable for subcutaneous administration. The high concentration allows to administer a small volume of the formulation while still achieving a high antibody dose (here e.g. 1 ml for 150 mg dose). Furthermore, the formulations according to the present disclosure show a good syringeability. They moreover have advantageous viscosity and osmolality characteristics and achieve good glide forces (max and average), also upon storage as is disclosed in the examples. In embodiments, the liquid pharmaceutical formulation according to the present disclosure is isotonic with the intended site of administration. For example, if the formulation is intended for administration parenterally, it can be isotonic with blood (which is about 300 mOsm/kg osmolality). Suitable osmolality ranges are described elsewhere.

The liquid antibody formulation can be made by taking the drug substance which is in liquid form (e.g., in an aqueous pharmaceutical formulation) and buffer exchanging and preparing it into the desired buffer as the last step of the purification process. The drug substance in the final buffer may be concentrated to a desired concentration or a more concentrated form of the antibody is diluted to achieve the 150 mg/ml concentration. Concentration of the formulation can be carried out by any suitable method. In one aspect, the concentration process can include ultrafiltration.

The liquid pharmaceutical formulation according to the first aspect is in one core embodiment not a formulation that has been prepared by reconstituting a lyophilized formulation. In this core embodiment, there is no lyophilization step during the preparation of the liquid pharmaceutical formulation. Excipients such as component b) and surfactant c) may be added to the drug substance which may be diluted using the appropriate buffer to final protein concentration of 150 mg/ml. A pharmaceutical formulation to be used for in vivo administration typically is sterile. In certain embodiments, this may be accomplished by filtration through sterile filtration membranes. The final formulated drug substance may thus be filtered (e.g. using 0.22 µm filters) and may be filled into a final container (e.g. glass vials or syringe). The prepared liquid formulation is in this embodiment for direct administration to the patient so that there is no lyophilization or reconstitution step. Such liquid pharmaceutical formulations are disclosed herein and were also made and analysed in the examples.

Lyophilized and Reconstituted Pharmaceutical Formulations

According to one embodiment, the liquid pharmaceutical formulation according to the first aspect is prepared from a lyophilized pharmaceutical formulation by reconstitution. In embodiments, the liquid pharmaceutical composition described herein is thus a reconstituted formulation. This applies to the liquid formulations according to the first and second sub-aspect of the 150 mg/ml antibody formulation according to the first aspect.

The terms "lyophilization," or "lyophilized" in particular refer to a process by which the material to be dried is first frozen and then the ice or frozen solvent is removed by sublimation in a vacuum environment. Such technologies are well-known in the art and therefore, are not described in detail herein. An excipient may be included in pre-lyophilized formulations to enhance stability of the lyophilized product upon storage. The lyophilized formulation may comprise a cryoprotectant, which generally includes agents which provide stability to the protein against freezing-induced stresses. They may also offer protection during primary and secondary drying, and long-term product storage. Examples include sugars such as sucrose and trehalose and surfactants such as polysorbates. The lyophilized formulation may also include a lyoprotectant, which includes agents that provide stability to the protein during the drying or dehydration process (primary and secondary drying cycles). This helps to maintain the protein conformation, minimize protein degradation during the lyophilization cycle and improve the long-term product stability. Examples include polyols, such as sugars, e.g. sucrose and trehalose. The liquid pharmaceutical formulations disclosed according to the first aspect comprise excipients that qualify as cryo-and/or lyoprotectant. accordingly, lyophilized formulations may be prepared from such formulations. In an embodiment, the antibody risankizumab is formulated as a lyophilized powder for reconstituting and utilizing for intravenous administration.

A "reconstituted" formulation is one that has been prepared by dissolving a lyophilized pharmaceutical antibody formulation in a diluent such that the antibody is dispersed in the reconstituted formulation. The reconstituted formulation is suitable for administration, and may optionally be suitable for subcutaneous administration.

The lyophilized pharmaceutical formulation is prepared in anticipation of reconstitution at the desired concentration, here 150 mg/ml of the antibody.

According to one embodiment, a lyophilized formulation of an anti-IL-23p19 antibody is provided, wherein the antibody comprises a light chain amino acid sequence according to SEQ ID NO: 1 and a heavy chain amino acid sequence according to SEQ ID NO: 2. According to one embodiment, the lyophilized formulation of the antibody risankizumab is defined in terms of the solution used to make the lyophilized formulation, e.g. the pre-lyophilization solution. This lyophilized formulation is made by lyophilizing the liquid 150 mg/ml antibody formulation according to the first aspect, such as the liquid pharmaceutical formulation according to the first aspect as defined in any one of the below embodiments 1 to 86. As disclosed herein, the liquid formulation is in one embodiment an aqueous formulation. Such aqueous formulation may be used to prepare the lyophilized pharmaceutical formulation.

In yet other embodiments, the lyophilized formulation of the antibody risankizumab is defined in terms of the reconstituted solution generated from the lyophilized formulation. According to one embodiment, a lyophilized formulation of an anti-IL-23p19 antibody is thus provided, wherein the antibody comprises a light chain amino acid sequence according to SEQ ID NO: 1 and a heavy chain amino acid sequence according to SEQ ID NO: 2, said lyophilized formulation providing upon reconstitution the liquid 150 mg/ml antibody formulation according to the first aspect, in particular the first and second sub-aspect thereof. According to embodiments, the lyophilized formulation provides upon reconstitution the liquid pharmaceutical formulation as defined in any one of the below embodiments 1 to 86 or 104 to 119. This risankizumab formulation may be an aqueous formulation.

Also provided is a lyophilized formulation comprising
a) an anti-IL-23p19 antibody, wherein the antibody comprises a light chain amino acid sequence according to SEQ ID NO: 1 and a heavy chain amino acid sequence according to SEQ ID NO: 2, in an amount that upon reconstitution provides an antibody concentration of 150 mg/ml;

b) a polyol;

c) a surfactant; and d) optionally a buffer.

In one embodiment, the lyophilized pharmaceutical formulation comprises 150 mg of the antibody. The antibody is risankizumab.

Also provided is a lyophilized formulation comprising a) an anti-IL-23p19 antibody, wherein the antibody comprises a light chain amino acid sequence according to SEQ ID NO: 1 and a heavy chain amino acid sequence according to SEQ ID NO: 2, in an amount that upon reconstitution provides an antibody concentration of 150 mg/ml;

b) a tonicity modifier;

c) a surfactant; and d) optionally a buffer.

In one embodiment, the lyophilized pharmaceutical formulation comprises 150 mg of the antibody. The antibody is risankizumab.

The comprised components such as suitable polyols for pharmaceutical formulations were already disclosed above in conjunction with the liquid pharmaceutical formulation and it is referred to the above disclosure which also applies here. Suitable polyols include sugars and sugar alcohols, which may also be used in combination. The polyol may have one or more of the characteristics as defined in any one of the below embodiments 6 to 13 of the liquid pharmaceutical formulation according to the first aspect. In one embodiment, the polyol is a sugar, optionally selected from trehalose and sucrose. In one embodiment, the sugar is trehalose.

Suitable surfactants were already disclosed above in conjunction with the liquid pharmaceutical formulation and it is referred to the above disclosure which also applies here. The surfactant may have one or more of the characteristics as defined in any one of the below embodiments 22 to 25 of the liquid pharmaceutical formulation according to the first aspect. In one embodiment, the surfactant is a polysorbate, optionally selected from polysorbate 20 and 80. In one embodiment, the polysorbate is polysorbate 20.

The lyophilized formulation comprises in one embodiment a buffer. Buffers suitable to prepare lyophilized formulations are known in the art and suitable buffers were also disclosed above in conjunction with the liquid pharmaceutical formulation according to the first aspect and it is referred to the above disclosure.

According to one embodiment, the lyophilized formulation is characterized in that the formulation has upon reconstitution a pH as disclosed herein for the liquid pharmaceutical formulation according to the first aspect. Suitable pH values were disclosed above and it is referred to the respective disclosure which also applies here. Upon reconstitution, the pH may be as defined in any one of the below embodiments 31 to 36 of the liquid 150 mg/ml pharmaceutical formulation. Furthermore, upon reconstitution, the pH may be as defined for the formulation according to second sub-aspect. The pH upon reconstitution may be 5.5 to 5.9, e.g. 5.6 to 5.8.

The lyophilized risankizumab formulations of the present disclosure are reconstituted prior to administration. In some instances, it may be desirable to lyophilize the risankizumab formulation in the container in which reconstitution of the antibody is to be carried out in order to avoid a transfer step.

Containers and Uses

According to a further aspect of the present disclosure, a sealed container is provided which contains the liquid pharmaceutical formulation or the lyophilized pharmaceutical formulation according to the first aspect of the present disclosure. The container may be a vial or pre-filled syringe. In embodiments, the container contains 2 ml or less of the liquid pharmaceutical formulation, optionally 1.5 ml or less or 1 ml or less. Such container may comprise the advantageous stable liquid pharmaceutical formulation according to the first or second sub-aspect of the 150 mg/ml antibody formulation according to the first aspect.

In core embodiments, the container such as the syringe comprises a single dose of 150 mg antibody. As disclosed herein, the antibody is risankizumab.

In one embodiment, the liquid pharmaceutical formulation according to the first aspect of the present disclosure is comprised in a syringe which is equipped with a needle. In particular embodiments, the needle is suitable for subcutaneous administration. The needle may be a 27 Gauge spinal thin-wall needle or other needle suitable for subcutaneous use.

According to one embodiment the pre-filled syringe equipped with a needle has an average gliding force that is 20 N or less. In embodiments, the average gliding force is in the range of 5 to 20 N or 5 to 15 N. In embodiments, the pre-filled syringe has a break loose force of 3 to 12 N, preferably 3 to 9 N.

In certain embodiments, the syringe equipped with a needle and comprising the liquid pharmaceutical formulation according to the first aspect essentially maintains the maximum and/or average gliding force needed to eject it from a syringe during storage. In certain embodiments, following storage at 5° C. for 36 months, the maximum gliding force of the syringe pre-filled with the liquid formulation is 14 N or lower, 12 N or lower or 10 N or lower, and/or the maximum gliding force does not increase by more than 5 N or more than 4 N or more than 3 N. In certain embodiments, following storage at 5° C. for 24 months, the maximum gliding force of the syringe pre-filled with the liquid formulation is 14 N or lower, 12 N or lower, 10 N or lower or 8 N or lower, and/or the maximum gliding force does not increase by more than 3 N or more than 2 N or more than 1.5 N. In certain embodiments, following storage at 5° C. for 9 months, the maximum gliding force is 9 N or lower or 8 N or lower, and/or the maximum gliding force does not increase by more than 2 N or more than 1.5 N or more than 1 N. In certain embodiments, following storage at 5° C. for 3 months, the maximum gliding force is 8 N or lower or 7.5 N or lower, and/or the maximum gliding force does not increase by more than 1.5 N or more than 1 N. In certain embodiments, following storage at 25° C. for 3 months, the maximum gliding force is 10 N or lower or 8 N or lower, and/or the maximum gliding force does not increase by more than 3 N or more than 2 N or more than 1.5 N. In certain embodiments, following storage at 25° C. for 1 month, the maximum gliding force of the pre-filled syringe equipped with a needle is 8 N or lower or 7.5 N or lower, and/or the maximum gliding force does not increase by more than 1.5 N or more than 1 N. In certain embodiments, following storage at 40° C. for 1 month, the maximum gliding force is 16 N or lower or 13 N or lower, and/or the maximum gliding force does not increase by more than 10 N or more than 8 N or more than 6 N.

In certain embodiments, following storage at 5° C. for 36 months, the average gliding force of the syringe prefilled with the liquid formulation according to the first aspect and equipped with a needle is 14 N or lower, 12 N or lower, 10

N or lower or 9 N or lower, and/or the average gliding force does not increase by more than 5 N or more than 4 N or more than 3 N. In certain embodiments, following storage at 5° C. for 24 months, the average gliding force of the syringe prefilled with the liquid formulation according to the first aspect and equipped with a needle is 14 N or lower, 12 N or lower, 10 N or lower or 8 N or lower, and/or the average gliding force does not increase by more than 3 N or more than 2 N or more than 1.5 N. In certain embodiments, following storage at 5° C. for 9 months, the average gliding force of the pre-filled syringe equipped with the needle is 9 N or lower or 7.5 N or lower, and/or the average gliding force does not increase by more than 2 N or more than 1.5 N or more than 1 N. In certain embodiments, following storage at 5° C. for 3 months, the average gliding force is 8 N or lower or 7 N or lower, and/or the average gliding force does not increase by more than 1.5 N or more than 1 N or no more than 0.5 N. In certain embodiments, following storage at 25° C. for 12 months, the average gliding force is 15 N or lower or 13 N or lower, and/or the average gliding force does not increase by more than 9 N or more than 8 N or more than 7 N. In certain embodiments, following storage at 25° C. for 3 months, the average gliding force is 9 N or lower or 8 N or lower, and/or the average gliding force does not increase by more than 3 N or more than 2 N or more than 1.5 N. In certain embodiments, following storage at 25° C. for 1 month, the average gliding force is 8 N or lower or 7 N or lower, and/or the average gliding force does not increase by more than 1.5 N or more than 1 N or no more than 0.5 N. In certain embodiments, following storage at 40° C. for 3 month, the average gliding force is 18 N or lower or 15 N or lower, and/or the average gliding force does not increase by more than 12 N or more than 10 N or more than 9 N. In certain embodiments, following storage at 40° C. for 1 month, the average gliding force is 13 N or lower or 10 N or lower, and/or the average gliding force does not increase by more than 7 N or more than 5 N or more than 3 N.

The increase of the maximum or relative gliding force is calculated for the indicated storage time and temperature and in particular determined by comparing the maximum or relative gliding force at the beginning and at the end of the indicated storage. In particular embodiments, the measurements are performed as is described in the examples.

The maximum gliding force of the formulation refers to the maximum mechanical force needed to eject the formulation from a syringe. The average gliding force of the formulation refers to the average mechanical force needed to eject the formulation from a syringe. In some embodiments, the gliding force is determined according to industrial norms such as ISO 7886, ISO 11040 and ISO 11499. In certain embodiments, the maximum and average gliding force of the formulation is determined using a tensile and compression testing machine such as a Zwick 2.5TS/N of Zwick (Germany), in particular as described in the examples. The measurement may be performed using a 1 ml syringe with a 27 gauge×½ inch needle, such as a Neopak 1 ml syringe of Becton Dickinson (USA), in particular a syringe equipped with a needle as used in the examples. The measurement may be performed using a speed of about 300 to 500 mm/min such as about 380 mm/min, in particular 379.2 mm/min, for example for 5 seconds.

A further aspect according to the present disclosure pertains to the liquid pharmaceutical formulations or the lyophilized pharmaceutical formulations according to the first aspect or the container according to the further aspect disclosed herein for therapeutic treatment of a human subject. The disease to be treated is a disease that can be treated with an anti-IL-23p19 antibody and such diseases are known in the art. The disease may be selected from the group consisting of inflammatory diseases, autoimmune diseases, respiratory diseases, metabolic disorders and cancer. In embodiments, the disease is a chronic disease. The disease to be treated may be selected from psoriasis and inflammatory bowel disease. In further embodiments, the disease to be treated may be selected from psoriatic arthritis and Crohn's disease. Administering the high concentration 150 mg/ml liquid pharmaceutical formulation according to the present disclosure to the patient for therapy is advantageous for the reasons discussed herein.

Further embodiments of the 150 mg/ml formulation

In the following, further specific contemplated embodiments of the 150 mg/ml antibody formulation according to the first aspect are disclosed:

1. A liquid pharmaceutical formulation comprising
   a) 150 mg/ml of an anti-IL-23p19 antibody, wherein the antibody comprises a light chain amino acid sequence according to SEQ ID NO: 1 and a heavy chain amino acid sequence according to SEQ ID NO: 2;
   b) a polyol; and
   c) a surfactant.
2. The formulation according to embodiment 1, comprising
   d) a buffer.
3. The formulation according to embodiment 1 or 2, wherein the antibody is risankizumab.
4. The formulation according to any one of embodiments 1 to 3, wherein the antibody has been recombinantly produced in a mammalian cell.
5. The formulation according to embodiment 4, wherein the antibody has been recombinantly produced in a CHO cell.
6. The formulation according to one or more of embodiments 1 to 5, wherein the polyol is selected from a sugar, a sugar alcohol and combinations thereof.
7. The formulation according to embodiment 6, wherein the polyol is selected from trehalose, sucrose, sorbitol, mannitol and combinations thereof.
8. The formulation according to embodiment 6, wherein the polyol is a sugar, optionally selected from trehalose and sucrose.
9. The formulation according to embodiment 6, comprising trehalose as polyol.
10. The formulation according to embodiment 6, wherein the polyol is selected from sorbitol and mannitol.
11. The formulation according to embodiment 6, comprising mannitol as polyol.
12. The formulation according to any one of embodiments 1 to 11, wherein the liquid pharmaceutical formulation does not comprise sorbitol.
13. The formulation according to one or more of embodiments 1 to 9, wherein the formulation does not comprise a sugar alcohol.
14. The formulation according to one or more of embodiments 1 to 13, having one or more of the following characteristics:
   (i) the concentration of the polyol in the formulation is at least 95 mM;
   (ii) the concentration of the polyol in the formulation is at least 125 mM;
   (iii) the concentration of the polyol in the formulation is at least 150 mM;
   (iv) the concentration of the polyol in the formulation is ≤500 mM, ≤450 mM or ≤400 mM;

(v) the concentration of the polyol in the formulation is ≤350 mM, ≤300 mM or ≤275 mM; and/or (vi) the concentration of the polyol in the formulation lies in the range of 95 mM to 450 mM or 125 mM to 400 mM;

optionally wherein the polyol is a sugar and/or a sugar alcohol.

15. The formulation according to one or more of embodiments 1 to 13, wherein the concentration of the polyol in the formulation is in the range of 95 mM to 250 mM, optionally wherein the polyol is a sugar.

16. The formulation according to one or more of embodiments 1 to 13, wherein the concentration of the polyol in the formulation is in the range of 125 mM to 225 mM, optionally wherein the polyol is a sugar such as trehalose.

17. The formulation according to one or more of embodiments 1 to 13, wherein the concentration of the polyol is in the range of 145 mM to 225 mM, optionally wherein the polyol is a sugar such as trehalose.

18. The formulation according to one or more of embodiments 1 to 13, wherein the polyol is a sugar and wherein the concentration of the sugar is in the range of 150 mM to 200 mM, optionally wherein the sugar is trehalose.

19. The formulation according to one or more of embodiments 1 to 13, wherein the polyol is a sugar and wherein the concentration of the sugar is in the range of 160 mM to 200 mM, optionally wherein the sugar is trehalose.

20. The formulation according to one or more of embodiments 1 to 13, wherein the polyol is a sugar and wherein the concentration of the sugar is in the range of 170 mM to 200 mM, optionally wherein the sugar is trehalose.

21. The formulation according to one or more of embodiments 1 to 13, comprising 185 mM trehalose as polyol.

22. The formulation according to one or more of embodiments 1 to 21, wherein the surfactant is a non-ionic surfactant.

23. The formulation according to embodiment 22, wherein the surfactant is a polysorbate.

24. The formulation according to embodiment 22 or 23, wherein the non-ionic surfactant is selected from polysorbate 20 and/or polysorbate 80.

25. The formulation according to one or more of embodiments 1 to 24, wherein the surfactant is polysorbate 20.

26. The formulation according to one or more of embodiments 1 to 25, in particular any one of embodiments 23 to 25, wherein the concentration of the surfactant in the formulation is at least 0.05 mg/ml, optionally at least 0.075 mg/ml.

27. The formulation according to one or more of embodiments 1 or 26, in particular any one of embodiments 23 to 25, wherein the concentration of the surfactant in the formulation is in a range of 0.05 mg/ml to 0.75 mg/ml.

28. The formulation according to one or more of embodiments 1 or 27, in particular any one of embodiments 23 to 25, wherein the concentration of the surfactant in the formulation is in the range of 0.05 mg/ml to 0.5 mg/ml or 0.075 mg/ml to 0.3 mg/ml.

29. The formulation according to embodiment 25, wherein the formulation comprises 0.2 mg/ml polysorbate 20 as surfactant.

30. The formulation according to embodiment 29, wherein the polyol is a sugar and wherein the concentration of the sugar is in the range of 145 mM to 225 mM, optionally wherein the sugar is trehalose.

31. The formulation according to one or more of embodiments 1 to 30, wherein the pH of the liquid pharmaceutical formulation is in the range of pH 5.0 to 7.5 or pH 5.0 to 7.0.

32. The formulation according to one or more of embodiments 1 to 30, wherein the pH of the liquid pharmaceutical formulation is in a range of 5.2 to 6.5 or 5.2 to 6.2.

33. The formulation according to one or more of embodiments 1 to 30, wherein the pH of the liquid pharmaceutical formulation is in a range of 5.5 to 6.5 or 5.5 to 6.2.

34. The formulation according to one or more of embodiments 1 to 30, wherein the pH of the liquid pharmaceutical formulation is in a range of 5.5 to 5.9.

35. The formulation according to one or more of embodiments 1 to 30, wherein the pH of the liquid pharmaceutical formulation is in a range of 5.6 to 5.8.

36. The formulation according to one or more of embodiments 1 to 30, wherein the pH of the liquid pharmaceutical formulation is 5.7 or 6.2.

37. The formulation according to one or more of embodiments 2 to 36, wherein the buffer has a pKa within 1.5 or one pH unit of the final pH of the liquid pharmaceutical formulation at 25° C., optionally wherein the buffer has a pKa within the range of pH 4.2 to 7.2 or pH 4.5 to 7 at 25° C.

38. The formulation according to one or more of embodiments 2 to 37, wherein the buffer is an organic buffer, which is optionally selected from an acetate buffer and a succinate buffer.

39. The formulation according to embodiment 38, wherein the buffer is an acetate buffer, optionally wherein the acetate buffer comprises sodium acetate and acetic acid.

40. The formulation according to one or more of embodiments 2 to 37, wherein the buffer is a histidine buffer or wherein the formulation fulfills at least one of the following characteristics: (i) it comprises a carboxylic acid buffer; (ii) it does not comprise a succinate buffer.

41. The formulation according to one or more of embodiments 2 to 40, comprising at least 1 mM, at least 2 mM or at least 3 mM buffer, optionally comprising at least 4 mM, at least 4.5 mM or at least 5 mM buffer.

42. The formulation according to one or more of embodiments 2 to 41, wherein the buffer concentration is 100 mM or less, 75 mM or less or 50 mM or less.

43. The formulation according to one or more of embodiments 2 to 41, wherein the buffer concentration is 20 mM or less or 15 mM or less.

44. The formulation according to one or more of embodiments 2 to 41, wherein the buffer concentration is in the range of 4 mM to 50 mM.

45. The formulation according to one or more of embodiments 2 to 41, wherein the buffer concentration is in the range of 5 mM to 25 mM or 5 mM to 20 mM.

46. The formulation according to one or more of embodiments 2 to 41, wherein the buffer concentration is in the range of 5 mM to 15 mM or 7 mM to 12 mM.

47. The formulation according to one or more of embodiments 2 to 41, wherein the buffer concentration is 10 mM.

48. The formulation according to one or more of embodiments 2 to 47, wherein the formulation comprises a single buffer, optionally an acetate buffer.

49. The formulation according to any one of embodiments 1 or 3 to 36, wherein the formulation does not comprise a buffer.

50. The formulation according to one or more of embodiments 1 to 49, wherein the formulation is an aqueous formulation.

51. The formulation according to any one of embodiments 2 to 48 or 50, comprising
   a) 150 mg/ml of the antibody;
   b) a sugar, optionally wherein the concentration of the sugar is in the range of 95 mM to 250 mM or 145 mM to 225 mM;
   c) a non-ionic surfactant, optionally wherein the concentration of the non-ionic surfactant is in the range of 0.05 mg/ml to 0.5 mg/ml or 0.075 mg/ml to 0.3 mg/ml; and
   d) a buffer.

52. The formulation according any one of embodiments 2 to 48 or 50 to 51, comprising
   a) 150 mg/ml of the antibody;
   b) trehalose, optionally wherein the concentration of trehalose is in the range of 95 mM to 250 mM or 145 mM to 225 mM;
   c) a polysorbate, optionally wherein the concentration of the polysorbate is in the range of 0.05 mg/ml to 0.5 mg/ml or 0.075 mg/ml to 0.3 mg/ml; and
   d) a buffer.

53. The formulation according to embodiment 51 or 52, wherein the buffer is an acetate buffer or a succinate buffer, optionally wherein the buffer concentration is in the range of 5 mM to 25 mM.

54. The formulation according to embodiment 52 or 53, wherein the polysorbate is polysorbate 20.

55. The formulation according to any one of embodiments 51 to 54, wherein the pH of the formulation is in a range of pH 5.2 to pH 6.5, optionally wherein the pH is in the range of 5.2 to 6.2 or 5.5 to 6.2 or is 5.7.

56. The formulation according any one of embodiments 2 to 48 or 50 to 55, comprising
   a) 150 mg/ml of the antibody;
   b) 170 mM to about 200 mM trehalose;
   c) 0.1 mg/ml to 0.3 mg/ml polysorbate, optionally polysorbate 20; and
   d) a buffer, optionally wherein the buffer is an acetate buffer.

57. The liquid pharmaceutical formulation according to one or more of embodiments 1, 3 to 36 or 49 to 50, comprising
   a) 150 mg/ml of the antibody;
   b) a polyol, optionally wherein the polyol is a sugar or sugar alcohol; and
   c) a non-ionic surfactant, optionally a polysorbate;
   d) no buffer.

58. The formulation according to embodiment 57, wherein the pH of the formulation is in a range of pH 5.2 to pH 6.5, optionally wherein the pH in the range of 5.2 to 6.2 or 5.5 to 6.2.

59. The formulation according to embodiment 58, wherein the pH is 5.7.

60. The formulation according to any one of embodiments 57 to 59, comprising 80 mM to 250 mM polyol, optionally wherein the polyol is trehalose.

61. The formulation according to any one of embodiments 57 to 60, wherein the concentration of the non-ionic surfactant is in the range of 0.05 mg/ml to 0.5 mg/ml, 0.075 mg/ml to 0.4 mg/ml or 0.1 mg/ml to 0.3 mg/ml.

62. The formulation according to embodiment 61, wherein the non-ionic surfactant is a polysorbate, optionally polysorbate 20.

63. The formulation according to one or more of embodiments 1 to 62, further comprising an amino acid as additive.

64. The formulation according to embodiment 63, wherein the amino acid has a charged side chain, optionally a positive-charged side chain such as L-arginine.

65. The formulation according to embodiment 63 or 64, wherein the amino acid is present in the formulation as a salt, optionally a hydrochloride (HCl) salt.

66. The formulation according to embodiment 63, wherein the amino acid is methionine.

67. The formulation according to embodiment 63, wherein the amino acid is L-proline.

68. The formulation according to one or more of embodiments 1 to 67, wherein the formulation has one or more of the following characteristics
   (i) it does not comprise arginine;
   (ii) it does not comprise an amino acid with a positive-charged side chain;
   (iii) it does not comprise an amino acid with a charged side chain;
   (iv) it does not comprise methionine; and/or
   (v) it does not comprise an amino acid as additive.

69. The liquid pharmaceutical formulation according to any one of embodiments 2 to 68, comprising
   a) 150 mg/ml of the antibody;
   b) 185 mM trehalose;
   c) 0.2 mg/ml polysorbate 20; and
   d) 10 mM acetate buffer;
   wherein the pH is in the range of 5.2 to 6.2 and optionally is 5.7.

70. The formulation according to any one of embodiments 1 to 69, wherein the formulation is stable.

71. The formulation according to embodiment 70, fulfilling one or more of the following stability characteristics:
   (i) following storage at 5° C. for 36 months, at least 94%, at least 95% or at least 96% of the antibody is present as a monomer as measured by UP-SEC, and/or the relative monomer content of the antibody does not decrease by more than 3%, more than 2.5%, more than 2% or more than 1.5%;
   (ii) following storage at 5° C. for 24 months, at least 94%, at least 95% or at least 96% of the antibody is present as a monomer as measured by UP-SEC, and/or the relative monomer content of the antibody does not decrease by more than 3%, more than 2.5%, more than 2%, more than 1.5% or more than 1%;
   (iii) following storage at 5° C. for 9 months, at least 96% or at least 96.5% of the antibody is present as a monomer as measured by UP-SEC, and/or the relative monomer content of the antibody does not decrease by more than 1.5% or more than 1%;
   (iv) following storage at 5° C. for 3 months, at least 96% or at least 97% of the antibody is present as a monomer as measured by UP-SEC, and/or the relative monomer content of the antibody does not decrease by more than 1% or more than 0.7% or more than 0.5%;
   (v) following storage at 25° C. for 12 months, at least 90% or at least 92% of the antibody is present as a monomer as measured by UP-SEC, and/or the relative monomer content of the antibody does not decrease by more than 7% or more than 6% or more than 5%;
   (vi) following storage at 25° C. for 3 months, at least 95% of the antibody is present as a monomer as measured by UP-SEC, and/or the relative monomer content of the antibody does not decrease by more than 3% or more than 2%;
   (vii) following storage at 25° C. for 1 month, at least 96% of the antibody is present as a monomer as measured by UP-SEC, and/or the relative monomer content of the antibody does not decrease by more than 2% or more than 1%;

(viii) following storage at 40° C. for 3 months, at least 87% or at least 88% of the antibody is present as a monomer as measured by UP-SEC, and/or the relative monomer content of the antibody does not decrease by more than 10% or more than 9% or more than 8%; and/or (ix) following storage at 40° C. for 1 month, at least 93% or at least 94% of the antibody is present as a monomer as measured by UP-SEC, and/or the relative monomer content of the antibody does not decrease by more than 5% or more than 4%.

72. The formulation according to embodiment 70 or 71, fulfilling one or more of the following stability characteristics:

(i) following storage at 5° C. for at least 36 months, the formulation has an opalescence of 12 FNU (Formazin Nephelometry Units) or less or 10 FNU or less, and/or the opalescence does not increase by more than 5 FNU or more than 3 FNU;

(ii) following storage at 5° C. for at least 3, 6, 9, 12, 18 or 24 months, the formulation has an opalescence of 12 FNU (Formazin Nephelometry Units) or less or 10 FNU or less, and/or the opalescence does not increase by more than 5 FNU or more than 3 FNU;

(iii) following storage at 25° C. for at least 1, 3, 6, 9 or 12 months, the formulation has an opalescence of 12 FNU or less or 10 FNU or less, and/or the opalescence does not increase by more than 7 FNU or more than 5 FNU;

(iv) following storage at 40° C. for at least 1 or 3 months, the formulation has an opalescence of 12 FNU or less or 10 FNU or less, and/or the opalescence does not increase by more than 5 FNU or more than 3 FNU; and/or (v) following shaking at 25° C. for 21 days, the formulation has an opalescence of 12 FNU or less or 10 FNU or less, and/or the opalescence of the formulation does not increase by more than 3 FNU or more than 2 FNU.

73. The formulation according to any one of embodiments 70 to 72, fulfilling one or both of the following stability characteristics:

(i) following shaking at 25° C. for 21 days, at least 95% or at least 96% of the antibody is present as a monomer as measured by UP-SEC, and/or the relative monomer content of the antibody does not decrease by more than 2% or more than 1%; and/or (ii) following shaking at 25° C. for 21 days, less than 3% or less than 2% of the antibody is present as high molecular weight (HMW) species as measured by UP-SEC, and/or the relative HMW content of the antibody does not increase by more than 2% or more than 1.5% or more than 1%.

74. The formulation according to any one of embodiments 70 to 73, fulfilling one or more of the following stability characteristics:

(i) following storage at 5° C. for 36 months, less than 4% or less than 3% of the antibody is present as high molecular weight (HMW) species as measured by UP-SEC, and/or the relative HMWS content of the antibody does not increase by more than 2% or more than 1.5%;

(ii) following storage at 5° C. for 24 months, less than 4% or less than 3% of the antibody is present as high molecular weight (HMW) species as measured by UP-SEC, and/or the relative HMW content of the antibody does not increase by more than 2% or more than 1.5% or more than 1%;

(iii) following storage at 5° C. for 9 months, less than 4% or less than 3% or less than 2.5% of the antibody is present as high molecular weight (HMW) species as measured by UP-SEC, and/or the relative HMW content of the antibody does not increase by more than 1% or more than 0.8% or more than 0.6%;

(iv) following storage at 5° C. for 3 months, less than 4% or less than 3% or less than 2.5% of the antibody is present as high molecular weight (HMW) species as measured by UP-SEC, and/or the relative HMW content of the antibody does not increase by more than 1% or more than 0.8% or more than 0.6%;

(v) following storage at 40° C. for 3 months, less than 6.5% or less than 6% or less than 5.5% of the antibody is present as a high molecular weight (HMW) species as measured by UP-SEC, and/or the relative HMW content of the antibody does not increase by more than 5% or more than 4%; and/or (vi) following storage at 40° C. for 1 month, less than 5% or less than 4.5% or less than 4% of the antibody is present as high molecular weight (HMW) species as measured by UP-SEC, and/or the relative HMW content of the antibody does not increase by more than 2.5% or more than 2%.

75. The formulation according to any one of embodiments 70 to 74, fulfilling one or more of the following stability characteristics:

(i) following storage at 25° C. for 12 months, less than 5% or less than 4% of the antibody is present as high molecular weight (HMW) species as measured by UP-SEC, and/or the relative HMW content of the antibody does not increase by more than 3% or more than 2.5% or more than 2%;

(ii) following storage at 25° C. for 3 months, less than 4% or less than 3.5% or less than 3.2% of the antibody is present as high molecular weight (HMW) species as measured by UP-SEC, and/or the relative HMW content of the antibody does not increase by more than 2% or more than 1.5%; and/or (iii) following storage at 25° C. for 1 month, less than 4% or less than 3.5% or less than 3% of the antibody is present as high molecular weight (HMW) species as measured by UP-SEC, and/or the relative HMW content of the antibody does not increase by more than 1.5% or more than 1%.

76. The formulation according to any one of embodiments 70 to 75, fulfilling one or more of the following stability characteristics:

(i) following storage at 5° C. for 36 months, less than 2% or less than 1.5% of the antibody is present as low molecular weight (LMW) species as measured by UP-SEC, and/or the relative LMWS content of the antibody does not increase by more than 1.5% or more than 1.5% or more than 0.5%;

(ii) following storage at 5° C. for 24 months, less than 2% or less than 1.5% of the antibody is present as low molecular weight (LMW) species as measured by UP-SEC, and/or the relative LMW content of the antibody does not increase by more than 1.5% or more than 1.5% or more than 0.5%;

(iii) following storage at 5° C. for 9 months, less than 2% or less than 1.5% of the antibody is present as a low molecular weight (LMW) species as measured by UP-SEC, and/or the relative LMW content of the antibody does not increase by more than 1.5% or more than 1.5% or more than 0.5%;

(iv) following storage at 5° C. for 3 months, less than 2% or less than 1.5% or less than 1% of the antibody is present as a low molecular weight (LMW) species as measured by UP-SEC, and/or the relative LMW content of the antibody does not increase by more than 1% or more than 0.5% or more than 0.25%;

(v) following storage at 40° C. for 3 months, less than 8% or less than 7% or less than 6% of the antibody is present as a low molecular weight (LMW) species as measured by UP-SEC, and/or the relative LMW content of the antibody does not increase by more than 8% or more than 7% or more than 6%; and/or (vi) following storage at 40° C. for 1 month, less than 4% or less than 3.5% or less than 3% of the antibody is present as a low molecular weight (LMW) species as measured by UP-SEC, and/or the relative LMW content of the antibody does not increase by more than 3% or more than 2.5% or more than 2.2%.

77. The formulation according to any one of embodiments 70 to 76, fulfilling one or more of the following stability characteristics:

(i) following storage at 25° C. for 12 months, less than 6% or less than 5% or less than 4.5% of the antibody is present as a low molecular weight (LMW) species as measured by UP-SEC, and/or the relative LMW content of the antibody does not increase by more than 5% or more than 4% or more than 3%;

(ii) following storage at 25° C. for 3 months, less than 3% or less than 2% or less than 1.8% of the antibody is present as a low molecular weight (LMW) species as measured by UP-SEC, and/or the relative LMW content of the antibody does not increase by more than 2% or more than 1.5% or more than 1%; and/or (iii) following storage at 25° C. for 1 month, less than 2% or less than 1.5% or less than 1.2% of the antibody is present as a low molecular weight (LMW) species as measured by UP-SEC, and/or the relative LMW content of the antibody does not increase by more than 1% or more than 0.6% or more than 0.4%.

78. The formulation according to any one of embodiments 70 to 77, fulfilling one or more of the following stability characteristics:

(i) following storage at 5° C. for 36 months, at least 55%, at least 60% or at least 65% of the antibody is present as main peak variants, and/or the relative content of main peak variants of the antibody does not decrease by more than 8% or more than 7% or more than 5%, as determined by ion exchange chromatography (IEC);

(ii) following storage at 5° C. for 24 months, at least 55%, at least 60% or at least 65% of the antibody is present as main peak variants, and/or the relative content of main peak variants of the antibody does not decrease by more than 8% or more than 7% or more than 5%, as determined by ion exchange chromatography (IEC);

(iii) following storage at 5° C. for 6 months, at least 60% or at least 65% of the antibody is present as main peak variants, and/or the relative content of main peak variants of the antibody does not decrease by more than 5% or more than 4%, as determined by ion exchange chromatography (IEC);

(iv) following storage at 5° C. for 3 months, at least 60% or at least 65% of the antibody is present as main peak variants, and/or the relative content of main peak variants of the antibody does not decrease by more than 4% or more than 3% or more than 2%, as determined by ion exchange chromatography (IEC);

(v) following storage at 25° C. for 12 months, at least 35% or at least 40% or at least 45% of the antibody is present as main peak variants, and/or the relative content of main peak variants of the antibody does not decrease by more than 35% or more than 30% or more than 25%, as determined by ion exchange chromatography (IEC);

(vi) following storage at 25° C. for 3 months, at least 55% or at least 60% of the antibody is present as main peak variants, and/or the relative content of main peak variants of the antibody does not decrease by more than 15% or more than 10%, as determined by ion exchange chromatography (IEC); and/or (vii) following storage at 25° C. for 1 month, at least 60% or at least 65% of the is present as main peak variants, and/or the relative content of main peak variants of the antibody does not decrease by more than 10% or more than 5%, as determined by ion exchange chromatography (IEC).

79. The formulation according to any one of embodiments 70 to 78, fulfilling one or more of the following stability characteristics:

(i) following storage at 5° C. for 36 months, less than 30% or less than 28% of the antibody is present as acidic peak group variants, and/or the relative content of acidic peak group variants of the antibody does not increase by more than 4% or more than 3% or more than 2%, as determined by ion exchange chromatography (IEC);

(ii) following storage at 5° C. for 24 months, less than 30% or less than 28% of the antibody is present as acidic peak group variants, and/or the relative content of acidic peak group variants of the antibody does not increase by more than 4% or more than 3% or more than 2%, as determined by ion exchange chromatography (IEC);

(iii) following storage at 5° C. for 6 months, less than 30% or less than 28% of the antibody is present as acidic peak group variants, and/or the relative content of acidic peak group variants of the antibody does not increase by more than 4% or more than 3% or more than 2%, as determined by ion exchange chromatography (IEC);

(iv) following storage at 5° C. for 3 months, less than 30% or less than 28% of the antibody is present as acidic peak group variants, and/or the relative content of acidic peak group variants of the antibody does not increase by more than 3% or more than 2% or more than 1%, as determined by ion exchange chromatography (IEC);

(v) following storage at 25° C. for 12 months, less than 50%, less than 45% or less than 40% of the antibody is present as acidic peak group variants, and/or the relative content of acidic peak group variants of the antibody does not increase by more than 30% or more than 25% or more than 20%, as determined by ion exchange chromatography (IEC);

(vi) following storage at 25° C. for 3 months, less than 40% or less than 35% or less than 30% of the antibody is present as acidic peak group variants, and/or the relative content of acidic peak group variants of the antibody does not increase by more than 10% or more than 8% or more than 6%, as determined by ion exchange chromatography (IEC); and/or (vii) following storage at 25° C. for 1 month, less than 35% or less than 30% or less than 28% of the antibody is present as acidic peak group variants, and/or the relative content of acidic peak group variants of the antibody does not increase by more than 4% or more than 3%, as determined by ion exchange chromatography (IEC).

80. The formulation according to any one of embodiments 70 to 79, fulfilling one or more of the following stability characteristics:
   (i) following storage at 5° C. for 36 months, less than 20%, less than 17%, less than 15% or less than 13% of the antibody is present as basic peak group variants, and/or the relative content of basic peak group variants of the antibody does not increase by more than 10% or more than 8% or more than 6%, as determined by ion exchange chromatography (IEC);
   (ii) following storage at 5° C. for 24 months, less than 20%, less than 17%, less than 15% or less than 13% of the antibody is present as basic peak group variants, and/or the relative content of basic peak group variants of the antibody does not increase by more than 10% or more than 8% or more than 6%, as determined by ion exchange chromatography (IEC);
   (iii) following storage at 5° C. for 6 months, less than 15% or less than 10% of the antibody is present as basic peak group variants, and/or the relative content of basic peak group variants of the antibody does not increase by more than 4% or more than 3% or more than 2%, as determined by ion exchange chromatography (IEC);
   (iv) following storage at 5° C. for 3 months, less than 15% or less than 10% of the antibody is present as basic peak group variants, and/or the relative content of basic peak group variants of the antibody does not increase by more than 3% or more than 2%, as determined by ion exchange chromatography (IEC);
   (v) following storage at 25° C. for 12 months, less than 30% or less than 25% or less than 22% of the antibody is present as basic peak group variants, and/or the relative content of basic peak group variants of the antibody does not increase by more than 25% or more than 20% or more than 15%, as determined by ion exchange chromatography (IEC);
   (vi) following storage at 25° C. for 3 months, less than 20% or less than 15% or less than 12% of the antibody is present as basic peak group variants, and/or the relative content of basic peak group variants of the antibody does not increase by more than 9% or more than 7% or more than 5%, as determined by ion exchange chromatography (IEC); and/or
   (vii) following storage at 25° C. for 1 month, less than 15% or less than 10% or less than 9% of the antibody is present as basic peak group variants, and/or the relative content of basic peak group variants of the antibody does not increase by more than 3% or more than 2%, as determined by ion exchange chromatography (IEC).

81. The formulation according to any one of embodiments 70 to 80, fulfilling one or more of the following stability characteristics
   (i) following storage at 5° C. for 36 months, at least 95% or at least 97% of the specific binding activity to IL-23 is measured compared to a reference antibody, wherein the reference antibody has not been stored;
   (ii) following storage at 5° C. for 4, 6, 9, 12, 18 or 24 months, at least 95% or at least 97% of the specific binding activity to IL-23 is measured compared to a reference antibody, wherein the reference antibody has not been stored;
   (iii) following storage at 25° C. for 2, 3, 4, 6, 9, 12, or 18 months, at least 93% or at least 96% of the specific binding activity to IL-23 is measured compared to a reference antibody, wherein the reference antibody has not been stored; and/or
   (iv) following storage at 40° C. for 3, 4 or 6 months, at least 90% or at least 95% of the specific binding activity to IL-23 is measured compared to a reference antibody, wherein the reference antibody has not been stored.

82. The formulation according to one or more of embodiments 1 to 81, wherein the dynamic viscosity measured at 20° C. is ≤30 mPas (mPa·s), ≤25 mPas or ≤20 mPas.

83. The formulation according to one or more of embodiments 1 to 82, wherein the formulation has a conductivity in a range of 0.8 to 5 mS/cm, optionally in a range of 1 to 2 mS/cm or 1.2 to 1.8 mS/cm.

84. The formulation according to one or more of embodiments 1 to 83, wherein the formulation has an osmolality in a range of 225 mOsm/kg to 375 mOsm/kg, such as 250 mOsm/kg to 350 mOsm/kg, 275 mOsm/kg to 330 mOsm/kg or 290 mOsm/kg to 320 mOsm/kg.

85. The formulation according to one or more of embodiments 1 to 84, wherein the formulation is an injectable formulation.

86. The formulation according to embodiment 85, wherein the formulation is suitable for subcutaneous injection.

87. The formulation according to one or more of embodiments 1 to 86, wherein the formulation is not and has not been subjected to a reconstitution step before administration.

88. The formulation according to any one of embodiments 1 to 86, prepared by reconstitution from a lyophilized formulation.

89. A lyophilized formulation of an anti-IL-23p19 antibody, wherein the antibody comprises a light chain amino acid sequence according to SEQ ID NO: 1 and a heavy chain amino acid sequence according to SEQ ID NO: 2, made by lyophilizing the liquid formulation as defined in any one of embodiments 1 to 69, optionally wherein the liquid formulation is an aqueous solution.

90. A lyophilized formulation of an anti-IL-23p19 antibody, wherein the antibody comprises a light chain amino acid sequence according to SEQ ID NO: 1 and a heavy chain amino acid sequence according to SEQ ID NO: 2, providing upon reconstitution the liquid formulation as defined in any one of embodiments 1 to 69 or 82 to 86.

91. A lyophilized formulation comprising
   a) an anti-IL-23p19 antibody, wherein the antibody comprises a light chain amino acid sequence according to SEQ ID NO: 1 and a heavy chain amino acid sequence according to SEQ ID NO: 2, in an amount that upon reconstitution provides an antibody concentration of 150 mg/ml;
   b) a polyol;
   c) a surfactant; and
   d) optionally a buffer.

92. The lyophilized formulation according to embodiment 91, wherein the antibody is risankizumab.

93. The lyophilized formulation according to embodiment 91 or 92, wherein the polyol has one or more of the characteristics as defined in any one of embodiments 6 to 13, optionally wherein the polyol is a sugar, optionally selected from trehalose and sucrose.

94. The lyophilized formulation according to any one of embodiments 91 to 93, wherein the surfactant has one or more of the characteristics as defined in any one of embodiments 22 to 25, optionally wherein the surfactant is a polysorbate.

95. The lyophilized formulation according to any one of embodiments 91 to 94, comprising d) a buffer, wherein the buffer has one or more of the characteristics as defined in any one of embodiments 37 to 40.

96. The lyophilized formulation according to any one of embodiments 91 to 95, wherein the formulation has a pH as defined in any one of embodiments 31 to 36 when reconstituted.

97. A sealed container, optionally, a vial or pre-filled syringe, containing the liquid pharmaceutical formulation according to any one of embodiments 1 to 87.

98. A container, optionally, a sealed vial, containing the lyophilized formulation according to any one of embodiments 88 to 96.

99. The product according to embodiment 97, wherein the container contains 2 ml or less of the liquid formulation, optionally 1.5 ml or less or 1 ml or less of the liquid formulation.

100. The product according to any one of embodiments 97 to 99, comprising a single dose of 150 mg antibody.

101. The formulation according to any one of embodiments 1 to 96 or the product according to any one of embodiments 97 to 100 for therapeutic treatment of a human subject.

102. The formulation according to any one of embodiments 1 to 96 or the product according to any one of embodiments 97 to 100 for use in the treatment of a disease selected from psoriasis and inflammatory bowel disease.

103. The formulation according to any one of embodiments 1 to 96 or the product according to any one of embodiments 97 to 100 for use in the treatment of a disease selected from psoriatic arthritis and Crohn's disease.

104. A stable liquid pharmaceutical formulation comprising
   a) 150 mg/ml of an anti-IL-23p19 antibody, wherein the antibody comprises a light chain amino acid sequence according to SEQ ID NO: 1 and a heavy chain amino acid sequence according to SEQ ID NO: 2;
   b) a tonicity modifier; and
   c) a surfactant,
   wherein the formulation has a pH of 5.5-5.9 and the formulation is isotonic.

105. The stable formulation according to embodiment 104, wherein the antibody is risankizumab.

106. The stable formulation according to embodiment 104 or 105, wherein tonicity modifier is a polyol.

107. The stable formulation according to any one of embodiments 104 to 106, wherein the tonicity modifier is a polyol as defined in any one of the above embodiments 6 to 11.

108. The stable formulation according to any one of embodiments 104 to 107, wherein the concentration of the tonicity modifier has one or more of the characteristics as defined for the polyol in any one of the above embodiments 14 to 21, optionally wherein the tonicity modifier is a polyol as defined therein, optionally a sugar and/or sugar alcohol, optionally selected from trehalose and sucrose.

109. The stable formulation according to any one of embodiments 104 to 108, wherein the surfactant has one or more of the characteristics as defined in any one of the above embodiments 22 to 25, optionally wherein the surfactant is a polysorbate, optionally selected from polysorbate 20 and polysorbate 80.

110. The stable formulation according to any one of embodiments 104 to 109, wherein the concentration of the surfactant in the formulation is as defined in any one of the above embodiments 26 to 30.

111. The stable formulation according to any one of embodiments 104 to 110, wherein the formulation has a pH of in the range of 5.6 to 5.8, optionally wherein the pH of the formulation is 5.7.

112. The stable formulation according to any one of embodiments 104 to 111, comprising d) a buffer, optionally wherein the buffer has one or more of the characteristics as defined in any one of embodiments 37 to 40 and 48.

113. The stable formulation according to embodiment 112, wherein the buffer has a concentration as defined in any one of embodiments 41 to 47.

114. The stable formulation according to any one of embodiments 104 to 113, wherein the formulation is an aqueous formulation.

115. The stable formulation according to any one of embodiments 104 to 114, fulfilling one or more of the stability characteristics as defined in any one of embodiments 71 to 81.

116. The stable formulation according to any one of embodiments 104 to 111 or 114 to 115, wherein the formulation is buffer-free.

117. The stable formulation according to any one of embodiments 104 to 116, wherein the formulation has an osmolality of 290-320 mOsm/kg.

118. The stable formulation according to any one of embodiments 104 to 117, having at least one or at least two of the following characteristics:
   (i) the surfactant is a non-ionic surfactant;
   (ii) the surfactant is a polysorbate, optionally selected from polysorbate 20 and polysorbate 80;
   (iii) wherein the concentration of the surfactant in the formulation is in a range of 0.05 mg/ml to 0.5 mg/ml, optionally within a range of 0.075 mg/ml to 0.4 mg/ml or 0.1 mg/ml to 0.3 mg/ml; and/or
   (iv) it has any one of the characteristics as defined in embodiments 12, 13, or 63 to 68.

119. The stable formulation according to any one of embodiments 104 to 118, prepared by reconstitution from a lyophilized formulation.

120. A lyophilized formulation of an anti-IL-23p19 antibody, wherein the antibody comprises a light chain amino acid sequence according to SEQ ID NO: 1 and a heavy chain amino acid sequence according to SEQ ID NO: 2, made by lyophilizing the liquid formulation as defined in any one of embodiments 104 to 118, optionally wherein the stable liquid formulation is an aqueous solution.

121. A lyophilized formulation of an anti-IL-23p19 antibody, wherein the antibody comprises a light chain amino acid sequence according to SEQ ID NO: 1 and a heavy chain amino acid sequence according to SEQ ID NO: 2, providing upon reconstitution the stable liquid formulation as defined in any one of embodiments 104 to 118.

Numeric ranges are inclusive of the numbers defining the range. The headings provided herein are not limitations of the various aspects or embodiments of this disclosure which can be read by reference to the specification as a whole.

As used in the subject specification, the singular forms "a", "an" and "the" include plural referents unless the context clearly dictates otherwise. The terms "include," "have," "comprise" and their variants are used synonymously and to be construed as non-limiting. Throughout the specification, where compositions are described as comprising components or materials, it is contemplated that the compositions can in embodiments also consist essentially of, or consist of, any combination of the recited components or materials, unless described otherwise. The technology illustratively disclosed herein suitably may be practiced in the absence of any element which is not specifically disclosed herein.

EXAMPLES

The following examples are for illustrative purposes only and are not to be construed as limiting this invention in any manner.

I. Material and Methods

1. Preparation of the Starting Material

The starting material of risankizumab, produced in CHO cells and purified, was adjusted to pH 5.9, where necessary, prior to UF/DF process. At the end, the solution was concentrated and the concentrated starting material was used for preparing formulations according to the subsequent examples.

2. Syringes

Storage of formulations in syringes was essentially performed by using Neopak syringes with rubber stopper of Becton Dickinson (USA). The break loose force, as well as the maximum and average gliding force were measured using such syringes. In embodiments, 1 ml Neopak syringes with a 27 gauge ½ inch needle and a rubber stopper of Becton Dickinson (USA) were used.

II. Example 1: Characterization of the Starting Material

1. Influence of the pH on the Antibody

RALS (right-angle light scattering) measurements were performed for risankizumab at different pH values in a buffer mixture of 10 mM acetate, 10 mM citrate, 10 mM phosphate, 115 mM NaCl. The results are shown in Table 1.

TABLE 1

| Results of the RALS measurements for different pH values. | | | | | | |
|---|---|---|---|---|---|---|
| pH value | 4.5 | 5.0 | 5.5 | 6.0 | 6.5 | 7.0 |
| RALS $T_{onset}$/° C. | 70/71 | 72/72 | 75/75 | 76/76 | 76/75 | 76/76 |

The results show that the onset of unfolding increases when increasing the pH until a plateau is reached. The highest onset temperatures indicating high stability were measured above pH of 5.0 to 7. Therefore, the pH should not be too acidic (<5).

2. Determination of the Buffering Capacity of the Starting Material

The buffer capacity of the antibody starting material was determined inter alia in order to facilitate the pH adjustment of the formulation solutions of the subsequent stability studies and to avoid protein damage. The titration to determine the buffer capacity of the antibody was performed at the following concentrations: 150 mg/mL; 100 mg/mL; 50 mg/mL (twice) and 20 mg/mL.

The dilution was carried out in beakers according to Table 2.

TABLE 2

| Dilution scheme for determination of the buffering capacity of the starting material. | | | |
|---|---|---|---|
| Target concentration [mg/mL] | Volume of initial solution [mL] | Volume MilliQ [mL] | Final volume [mL] |
| 150 | 4.67 | 1.33 | 5.00 |
| 100 | 3.11 | 2.89 | 5.00 |
| 50 | 1.56 | 4.44 | 5.00 |
| 50 | 2.6 | 7.40 | 10.00 |

After dilution, 5 mL of the respective solution was transferred into a 10R glass vial using a volumetric pipette and titrated. 0.2 M NaOH solution was selected for titration (stirring speed 250 rpm). For each antibody concentration the titration was performed and the amount of added NaOH was calculated. The slope and the reciprocal value of the slope as shown in Table 3 were calculated using Excel.

TABLE 3

| Results of the calculation of the slope and the corresponding reciprocal values. | | |
|---|---|---|
| Protein concentration (mg/mL) | Slope | Reciprocal of the slope |
| 20.47 | 1.090000 | 0.92 |
| 50.74 | 0.434821 | 2.30 |
| 50.77 | 0.432378 | 2.31 |
| 102.33 | 0.201703 | 4.96 |
| 152.30 | 0.133120 | 7.51 |

The concentration dependent buffer capacity levels were obtained by drawing the concentration against the reciprocal values of the slope. As a result, a straight line with a slope of 0.0505 and a y-axis intercept of −0.2007 was obtained. The results and the below examples show that risankizumab itself has significant buffering capacity allowing to prepare 150 mg/ml buffer-free formulations according to the present disclosure that do not comprise any further/additional buffer substance.

III. Example 2: Analysis of Different pH Values and Buffer Substances

1. Comparison of Acetate and Succinate Buffer Systems with Different pH Values for the Assessment of Stability of 150 mg/mL Formulations 1.1. Preparation of Formulations The formulations shown in Table 4 were prepared and analyzed:

TABLE 4

| Composition of the analyzed formulations. | | | | | | |
|---|---|---|---|---|---|---|
| Formulation | pH | Protein concentration mg/mL | buffer | Excipient 1 | Excipient 2 | Excipient 3 |
| F1 | 6.2 | 150 | 4.4 mM succinate | 200 mM sorbitol | — | 0.02% PS20 |
| F2 | 5.9 | 150 | 4.4 mM succinate | 200 mM sorbitol | — | 0.02% PS20 |

TABLE 4-continued

Composition of the analyzed formulations.

| Formulation | pH | Protein concentration mg/mL | buffer | Excipient 1 | Excipient 2 | Excipient 3 |
|---|---|---|---|---|---|---|
| F3 | 5.7 | 150 | 10 mM acetate | 190 mM sorbitol | — | 0.02% PS20 |
| F4 | 5.7 | 150 | 10 mM acetate | 115 mM sorbitol | 50 mM L-arginine HCl | 0.02% PS20 |
| F5 | 5.7 | 150 | 10 mM acetate | 150 mM sorbitol | 50 mM L-proline | 0.02% PS20 |

0.02% PS20 corresponds to 0.2 mg/mL PS20.

Samples were taken within a period of 18 months (0, 3, 6, 8, 12 and 18 months). Storage conditions were: 5° C. and 25° C./60% relative humidity. Each formulation was filled into Neopak syringes. The filling within a laminar flow was set to a volume of 1.1 mL. The syringes were closed with a stopper and analyzed visually for particles before storage. Afterwards, the syringes were stored hanging in syringe-trays at the respective temperature. In parallel, the buffer solutions were stored as controls. After preparing the formulations, each solution was sterile filtered and the prepared formulations were stored in syringes (Neopak syringes of Becton Dickinson (USA).

1.2. Analytics

For analysis of the samples, inter alia high pressure size exclusion chromatography (HP-SEC) and ultra-performance size exclusion chromatography (UP-SEC) were performed and the turbidity at 860 nm (also referred to as opalescence) was measured. The syringeability of the formulations stored in syringes (Neopak) was analyzed by measuring the mechanical forces that are required to release/inject the formulation. A pressure test was performed with a speed of 379.2 mm/min (5 sec). The viscosity of the formulations was measured at 20° C. using the HAAKE RheoStress 600 with a C35/1 rotor. Double measurements were performed.

Further details on the utilized analysis methods are described below.

1.3. Results 1.3.1. Measurement of the Monomer Content

For determining the monomer content the samples were analyzed by HP-SEC and UP-SEC.

HP-SEC Analysis

The results obtained by HP-SEC analysis at a storage temperature of 25° C. and 5° C. are shown in Table 5:

TABLE 5

Results HP-SEC monomer in % analysis over 18 months storage at different temperatures in syringes.

| Time | Temp-erature | F1 in % | F2 in % | F3 in % | F4 in % | F5 in % |
|---|---|---|---|---|---|---|
| Initial | 25° C. | 95.8 | 96.4 | 96.6 | 96.7 | 96.5 |
| 3 months | | 94.5 | 95.1 | 95.4 | 96.1 | 95.6 |
| 6 months | | 94.4 | 94.9 | 95.1 | 95.8 | 95.4 |
| 8 months | | 93.7 | 94.3 | 94.6 | 95.3 | 94.9 |
| 12 months | | 92.9 | 93.5 | 93.9 | 94.8 | 94.3 |
| 18 months | | 91.1 | 92.4 | 92.8 | 94.0 | 93.4 |
| Initial | 5° C. | 95.8 | 96.4 | 96.6 | 96.7 | 96.5 |
| 6 months | | 95.6 | 96.2 | 96.4 | 96.6 | 96.4 |
| 8 months | | 95.2 | 95.9 | 96.1 | 96.4 | 96.2 |
| 18 months | | 93.4 | 94.7 | 95.1 | 95.8 | 95.4 |

Over a storage time of 18 months at 25° C. the monomer content was between 91-94%. The strongest decrease was measured for F1 with −5%; the lowest decrease was measured with −3% for formulation 4 and 5 tested in this example. Over a storage time of 18 months at 5° C. the monomer content was between 93-96%. The strongest decrease was measured for F1 with −2.4%; the lowest decrease was measured with −0.9% and −1.1% for formulation 4 and 5.

UP-SEC Analysis

The results of the UP-SEC analysis were analogous to those of the HP-SEC and thus confirm these results.

TABLE 5a

Results UP-SEC monomer in % analysis over 18 months storage at different temperatures in syringes.

| Time | Temp-erature | F1 in % | F2 in % | F3 in % | F4 in % | F5 in % |
|---|---|---|---|---|---|---|
| Initial | 25° C. | 94.9 | 95.4 | 95.5 | 95.7 | 95.4 |
| 3 months | | 93.5 | 94.2 | 94.4 | 95.0 | 94.6 |
| 8 months | | 93.6 | 92.7 | 93.0 | 93.6 | 93.3 |
| 12 months | | 90.6 | 91.2 | 91.4 | 92.1 | 91.7 |
| 18 months | | 88.4 | 89.4 | 89.8 | 90.6 | 90.3 |
| Initial | 5° C. | 94.9 | 95.4 | 95.5 | 95.7 | 95.4 |
| 8 months | | 94.6 | 95.3 | 95.5 | 95.7 | 95.7 |
| 18 months | | 92.7 | 93.8 | 94.2 | 94.7 | 94.4 |

Over a storage time of 18 months at 25° C. the monomer content (UP-SEC) was between 88-91%. The strongest decrease was measured for F1 with −6.4%; the lowest decrease was measured with −5.1% and −5.4% for formulation 4 and 5. Over a storage time of 18 months at 5° C. the monomer content (UP-SEC) was between 93-95%. The strongest decrease was measured for F1 with −2.2%; the lowest decrease was measured with −1% for formulation 4 and 5.

Results and Discussion

All tested formulations were overall stable in view of the monomer content, showing that these formulations are stable at 5° C. and 25° C. over long storage times up to 18 months.

1.3.2. Measurement of the HMW Content

For determining the HMW content the samples were analyzed by HP-SEC and UP-SEC.

HP-SEC Analysis

The results obtained by HP-SEC analysis at a storage temperature of 25° C. and 5° C. are shown in Table 6.

TABLE 6

Results HP-SEC HMW content in % at different storage
temperatures over 18 months in syringes.

| Time | Temp-erature | F1 in % | F2 in % | F3 in % | F4 in % | F5 in % |
|---|---|---|---|---|---|---|
| Initial | 25° C. | 4.0 | 3.4 | 3.2 | 3.1 | 3.3 |
| 3 months | | 5.1 | 4.5 | 4.3 | 3.6 | 4.0 |
| 6 months | | 5.1 | 4.6 | 4.4 | 3.6 | 4.1 |
| 8 months | | 5.7 | 5.1 | 4.8 | 4.0 | 4.5 |
| 12 months | | 6.2 | 5.5 | 5.2 | 4.2 | 4.8 |
| 18 months | | 7.6 | 6.4 | 5.9 | 4.7 | 5.3 |
| Initial | 5° C. | 4.0 | 3.4 | 3.2 | 3.1 | 3.3 |
| 6 months | | 4.2 | 3.6 | 3.4 | 3.2 | 3.4 |
| 8 months | | 4.6 | 3.9 | 3.7 | 3.4 | 3.7 |
| 18 months | | 6.2 | 5.0 | 4.5 | 3.9 | 4.3 |

Over a storage time of 18 months at 25° C. the HMW species were increased by 2-4%. The strongest increase was measured for F1 with +3.6%; the lowest increase was measured with +1.6% and +2.0% for formulation 4 and 5. Over a storage time of 18 months at 5° C. the HMW species were increased by 1-2%. The strongest increase was measured for F1 with +2.2%; the lowest increase was measured with +0.8% and +1.0% for formulation 4 and 5.

UP-SEC Analysis

The results of the UP-SEC analysis were analogous to those of the HP-SEC and thus confirm these results.

TABLE 6a

Results UP-SEC BMW content in % at different storage
temperatures over 18 months in syringes.

| Time | Tem-perature | F1 in % | F2 in % | F3 in % | F4 in % | F5 in % |
|---|---|---|---|---|---|---|
| Initial | 25° C. | 3.9 | 3.4 | 3.2 | 3.1 | 3.3 |
| 3 months | | 5.1 | 4.5 | 4.2 | 3.6 | 3.9 |
| 8 months | | 4.0 | 5.0 | 4.8 | 4.0 | 4.4 |
| 12 months | | 6.0 | 5.4 | 5.0 | 4.2 | 4.7 |
| 18 months | | 7.4 | 6.4 | 6.0 | 4.9 | 5.5 |
| Initial | 5° C. | 3.9 | 3.4 | 3.2 | 3.1 | 3.3 |
| 8 months | | 4.4 | 3.7 | 3.5 | 3.3 | 3.5 |
| 18 months | | 5.8 | 4.7 | 4.3 | 3.8 | 4.1 |

Over a storage time of 18 months at 25° C. the HMW were increased by 2-3.5%. The strongest increase was measured for F1 with +3.5%; the lowest increase was measured with +1.8% and +2.2% for formulation 4 and 5. Over a storage time of 18 months at 5° C. the HMW were increased by 0.7-1.9%. The strongest increase was measured for F1 with +1.9%; the lowest increase was measured with +0.7% and +0.8% for formulation 4 and 5.

Results and Discussion

All tested formulations were overall stable in view of the HMW content, showing that various formulations according to the present disclosure are stable at 5° C. and 25° C. over long storage times up to 18 months.

1.3.3. Turbidity Measurements

TABLE 7

Results of the turbidity at 860 nm in FNU over 18
months at different storage temperatures in syringes.

| Time | Tem-perature | F1 in FNU | F2 in FNU | F3 in FNU | F4 in FNU | F5 in FNU |
|---|---|---|---|---|---|---|
| Initial | 25° C. | 6 | 6 | 5 | 8 | 5 |
| 3 months | | 6 | 6 | 6 | 8 | 5 |

TABLE 7-continued

Results of the turbidity at 860 nm in FNU over 18
months at different storage temperatures in syringes.

| Time | Tem-perature | F1 in FNU | F2 in FNU | F3 in FNU | F4 in FNU | F5 in FNU |
|---|---|---|---|---|---|---|
| 6 months | | 6 | 5 | 4 | 7 | 5 |
| 8 months | | 7 | 7 | 6 | 9 | 7 |
| 12 months | | 8 | 7 | — | 9 | 6 |
| 18 months | | 9 | 7 | 7 | 10 | 7 |
| Initial | 5° C. | 6 | 6 | 5 | 8 | 5 |
| 6 months | | 6 | 5 | 4 | 8 | 4 |
| 8 months | | 6 | 5 | 4 | 7 | 4 |
| 18 months | | 7 | 6 | 5 | 9 | 5 |

The turbidity was measured at a wavelength of 860 nm, showing an increase in Formazine Nephelometric Units (FNU) of 1 to 3 during the storage time of 18 months at 25° C.

Formulation 1 had the strongest increase in 3 FNU and formulation 2 the smallest increase in 1 FNU. Formulation 4 containing L-arginine had the highest turbidity from the beginning on.

The turbidity was measured at a wavelength of 860 nm, showing an increase of 0-1 FNU during the storage time of 18 months at 5° C.

Results and Discussion

The turbidity measurement show that storage in a fridge over 18 months does not result in relative changes in turbidity. Formulation 4 containing L-arginine had the highest turbidity rendering arginine-free formulations more advantageous.

1.3.4. Conductivity Measurements

The conductivity of the formulations was measured.

TABLE 8

Results of the conductivity measurements in mS/cm at a
storage temperature at 25° C. for up to 18 months.

| Time | Tem-perature | F1 | F2 | F3 | F4 | F5 |
|---|---|---|---|---|---|---|
| Initial | 25° C. | 1.25 | 1.37 | 1.53 | 3.96 | 1.54 |
| 3 months | | 1.08 | 1.27 | 1.40 | 3.71 | 1.41 |
| 6 months | | 1.29 | 1.34 | 1.52 | 3.85 | 1.52 |
| 8 months | | 1.14 | 1.22 | 1.35 | 3.66 | 1.42 |
| 12 months | | 1.18 | 1.23 | 1.43 | 3.61 | 1.43 |
| 18 months | | 1.15 | 1.26 | 1.39 | 4.05 | 1.38 |
| Initial | 5° C. | 1.25 | 1.37 | 1.53 | 3.96 | 1.54 |
| 6 months | | 1.25 | 1.35 | 1.48 | 3.92 | 1.54 |
| 8 months | | 1.12 | 1.18 | 1.36 | 3.67 | 1.38 |
| 18 months | | 1.07 | 1.14 | 1.29 | 3.99 | 1.36 |

Results and Discussion

The conductivity remained constant for all 5 formulations over a storage time of 18 months and at a temperature of 5° C. and 25° C. While the conductivity of F1, F2, F3 and F5 has a value between 1 to 2 mS/cm, the L-arginine containing formulation F4 had a relatively high conductivity of just below 4 mS/cm.

1.4. Further Analytics and Results

In addition, further analytics were performed for the five formulations tested (storage times and temperature were as described above) with the following results.

The pH value remained essentially constant over the storage time of 18 months and at the different storage temperatures tested. Measured pH values were thus in a range from 5.7-6.3.

The osmolality remained essentially constant over the storage time of 18 months and at the different storage temperatures tested. The tested values ranged from 296-333 mOsm/kg.

The dynamic viscosity at 20° C. remained essentially constant over the storage time of 18 months and at the different storage temperatures tested. The dynamic viscosity was in a range of 10-14 mPas.

The protein concentration remained essentially constant over the storage time of 18 months and at the different storage temperatures tested. Small deviations of protein concentration are due to analytical variations, leading to ranges of 148-159 mg/mL.

The HP-SEC fragments contents remained essentially constant over the storage time of 18 months and at the different storage temperatures tested. The fragments content was in a range of 0.2-1.4%. The UP-SEC LMW contents remained essentially constant over the storage time of 18 months and at the different storage temperatures tested. In particular, a low increase of 3% was measured for 25° C. and 0.1-0.3% for 5° C. over 18 months. The LMW content was in a range of 1.0-4.5%.

The weak cation exchange (WCX) main peak, acidic peak group (APG) and basic peak group (BPG) content remained constant over the storage time of 18 months at 5° C. No differences between the formulations were observed regarding the main peak, APG and BPG.

The hydrophobic interaction chromatography (HIC) main peak content remained essentially constant over the storage time of 12 months at 25° C. or 8 months at 5° C. The post peak increased by about 2-3% over at the storage temperature and time. The pre-peak was slightly increased by 5-7% over 12 months at 25° C. and did not increase at 5° C. over 8 months. No differences between the formulations were observed regarding the main peak, post peak and pre-peak.

The specific binding activity remained essentially constant over the storage time of 18 months and at the different storage temperatures tested with only minimal reduction of 3% and 1-2% for 25° C. and 5° C., respectively, for 18 months. The specific binding activity was in a range of 96-101%.

No visible particles were observed.

1.5. Summary of Results

All 5 formulations were stable over 18 months storage time at 25° C. and 5° C. Formulation 4, however, comprises an additional auxiliary agent. Formulation 3 was stable and did not have an additional auxiliary agent in contrast to the arginine-containing formulation F4. At a pH of about 5.7 less aggregate formation was observed.

2. Comparison of Acetate and Succinate Buffer Systems with Different pH Values in Free/Thaw Experiments It was analyzed whether freezing and thawing of a 150 mg/mL formulation has an influence on the product quality of risankizumab. Therefore, 3 formulations were filled in mini bags having a volume of 10 mL or 14 mL for the initial value, followed by freezing at –40° C. Furthermore, one bag was stored at 2-8° C. The storage time for both conditions (–40° C. and 2-8° C.) was 3 weeks, The freezing was performed by a controlled freezing process. Afterwards, the bags were transferred into a –40° C. freezer and kept frozen for the indicated storage times.

2.1. Preparation of Formulations

Each freeze/thaw cycle comprised freezing at –40° C. in a lyophilizer and subsequent transfer into a –40° C. freezer and thawing in a lyophilizer at a maximal thawing rate of 20° C./min until room temperature after 3 weeks. The tested formulations are shown in Table 9.

TABLE 9

Composition of the formulations.

| For-mula-tion | pH | Protein con-centration mg/mL | buffer | Excipient 1 | Excipient 2 |
|---|---|---|---|---|---|
| F1 | 6.2 | 150 | 10 mM succinate | 185 mM sorbitol | 0.02 w % PS20 |
| F2 | 5.7 | 150 | 10 mM acetate 6.5 mM succinate | 185 mM sorbitol | 0.02 w % PS20 |
| F3 | 5.7 | 150 | 10 mM acetate 6.5 mM succinate | 160 mM trehalose | 0.02 w % PS20 |

The starting material was stored at 2-8° C. in a fridge until use. The bags ("Mini Flexboy Bags") having a sample volume of 10 mL were frozen using a lyophilizer with a controlled freezing rate of 0.5° C./min until reaching a temperature of –40° C.

2.2. Analytics

The samples were directly before analysis thawed in a controlled manner using a lyophilizer. To measure the protein stability HP-SEC analysis was performed and the binding activity was measured. The turbidity was measured at 860 nm and at 400-600 nm. Further details on the utilized analysis methods are described below.

2.3. Results 2.3.1. Measurement of the Monomer and HMW Content

For determining the stability of the formulations, HP-SEC and UP-SEC analyses were performed, showing the monomer and HMW contents. Following results were obtained:

TABLE 10

Results HP-SEC monomer content in % after 3 weeks storage (frozen at –40° C. and at 2-8° C.) and initial values.

| | F1-Bag 1% | F1-Bag 2% | F2-Bag 1% | F2-Bag 2% | F3-Bag 1% | F3-Bag 2% |
|---|---|---|---|---|---|---|
| Initial | 98.7 | 98.6 | 98.9 | 98.9 | 98.9 | 98.9 |
| 3 weeks 5° C. | 98.3 | 98.3 | 98.7 | 98.7 | 98.7 | 98.7 |
| 3 weeks –40° C. | 98.6 | 98.6 | 98.9 | 98.9 | 98.9 | 98.9 |

The UP-SEC measurements confirm the results of the HP-SEC measurement.

TABLE 10a

Results UP-SEC monomer content in % after 3 weeks storage (frozen at –40° C. and at 2-8° C.) and initial values.

| | F1-Bag 1 % | F1-Bag 2% | F2-Bag 1% | F2-Bag 2% | F3-Bag 1% | F3-Bag 2% |
|---|---|---|---|---|---|---|
| Initial | 97.0 | 97.0 | 97.4 | 97.5 | 97.4 | 97.4 |
| 3 weeks 5° C. | 97.0 | 97.0 | 97.4 | 97.4 | 97.3 | 97.3 |
| 3 weeks –40° C. | 97.0 | 97.0 | 97.4 | 97.5 | 97.4 | 97.4 |

The remaining antibody content missing to 100% was present as HMW species.

Results and Discussion

Overall, the results of the HP-SEC analysis demonstrate stability for all formulations, showing that the formulations allow for freeze/thaw cycle. Some formulations showed better results regarding a higher monomer content and less HMW species.

2.3.2. Measurement of the Binding Activity

The binding activity against rhIL-23 was measured utilizing surface plasmon resonance (Biacore) measurements. The binding activity is overall the same in all formulations, demonstrating applicability of the formulations. In particular, the binding activity was measured to be in a range between 95 to 110% and the specific binding activity was about 100%. The 3 weeks of storage in a frozen state or at 2-8° C. did not change the binding activity.

2.3.3. Measurement of the Viscosity

Another important parameter of protein formulations is the viscosity, which preferably is not too high in order to allow the formulation to be injected (e.g. pass a needle without excessive use of force). Therefore, the dynamic viscosity was measured.

The dynamic viscosity is very similar for F1, F2 and F3 being in a range of 8.7 to 10 mPas.

2.4. Further Analytics and Results

In addition, further analytics were performed for the three formulations tested with the following results.

The sub-visible particle content ($\geq 25$ μm, $\geq 10$ μm, $\geq 5$ μm) remained essentially constant over 3 weeks at 5° C. or at −40° C. including a freeze/thaw cycle. The sum of counted particles was essentially the same for all three formulations.

The osmolality remained essentially constant over 3 weeks at 5° C. or at −40° C. including a freeze/thaw cycle. The tested values ranged from 299-321 mOsm/kg for 150 mg/mL formulations.

The turbidity at 860 nm and 400-600 nm remained essentially constant over 3 weeks at 5° C. or at −40° C. including a freeze/thaw cycle. The tested values ranged from 2-7 FNU at 860 nm and 4-13 FNU at 400-600 nm.

The pH value remained essentially constant over 3 weeks at 5° C. or at −40° C. including a freeze/thaw cycle. Measured pH values were thus in a range from 5.7-6.2.

The conductivity remained essentially constant over 3 weeks at 5° C. or at −40° C. including a freeze/thaw cycle. Measured conductivity were thus in a range from 1.3-2.5 mS.

The protein concentration remained essentially constant over 3 weeks at 5° C. or at −40° C. including a freeze/thaw cycle. Small deviations of protein concentration are due to analytical variations, leading to ranges of 149-157 mg/mL for initial protein contents of 150 mg/mL.

The hydrophobic interaction chromatography (HIC) main peak content remained essentially constant over 3 weeks at 5° C. or at −40° C. including a freeze/thaw cycle. The HIC main peak values ranged from 97.1-97.7%. The post peak and pre peak remained essentially constant over 3 weeks at 5° C. or at −40° C. including a freeze/thaw cycle.

The weak cation exchange (WCX) chromatography main peak content remained essentially constant over 3 weeks at 5° C. or at −40° C. including a freeze/thaw cycle. The WCX main peak values range from 72.5-73.8%. The acidic peak group (APG) and basic peak group (BPG) remained essentially constant over 3 weeks at 5° C. or at −40° C. including a freeze/thaw cycle. No differences between the formulations were observed regarding main peak, APG and BGP.

The capillary gel electrophoresis (CGE) analysis showed essentially constant values over 3 weeks at 5° C. or at −40° C. including a freeze/thaw cycle. The non-reduced main peak contents ranged from 96.7-97.6%.

2.5. Summary of the Results

The results of the present example demonstrate stability of risankizumab provided in different 150 mg/mL formulations over freeze/thaw cycle. The single freeze/thaw cycle with a storage time of 3 weeks at −40° C. or at 2-8° C. for 3 weeks had no influence on the product quality of risankizumab. Therefore, 150 mg/mL formulations are a suitable concentration. A pH of 5.7 appeared to have performed slightly better compared to other pH values.

3. Comparison of Acetate and Succinate Buffer Systems with Different pH Values

A particularly suitable pH is in the range of 5.2 to 6.2 such as 5.5 to 6.2 or about 5.7. A higher pH can lead to increased protein aggregation, measured by SEC. A lower pH can lead to chemical degradation. In prior studies, sorbitol was used to adjust the tonicity. In the present example, trehalose and mannitol were used instead of sorbitol to adjust the tonicity. Seven sorbitol-free formulations were chosen and tested at following three conditions (i) 5° C. for 18 months, r.h. not monitored; (ii) 25° C./60% r.h. for 18 months and (iii) 40° C./75% r.h. for 6 months.

The compositions of formulation 1-7 are depicted below in Table 11.

TABLE 11

| Composition of the analyzed formulations. | |
| --- | --- |
| Formulation | Composition |
| F1 | 150 mg/mL risankizumab, 10 mM acetate + 100 mM trehalose + 100 mM mannitol + 0.2 mg/mL PS20, pH 5.7 |
| F2 | 150 mg/mL risankizumab, 10 mM acetate + 200 mM trehalose + 0.2 mg/mL PS20, pH 5.7 |
| F3 | 150 mg/mL risankizumab, 10 mM acetate + 100 mM trehalose + 50 mM L-arginine HCl + 0.2 mg/mL PS20, pH 5.7 |
| F4 | 150 mg/mL risankizumab, 4.4 mM succinate + 200 mM trehalose + 0.2 mg/mL PS20, pH 6.0 |
| F5 | 150 mg/mL risankizumab, 4.4 mM succinate + 100 mM trehalose + 50 mM L-arginine HCl + 0.2 mg/mL PS20, pH 6.0 |
| F6 | 150 mg/mL risankizumab, 4.4 mM succinate + 100 mM trehalose + 100 mM mannitol + 0.2 mg/mL PS20, pH 6.0 |
| F7 | 150 mg/mL risankizumab, 200 mM trehalose + 0.2 mg/mL PS20, pH 5.7 (buffer free) |

The formulations and formulation buffers were sterile-filtered (filter type 0.22 μm) and filled under laminar flow with a fill volume of 1.04 mL in syringes (Neopak). The formulations were prepared by mixing the starting material with a concentration solution comprising the auxiliary agents (excipients, buffer, etc.). The filled syringes were stored horizontally in rondotrays protected from light using cardboard boxes at 2-8° C. Following packing materials were used:

Neopak syringe (1 ml syringe with 27 gauge ½ inch needle)
Rubber stopper
Rondotray 3.1. Analytics For analysis of the samples, HP-SEC and UP-SEC were performed and the turbidity (also referred to as opalescence) was measured. Following devices were used for analysis:

UPLC, UPSEC: UPLC 29/31 Waters ACQUITY, Waters, MA

HPLC, WCX/SEC: HPLC 82/83/107 Waters ALLIACE, Waters, MA

Particle count/size by MFI: Micro Flow Imagine, 5200 BOT A/B (Roboter), Protein Simple, GER Osmometer: Osmomat 3000 Gonotec GmbH, GER pH-meter: SevenGo, Mettler Toledo, GER Turbidity photometer: 2100AN Turbidimeter, Hach-Lange GmbH, GER Protein concentration by Solo VPE: Solo VPE, C. Technologies, Inc., NJ Biacore: Biacore T200, GE Healthcare Life Science, UK Tensile and Compression testing machine: Zwick 2.5TS/N 21159574 Zwick, Germany Further details on the utilized analysis methods are described below.

3.2. Results 3.2.1. Measurement of the Monomer Content

UP-SEC and HP-SEC were used to determine the loss of monomer content. Monomer content is a key quality attribute of protein stability and quality during stress-induced storage. The following table shows the results of the UP-SEC measurement.

TABLE 12

| | | Monomer content measured by UP-SEC [%] of seven formulations stored at 5° C., 25° C. and 40° C.. | | | | | | |
|---|---|---|---|---|---|---|---|---|
| Storage condition | Storage time, months | F1 | F2 | F3 | F4 | F5 | F6 | F7 |
| 5° C. | 0 | 98.2 | 98.2 | 98.2 | 97.9 | 98.1 | 97.9 | 98.1 |
| | 4 | 97.8 | 97.8 | 98.0 | 97.5 | 97.8 | 97.5 | 97.8 |
| | 6 | 97.6 | 97.6 | 97.8 | 97.3 | 97.7 | 97.3 | 97.6 |
| | 9 | 97.5 | 97.5 | 97.7 | 97.0 | 97.5 | 97.0 | 97.4 |
| | 12 | 97.5 | 97.5 | 97.8 | 97.1 | 97.5 | 97.1 | 97.5 |
| | 18 | — | 97.3 | — | — | — | — | — |
| 25° C. | 0 | 98.2 | 98.2 | 98.2 | 97.9 | 98.1 | 97.9 | 98.1 |
| | 2 | 97.1 | 97.1 | 97.4 | 96.8 | 97.3 | 96.8 | 97.1 |
| | 4 | 96.5 | 96.5 | 96.9 | 96.3 | 96.8 | 96.2 | 96.5 |
| | 6 | 95.8 | 95.8 | 96.2 | 95.6 | 96.2 | 95.5 | 95.8 |
| | 9 | 95.1 | 95.1 | 95.5 | 94.9 | 95.5 | 94.9 | 95.2 |
| | 12 | 94.7 | 94.7 | 95.0 | 94.5 | 95.1 | 94.5 | 94.7 |
| | 18 | — | 93.3 | — | — | — | — | — |
| 40° C. | 0 | 98.2 | 98.2 | 98.2 | 97.9 | 98.1 | 97.9 | 98.1 |
| | 2 | 92.6 | 92.7 | 92.4 | 92.6 | 92.4 | 92.4 | 92.8 |
| | 4 | 88.4 | 88.5 | 87.7 | 88.6 | 88.2 | 88.5 | 88.8 |
| | 6 | 84.3 | 84.4 | 83.6 | 84.9 | 84.3 | 84.7 | 84.7 |

HP-SEC confirms the results of UP-SEC. Compared to UP-SEC, no additional information were generated by HP-SEC.

Results and Discussion

All analyzed formulations were stable at the tested conditions.

3.2.2. Measurement of the HMW Level

UP-SEC and HP-SEC were used to determine levels of HMW formation. The following table shows the results of the UP-SEC measurement. The HMW content correlates with the monomer content. Loss of monomer leads to increase of HMW.

TABLE 13

| | | HMW measured by UP-SEC [%] of seven formulations stored at 5° C., 25° C. and 40° C.. | | | | | | |
|---|---|---|---|---|---|---|---|---|
| Storage condition | Storage time, months | F1 | F2 | F3 | F4 | F5 | F6 | F7 |
| 5° C. | 0 | 1 3 | 1.3 | 1.2 | 1.6 | 1.4 | 1.6 | 1.4 |
| | 4 | 1.5 | 1.6 | 1.4 | 1.9 | 1.5 | 1.9 | 1.6 |
| | 6 | 1.6 | 1.7 | 1.5 | 2.0 | 1.6 | 2.0 | 1.7 |
| | 9 | 1.8 | 1.8 | 1.6 | 2.3 | 1.8 | 2.3 | 1.9 |
| | 12 | 1.9 | 1.9 | 1.6 | 2.3 | 1.8 | 2.3 | 1.9 |
| | 18 | — | 2.0 | — | — | — | — | — |

TABLE 13-continued

| | Storage | | | | | | | |
|---|---|---|---|---|---|---|---|---|
| | time, | | | | | | | |
| Storage | months | F1 | F2 | F3 | F4 | F5 | F6 | F7 |
| condition | | | | | | | | |
| 25° C. | 0 | 0 | 1.3 | 1.3 | 1.2 | 1.6 | 1.4 | 1.6 |
| | 2 | 2.0 | 2.0 | 1.7 | 2.4 | 1.8 | 2.4 | 2.0 |
| | 4 | 2.2 | 2.2 | 1.8 | 2.5 | 1.9 | 2.5 | 2.2 |
| | 6 | 2.4 | 2.4 | 2.0 | 2.7 | 2.1 | 2.8 | 2.4 |
| | 9 | 2.7 | 2.7 | 2.2 | 3.0 | 2.3 | 3.0 | 2.7 |
| | 12 | 2.8 | 2.8 | 2.3 | 3.2 | 2.4 | 3.2 | 2.9 |
| | 18 | — | 3.2 | — | — | — | — | — |
| 40° C. | 0 | 0 | 1.3 | 1.3 | 1.2 | 1.6 | 1.4 | 1.6 |
| | 2 | 3.7 | 3.6 | 3.4 | 3.9 | 3.4 | 4.0 | 3.5 |
| | 4 | 5.2 | 5.1 | 5.1 | 5.3 | 4.8 | 5.4 | 4.9 |
| | 6 | 6.7 | 6.7 | 6.5 | 6.8 | 6.2 | 6.8 | 6.4 |

*HMW measured by UP-SEC [%] of seven formulations stored at 5° C., 25° C. and 40° C..*

HP-SEC confirms the results of UP-SEC. Compared to UP-SEC, no additional information were generated by HP-SEC.

Results and Discussion

Overall, all formulations were stable with low amounts of HMW species even after storage at 40° C.

3.2.3. Measurement of the LMW Level

UP-SEC was used to determine levels of LMW formation. The following table shows the results of the UP-SEC measurement.

TABLE 14

| | storage | | | | | | | |
|---|---|---|---|---|---|---|---|---|
| | time, | | | | | | | |
| Storage | months | F1 | F2 | F3 | F4 | F5 | F6 | F7 |
| condition | | | | | | | | |
| 5° C. | 0 | 0.5 | 0.5 | 0.5 | 0.5 | 0.5 | 0.6 | 0.6 |
| | 4 | 0.6 | 0.6 | 0.7 | 0.6 | 0.7 | 0.7 | 0.7 |
| | 6 | 0.7 | 0.7 | 0.7 | 0.7 | 0.7 | 0.7 | 0.7 |
| | 9 | 0.7 | 0.7 | 0.7 | 0.7 | 0.7 | 0.7 | 0.7 |
| | 12 | 0.6 | 0.6 | 0.6 | 0.6 | 0.6 | 0.6 | 0.6 |
| | 18 | — | 0.7 | — | — | — | — | — |
| 25° C. | 0 | 0.5 | 0.5 | 0.5 | 0.5 | 0.5 | 0.6 | 0.6 |
| | 2 | 0.9 | 0.9 | 1.0 | 0.9 | 0.9 | 0.9 | 0.9 |
| | 4 | 1.3 | 1.3 | 1.4 | 1.3 | 1.3 | 1.3 | 1.3 |
| | 6 | 1.8 | 1.7 | 1.8 | 1.7 | 1.7 | 1.7 | 1.7 |
| | 9 | 2.2 | 2.2 | 2.4 | 2.1 | 2.2 | 2.1 | 2.2 |
| | 12 | 2.4 | 2.4 | 2.6 | 2.3 | 2.5 | 2.4 | 2.4 |
| | 18 | — | 3.6 | — | — | — | — | — |
| 40° C. | 0 | 0.5 | 0.5 | 0.5 | 0.5 | 0.5 | 0.6 | 0.6 |
| | 2 | 3.7 | 3.7 | 4.3 | 3.5 | 4.1 | 3.5 | 3.7 |
| | 4 | 6.4 | 6.4 | 7.2 | 6.1 | 7.0 | 6.1 | 6.4 |
| | 6 | 8.9 | 8.9 | 9.9 | 8.4 | 9.5 | 8.5 | 8.9 |

*LMW content measured by UP-SEC [%] of seven formulations stored at 5° C., 25° C. and 40° C..*

Results and Discussion

Overall, all formulations were stable with low amounts of LMW species even after storage at 40° C.

3.2.4. Measurement of the LMW Level

For assessing the stability of the formulations, the LMW content was also measured by HP-SEC analysis. The results of this analysis are shown below.

TABLE 15

| Storage condition | Storage time, months | F1 | F2 | F3 | F4 | F5 | F6 | F7 |
|---|---|---|---|---|---|---|---|---|
| | | LMW content measured by HP-SEC [%] of seven formulations stored at 5° C., 25° C. and 40° C.. | | | | | | |
| 5° C. | 0 | 0.2 | 0.2 | 0.2 | 0.2 | 0.2 | 0.2 | 0.2 |
| | 4 | 0.3 | 0.3 | 0.3 | 0.3 | 0.3 | 0.3 | 0.3 |
| | 6 | 0.3 | 0.3 | 0.3 | 0.3 | 0.3 | 0.3 | 0.3 |
| | 9 | 0.3 | 0.3 | 0.3 | 0.3 | 0.3 | 0.3 | 0.3 |
| | 12 | 0.4 | 0.3 | 0.3 | 0.3 | 0.3 | 0.3 | 0.3 |
| | 18 | — | 0.3 | — | — | — | — | — |
| 25° C. | 0 | 0.2 | 0.2 | 0.2 | 0.2 | 0.2 | 0.2 | 0.2 |
| | 2 | 0.4 | 0.4 | 0.4 | 0.4 | 0.4 | 0.4 | 0.4 |
| | 4 | 0.5 | 0.5 | 0.6 | 0.5 | 0.5 | 0.5 | 0.6 |
| | 6 | 0.6 | 0.6 | 0.6 | 0.6 | 0.6 | 0.6 | 0.6 |
| | 12 | 1.0 | 1.0 | 1.0 | 1.0 | 1.0 | 1.0 | 1.0 |
| | 18 | — | 1.2 | — | — | — | — | — |
| 40° C. | 0 | 0.2 | 0.2 | 0.2 | 0.2 | 0.2 | 0.2 | 0.2 |
| | 2 | 1.3 | 1.3 | 1.4 | 1.3 | 1.4 | 1.2 | 1.3 |
| | 4 | 2.2 | 2.2 | 2.4 | 2.1 | 2.3 | 2.1 | 2.2 |
| | 6 | 3.0 | 3.0 | 3.3 | 2.8 | 3.1 | 2.8 | 3.0 |

Results and Discussion

The LMW content increases only slightly over time but all tested formulations generally resulted in low levels of fragmentation.

3.2.5. Turbidity Measurements

The results of opalescence are summarized below. No changes in opalescence were observed over the time of storage at the different conditions. The formulations containing L-arginine HCl (F3 and F5) showed the highest opalescence. However, there was no increasing opalescence in the course of the study for F3 and F5. In none of the tested formulations visible particles were observed.

TABLE 16

| Storage condition | Storage time, months | F1 | F2 | F3 | F4 | F5 | F6 | F7 |
|---|---|---|---|---|---|---|---|---|
| | | Opalescence [FNU] of seven formulations stored at 5° C., 25° C. and 40° C.. | | | | | | |
| 5° C. | 0 | 1 | 5 | 11 | 7 | 15 | 6 | 4 |
| | 4 | 5 | 5 | 11 | 7 | 13 | 7 | 4 |
| | 6 | 6 | 6 | 12 | 7 | 14 | 8 | 4 |
| | 9 | 5 | 5 | 11 | 7 | 15 | 8 | 6 |
| | 12 | 6 | 6 | 12 | 7 | 12 | 8 | 3 |
| | 18 | — | 6 | — | — | — | — | — |
| 25° C. | 0 | 5 | 5 | 11 | 7 | 15 | 6 | 4 |
| | 2 | 6 | 5 | 12 | 7 | 13 | 7 | 4 |
| | 4 | 5 | 5 | 13 | 7 | 13 | 7 | 3 |
| | 6 | 7 | 6 | 12 | 8 | 14 | 8 | 4 |
| | 9 | 8 | 7 | 13 | 9 | 14 | 8 | 4 |
| | 12 | 6 | 6 | 12 | 8 | 14 | 8 | 4 |
| | 18 | — | 7 | — | — | — | — | — |

Results and Discussion

L-arginine HCL containing formulations showed increased opalescence.

3.3. Further Analytics and Results

In addition, further analytics were performed for the seven formulations tested with the following results (storage times and temperature were as described above).

The protein concentration remained essentially constant over the storage time of 18 months and at the different storage temperatures tested.

The pH value remained essentially constant over the storage time of 18 months and at the different storage temperatures tested.

The osmolality remained essentially constant over the storage time of 18 months and at the different storage temperatures tested. The tested values ranged from 298-326 mOsm/kg.

No visible particles were observed.

The IEC/WCX measurements of formulations at 5° C. for the tested storage times showed constant levels of main peak (69.7-72.2%), APG (18-20%) and BPG (8-13%). At 25° C. and 40° C. the main peak decreases and APG level increases for all formulations in a similar range. At 25° C. and 40° C. BPG level of formulations with pH 6.0 is lightly lower (up to 2%) than formulations with pH 5.7.

The particle content measured by MFI remained essentially constant over the storage time of 18 months and at the different storage temperatures tested. In particular, for particles $\geq 10$ μm and $\geq 25$ μm no relevant increasing particle count could be observed for all formulations over time of storage at 5° C. and 25°

C./60% r.h. For particles ≥2 μm, the particle count at 25° C. was increased. The increase was for all formulations in a similar range.

The specific binding activity remained essentially constant over the storage time of 18 months and at the different storage temperatures tested. The specific binding activity was in a range of 95-100%.

The break loose and gliding forces remained essentially constant over the storage time of 18 months and at 5° C. At 25° C. the maximum gliding force, average gliding force and break loose force increased over time of storage for all formulations. No differences between the formulations were observed. Maximum gliding forces ranged from 7.1-23.6 N, average gliding forces from 6.7-20.5 N and break loose force from 3.4-7.1 N.

The dynamic viscosity measured at 20° C. remained essentially constant over the storage time of 18 months and at the different storage temperatures tested. The dynamic viscosity was in a range of 8.3-10.7 mPas.

3.4. Summary of Results

The present example describes the storage stability of seven different 150 mg/ml risankizumab formulations. Trehalose and mannitol instead of sorbitol were used to adjust the tonicity. F2 was additionally analyzed after 18 months.

UP-SEC showed that a pH of 6.0 compared to pH 5.7 leads in the tested formulations to a slightly larger degradation of risankizumab in form of lower monomer content and higher HMW. L-arginine HCl containing formulations showed slightly lower degradation measured by UP-SEC but increased opalescence and slightly increased LMW contents. IEC showed no relevant differences between the formulations and were therefore not a decisive factor. The same applies to pH, protein concentration, osmolality, viscosity, break loose and gliding force, subvisible particles and visible particles. No differences between the formulations were seen by this data.

4. Comparison of Acetate and Succinate Buffer Systems with Different pH Values Over Long Term Storage The present example analyzes the storage stability of seven different 150 mg/ml risankizumab formulations in Neopak syringes to analyze the storage stability of the formulations and identify advantageous formulations. In comparison to the seven formulations of the prior example, the tonicity was slightly modified. Three conditions were again tested (as identified above). The formulations analyzed are summarized in Table 17.

TABLE 17

| Composition of the analyzed formulations. | |
| --- | --- |
| Formulation | Composition |
| F1 | 150 mg/mL risankizumab, 10 mM acetate + 95 mM trehalose + 95 mM mannitol + 0.2 mg/mL PS20, pH 5.7 |
| F2 | 150 mg/mL risankizumab, 10 mM acetate + 185 mM trehalose + 0.2 mg/mL PS20, pH 5.7 |
| F3 | 150 mg/mL risankizumab, 10 mM acetate + 110 mM trehalose + 50 mM L-arginine HCl + 0.2 mg/mL PS20, pH 5.7 |
| F4 | 150 mg/mL risankizumab, 4.4 mM succinate + 180 mM trehalose + 0.2 mg/mL PS20, pH 6.0 |
| F5 | 150 mg/mL risankizumab, 4.4 mM succinate + 110 mM trehalose + 50 mM L-arginine HCl + 0.2 mg/mL PS20, pH 6.0 |
| F6 | 150 mg/mL risankizumab, 4.4 mM succinate + 95 mM trehalose + 95 mM mannitol + 0.2 mg/mL PS20, pH 6.0 |
| F7 | 150 mg/mL risankizumab, 200 mM trehalose + 0.2 mg/mL PS20, pH 5.7 (buffer free) |

The formulations were prepared by mixing the starting material with a concentrated spike solution (comprising the auxiliary agents, i.e. the excipients and buffers).

4.1. Analytics

For analysis of the samples, inter alia UP-SEC was performed and the opalescence was measured. Further details on the utilized analysis methods are described below.

4.2. Results 4.2.1. Measurement of the HIMW Content

TABLE 18

| Measured HMW content in % of the UP-SEC analysis for long-term storage at 5° C., 25° C. and 40° C.. | | | | | | | |
| --- | --- | --- | --- | --- | --- | --- | --- |
| Storage condition | Storage time, months | F1 in % | F2 in % | F3 in % | F4 in % | F5 in % | F6 in % | F7 in% |
| 5° C. | 0 | 1.3 | 1.3 | 1.2 | 1.6 | 1.4 | 1.6 | 1.4 |
| | 4 | 1.5 | 1.6 | 1.4 | 1.9 | 1.5 | 1.9 | 1.6 |
| | 6 | 1.6 | 1.7 | 1.5 | 2.0 | 1.6 | 2.0 | 1.7 |
| | 9 | 1.8 | 1.8 | 1.6 | 2.3 | 1.8 | 2.3 | 1.9 |
| | 12 | 1.9 | 1.9 | 1.6 | 2.3 | 1.8 | 2.3 | 1.9 |
| | 18 | — | 2.0 | — | — | — | — | — |
| 25° C. | 0 | 0 | 1.3 | 1.3 | 1.2 | 1.6 | 1.4 | 1.6 |
| | 2 | 2.0 | 2.0 | 1.7 | 2.4 | 1.8 | 2.4 | 2.0 |
| | 4 | 2.2 | 2.2 | 1.8 | 2.5 | 1.9 | 2.5 | 2.2 |
| | 6 | 2.4 | 2.4 | 2.0 | 2.7 | 2.1 | 2.8 | 2.4 |
| | 9 | 2.7 | 2.7 | 2.2 | 3.0 | 2.3 | 3.0 | 2.7 |
| | 12 | 2.8 | 2.8 | 2.3 | 3.2 | 2.4 | 3.2 | 2.9 |
| | 18 | — | 3.2 | — | — | — | — | — |
| 40° C. | 0 | 0 | 1.3 | 1.3 | 1.2 | 1.6 | 1.4 | 1.6 |
| | 2 | 3.7 | 3.6 | 3.4 | 3.9 | 3.4 | 4.0 | 3.5 |
| | 4 | 5.2 | 5.1 | 5.1 | 5.3 | 4.8 | 5.4 | 4.9 |
| | 6 | 6.7 | 6.7 | 6.5 | 6.8 | 6.2 | 6.8 | 6.4 |

Results and Discussion

The HMW content remained overall low in all tested formulations indicating that the used formulations can stabilize risankizumab at high concentrations. The UP-SEC results further show that a pH of 6.0 compared to pH 5.7 leads to a larger degradation of risankizumab in form of lower monomer contents and higher HMW levels. Therefore, a pH of 5.7 is particularly advantageous for formulations according to the present disclosure. Nevertheless, also the formulations having a higher pH value of 6.0 such as F4, F5 and F6 showed overall good performance in view of the UP-SEC analysis results.

4.2.2. Measurement of the LMW Content

TABLE 19

Measured LMW content in % of the UP-SEC analysis
for long-term storage at 5° C., 25° C. and 40° C.

| Storage condition | Storage time, months | F1 in % | F2 in % | F3 in % | F4 in % | F5 in % | F6 in % | F7 in % |
|---|---|---|---|---|---|---|---|---|
| 5° C. | 0 | 0.5 | 0.5 | 0.5 | 0.5 | 0.5 | 0.6 | 0.6 |
| | 4 | 0.6 | 0.6 | 0.7 | 0.6 | 0.7 | 0.7 | 0.7 |
| | 6 | 0.7 | 0.7 | 0.7 | 0.7 | 0.7 | 0.7 | 0.7 |
| | 9 | 0.7 | 0.7 | 0.7 | 0.7 | 0.7 | 0.7 | 0.7 |
| | 12 | 0.6 | 0.6 | 0.6 | 0.6 | 0.6 | 0.6 | 0.6 |
| | 18 | — | 0.7 | — | — | — | — | — |
| 25° C. | 0 | 0.5 | 0.5 | 0.5 | 0.5 | 0.5 | 0.6 | 0.6 |
| | 2 | 0.9 | 0.9 | 1.0 | 0.9 | 0.9 | 0.9 | 0.9 |
| | 4 | 1.3 | 1.3 | 1.4 | 1.3 | 1.3 | 1.3 | 1.3 |
| | 6 | 1.8 | 1.7 | 1.8 | 1.7 | 1.7 | 1.7 | 1.7 |
| | 9 | 2.2 | 2.2 | 2.4 | 2.1 | 2.2 | 2.1 | 2.2 |
| | 12 | 2.4 | 2.4 | 2.6 | 2.3 | 2.5 | 2.4 | 2.4 |
| | 18 | — | 3.6 | — | — | — | — | — |
| 40° C. | 0 | 0.5 | 0.5 | 0.5 | 0.5 | 0.5 | 0.6 | 0.6 |
| | 2 | 3.7 | 3.7 | 4.3 | 3.5 | 4.1 | 3.5 | 3.7 |
| | 4 | 6.4 | 6.4 | 7.2 | 6.1 | 7.0 | 6.1 | 6.4 |
| | 6 | 8.9 | 8.9 | 9.9 | 8.4 | 9.5 | 8.5 | 8.9 |

Results and Discussion

The tested formulations were stable over the measurement time for all tested temperatures. Therefore, high protein concentrations of 150 mg/mL risankizumab were effectively stabilized using the tested formulations. At higher storage temperature, a slight increase of LMW content was observed for L-arginine HCl containing formulations. This is a surprising finding, as L-arginine containing formulations typically are known to further stabilize formulations. Hence, a formulation of 150 mg/mL risankizumab is different from other protein formulations in this respect. A formulation according to the present disclosure without arginine is therefore preferred.

4.2.3. Measurement of the Opalescence

TABLE 20

Measured opalescence in FNU for long-term
storage at 5° C., 25° C. and 40° C.

| Storage condition | Storage time, months | F1 in FNU | F2 in FNU | F3 in FNU | F4 in FNU | F5 in FNU | F6 in FNU | F7 in FNU |
|---|---|---|---|---|---|---|---|---|
| 5° C. | 0 | 1 | 5 | 11 | 7 | 15 | 6 | 4 |
| | 4 | 5 | 5 | 11 | 7 | 13 | 7 | 4 |
| | 6 | 6 | 6 | 12 | 7 | 14 | 8 | 4 |
| | 9 | 5 | 5 | 11 | 7 | 15 | 8 | 6 |
| | 12 | 6 | 6 | 12 | 7 | 12 | 8 | 3 |
| | 18 | — | 6 | — | — | — | — | — |
| 25° C. | 0 | 5 | 5 | 11 | 7 | 15 | 6 | 4 |
| | 2 | 6 | 5 | 12 | 7 | 13 | 7 | 4 |
| | 4 | 5 | 5 | 13 | 7 | 13 | 7 | 3 |
| | 6 | 7 | 6 | 12 | 8 | 14 | 8 | 4 |
| | 9 | 8 | 7 | 13 | 9 | 14 | 8 | 4 |
| | 12 | 6 | 6 | 12 | 8 | 14 | 8 | 4 |
| | 18 | — | 7 | — | — | — | — | — |

Results and Discussion

Overall, no or only a slight increase in opalescence was observed over time, indicating stability of all tested formulations. For formulations which contain L-arginine HCl (F3 and F5) a higher opalescence was observed.

4.3. Summary of Results

The measured parameters show that all formulations are suitable for preparing high risankizumab concentrations of 150 mg/mL in a stable manner. The long-term stability revealed some differences between the formulations:

UP-SEC showed that a pH of 6.0 compared to pH 5.7 leads to a larger degradation of risankizumab in form of lower monomer content and higher HMW.

L-arginine HCl containing formulations showed lower degradation measured by UP-SEC but increased opalescence and slight increase of LMW.

F2 was additionally analyzed after 18 months.

Noteworthy, also formulations F1 and F7 were stable. Buffer-free formulations and formulations comprising more than one type of tonicity agent were also stable and are thus suitable to provide a formulation comprising 150 mg/mL risankizumab.

In summary, formulation F2 was found to be particularly stable in respect to the measured LMW and HMW content, as well as opalescence, indicating a superior stability. This result was very surprising, as typically risankizumab is known to be used at higher pH values. Hence, the particularly high concentration of risankizumab shifts the optimal pH value to about 5.7, which was unexpected. Moreover, it was surprising that L-arginine HCl did not result in further stabilization but in fact reduced the stability of the formulations, supported by the higher opalescence and measured LMW content. Consequently, the particular properties of risankizumab at a high concentration, e.g. 150 mg/mL, necessitate different optimal conditions than formerly known formulations of risankizumab.

5. Comparison of Acetate and Succinate Buffer Systems with Different pH Values while Shaking The goal of the present example was to evaluate the influence of shaking stress on the product quality of different formulations at 150 mg/mL risankizumab. Different formulations were tested regarding their ability to stabilize risankizumab against shaking stress. Therefore, the formulation was exposed to different shaking stresses at the antibody concentration of 150 mg/mL.

In total eleven formulations that differ in pH, buffering and tonicity agent were filled into 6R vials and 1 mL Neopak syringes with 27 gauge ½ inch needles and were shaken for 21 days at room temperature. Corresponding buffer solutions without protein were shaken, stored and analyzed as well. Shaking conditions:

Shaking temperature: room temperature (approx. 25° C.)
Shaking time: 21 days
Type of shaking: Horizontal shaker (vial), rocking shaker (syringe); the shaking was conducted protected from light To exclude the influence of temperature as an additional stress on product quality further vials and syringes were stored at room temperature without shaking.

5.1. Preparation of Formulations 11 risankizumab test formulations were prepared (see table 21) and subjected to:

a) shaking of vials for 1, 5, 7, 14, 21 days in a horizontal shaker with 300 U/min (protected from light);

b) shaking of syringes for 1, 5, 7, 14, 21 days in a rocking shaker, movement adjusted to respective viscosity to ensure air bubble movement (protected from light); and c) room temperature (25° C.) for 1, 5, 7, 14, 21 days (protected from light).

TABLE 21

| | Formulations chosen for shaking study. |
|---|---|
| F1 | 10 mM acetate + 6.5 mM succinate + 185 mM sorbitol + 0.02 % PS20, pH 5.7 |
| F2 | 10 mM acetate + 200 mM sorbitol + 0.02 % PS20, pH 5.7 |
| F3 | 10 mM acetate + 50 mM L-arginine HCl + 110 mM sorbitol + 0.02 % PS20, pH 5.7 |
| F4 | 10 mM succinate + 185 mM sorbitol + 0.02 % PS20, pH 6.2 |
| F5 | 10 mM acetate + 95 mM mannitol + 95 mM trehalose + 0.02 % PS20, pH 5.7 |
| F6 | 10 mM acetate + 185 mM trehalose + 0.02 % PS20, pH 5.7 |
| F7 | 10 mM acetate + 50 mM L-arginine HCl + 110 mM trehalose + 0.02% PS20, pH 5.7 |
| F8 | 4.4 mM succinate + 185 mM trehalose + 0.02 % PS20, pH 6.0 |
| F9 | 4.4 mM succinate + 50 mM L-arginine HCl + 110 mM trehalose + 0.02% PS20, pH 6.0 |
| F10 | 4.4 mM succinate + 95 mM mannitol + 95 mM trehalose + 0.02 % PS20, pH 6.0 |
| F11 | Buffer-free, 200 mM trehalose, 0.02 % PS20, pH 5.7 |

As a packaging material the formulations were added to vials (Schott) or Neopak syringes. The sterile filtered protein solutions were filled under laminar flow into the sterilized primary packaging materials. The filling volume for the vials was defined to be 3.6 mL. The syringes were filled with 1.04 mL each. All vials and syringes were inspected for visual particles and results were recorded.

5.2. Analytics

The analytics at each analytical time point were performed directly after sampling except for the chromatographic assays like SEC for which samples were stored at $-70°$ C. until measurement. Following devices were used for analysis:

UV-Vis spectrophotometer Solo VPE: Conc. at 280 nm, baseline correction at 320 nm, extinction coefficient: 1.52; C Technologies, Inc., NJ, USA Opalescence meter: HACH Lange opalescence meter; filter: 400-600 nm; Hach Lange GmbH, Düsseldorf, Germany Ultra performance size exclusion chromatography (UP-SEC): UPLC26, H-Class UV-detection at 280 nm Waters, Milford, MA Charge heterogeneity by weak cation exchange chromatography (WCX): HPLC75; Fluorescence detection Extinction: 278 nm, Emission: 350 nm; Waters, Milford, MA IL-23 binding activity: Biacore T200 Chip: CM5 GE Healthcare, Chalfont St Giles, UK pH-meter: SevenGo-Mettler Toledo, Columbus, OH Particel sizer: Micro Flow Imaging™ Flow Microscope; By micro flow imaging (MFI); Brightwell Technologies Inc, Ottawa, ON, Canada Osmometer: Osmomat 030 By freezing point depression, Gonotec GmbH, Berlin, Germany Further details on the utilized analysis methods are described below.

5.3. Results 5.3.1. Measurement of the Monomer Content

Monomer content is a key quality attribute of protein stability and quality during stress-induced storage. HP-SEC and UP-SEC were used to measure the monomer content of the formulations.

UP-SEC Analysis

TABLE 22

| UP-SEC-Monomer in % of syringe and vial: Initial values and values after 1 / 5 / 7 / 14 / 21 days of shaking and after 21 days without movement at 25° C. | | | | | | | | | | | | |
|---|---|---|---|---|---|---|---|---|---|---|---|---|
| Time | Packing | F1 (%) | F2 (%) | F3 (%) | F4 (%) | F5 (%) | F6 (%) | F7 (%) | F8 (%) | F9 (%) | F10 (%) | F11 (%) |
| Initial | Syringe | 97.9 | 97.9 | 97.9 | 97.5 | 97.8 | 97.8 | 97.9 | 97.4 | 97.5 | 97.5 | 97.7 |
| 1 day | | 97.6 | 97.6 | 97.7 | 97.0 | 97.6 | 97.6 | 97.7 | 97.3 | 97.5 | 97.3 | 97.6 |
| 5 days | | 97.5 | 97.5 | 97.6 | 96.9 | 97.5 | 97.5 | 97.6 | 97.2 | 97.4 | 97.2 | 97.5 |
| 7 days | | 97.4 | 97.4 | 97.5 | 96.7 | 97.4 | 97.3 | 97.5 | 97.0 | 97.3 | 96.9 | 97.3 |
| 14 days | | 97.3 | 97.2 | 97.4 | 96.6 | 97.2 | 97.2 | 97.4 | 96.9 | 97.2 | 96.8 | 97.2 |
| 21 days | | 97.3 | 97.3 | 97.4 | 96.7 | 97.2 | 97.3 | 97.4 | 96.9 | 97.2 | 96.9 | 97.3 |
| 21 days* | | 97.3 | 97.3 | 97.5 | 96.8 | 97.3 | 97.3 | 97.5 | 97.1 | 97.4 | 97.0 | 97.4 |
| Initial | Vial | 97.9 | 97.8 | 97.9 | 97.5 | 97.8 | 97.7 | 97.9 | 97.6 | 97.8 | 97.7 | 97.9 |
| 1 day | | 97.7 | 97.7 | 97.8 | 97.3 | 97.7 | 97.7 | 97.8 | 97.5 | 97.7 | 97.5 | 97.7 |
| 5 days | | 97.5 | 97.5 | 97.6 | 97.0 | 97.5 | 97.5 | 97.6 | 97.3 | 97.5 | 97.3 | 97.6 |
| 7 days | | 97.5 | 97.5 | 97.6 | 97.0 | 97.5 | 97.5 | 97.6 | 97.2 | 97.5 | 97.3 | 97.4 |
| 14 days | | 97.3 | 97.3 | 97.4 | 96.7 | 97.2 | 97.2 | 97.4 | 97.0 | 97.3 | 97.0 | 97.3 |
| 21 days | | 97.2 | 97.2 | 97.4 | 96.7 | 97.2 | 97.2 | 97.4 | 96.9 | 97.2 | 97.0 | 97.3 |
| 21 days* | | 97.3 | 97.3 | 97.4 | 96.7 | 97.2 | 97.2 | 97.4 | 97.0 | 97.3 | 97.0 | 97.3 |

*corresponds to no movement, whereas the other samples were shaken for the indicated amount of time.

HP-SEC Analysis

The trends of the HP-SEC analysis are analogous to those of the UP-SEC and thus confirm these results. Monomer values ranging from 97.4-98.8% were obtained.

Results and Discussion

Overall, the measurements in syringes and vials show similar trends and all formulations proved to be stable with only slight reductions in monomer content.

5.3.2. Measurement of the HMW Content

HP-SEC and UP-SEC were used to measure the monomer content of the formulations. HP-SEC was used to determine levels of aggregate (HMW) formation during shaking of the syringes and vials.

UP-SEC Analysis

The results of the UP-SEC analysis are shown below. The data show similar results as the HP-SEC analysis that the formation of aggregates is mainly driven by the pH. When comparing the initial values it is obvious that formulations at pH 6.0 or 6.2 show a slightly increased HMW content from 0.2 to 0.5% in comparison to solutions formulated at pH 5.7. This trend could also be seen after 21 days of shaking with HMW contents of approx. 1.6% in formulations ≥pH 6.0 and 1.3% in formulations at pH 5.7.

Formulations containing L-arginine like F3 and F7 showed the lowest level of aggregation after 21 days of shaking. The differences in monomer content for the eleven formulations tested in this study observed in UP-SEC and HP-SEC are not significant. The loss of monomer content was in an acceptable range for all formulations being tested. Generally, it can be summarized that the shaking does not significantly increase the HMW content in comparison to the results after 21 days without movement.

The data obtained using the UP-SEC is summarized in Table 23.

TABLE 23

| UP-SEC HMW content in % of syringe and vial: Initial values and values after 1 / 5 / 7 / 14 / 21 days of shaking and after 21 days without movement at 25° C. | | | | | | | | | | | | |
|---|---|---|---|---|---|---|---|---|---|---|---|---|
| Time | Packing | F1 (%) | F2 (%) | F3 (%) | F4 (%) | F5 (%) | F6 (%) | F7 (%) | F8 (%) | F9 (%) | F10 (%) | F11 (%) |
| Initial | Syringe | 0.9 | 0.9 | 0.8 | 1.3 | 0.9 | 0.9 | 0.8 | 1.1 | 1.0 | 1.0 | 0.9 |
| 1 day | | 1.0 | 1.0 | 1.0 | 1.6 | 1.0 | 1.0 | 0.9 | 1.3 | 1.1 | 1.3 | 1.0 |
| 5 days | | 1.1 | 1.1 | 1.1 | 1.8 | 1.2 | 1.2 | 1.0 | 1.4 | 1.2 | 1.4 | 1.1 |
| 7 days | | 1.2 | 1.3 | 1.1 | 2.0 | 1.3 | 1.3 | 1.2 | 1.7 | 1.4 | 1.7 | 1.3 |
| 14 days | | 1.3 | 1.4 | 1.2 | 2.0 | 1.4 | 1.4 | 1.2 | 1.7 | 1.4 | 1.8 | 1.4 |
| 21 days | | 1.4 | 1.4 | 1.3 | 2.0 | 1.5 | 1.5 | 1.2 | 1.7 | 1.5 | 1.8 | 1.4 |
| 21 days* | | 1.4 | 1.3 | 1.2 | 1.9 | 1.4 | 1.4 | 1.2 | 1.6 | 1.3 | 1.6 | 1.3 |
| Initial | Vial | 0.9 | 0.9 | 0.8 | 1.3 | 0.9 | 0.9 | 0.8 | 1.1 | 0.9 | 1.1 | 0.9 |
| 1 day | | 1.0 | 1.0 | 0.9 | 1.4 | 1.0 | 1.0 | 0.9 | 1.2 | 1.0 | 1.2 | 1.0 |
| 5 days | | 1.1 | 1.1 | 1.0 | 1.6 | 1.1 | 1.1 | 1.0 | 1.4 | 1.2 | 1.3 | 1.1 |
| 7 days | | 1.2 | 1.2 | 1.1 | 1.7 | 1.2 | 1.2 | 1.0 | 1.4 | 1.1 | 1.4 | 1.2 |

TABLE 23-continued

UP-SEC HMW content in % of syringe and vial: Initial values and values after 1 / 5 / 7 / 14 / 21
days of shaking and after 21 days without movement at 25° C.

| Time | Packing | F1 (%) | F2 (%) | F3 (%) | F4 (%) | F5 (%) | F6 (%) | F7 (%) | F8 (%) | F9 (%) | F10 (%) | F11 (%) |
|---|---|---|---|---|---|---|---|---|---|---|---|---|
| 14 days | | 1.4 | 1.4 | 1.2 | 1.9 | 1.4 | 1.4 | 1.2 | 1.7 | 1.3 | 1.7 | 1.3 |
| 21 days | | 1.4 | 1.4 | 1.3 | 1.9 | 1.4 | 1.4 | 1.2 | 1.7 | 1.4 | 1.7 | 1.4 |
| 21 days* | | 1.4 | 1.4 | 1.3 | 2.0 | 1.5 | 1.5 | 1.2 | 1.7 | 1.4 | 1.7 | 1.4 |

*corresponds to no movement whereas the other samples were shaken for the indicated amount of time.

HP-SEC Analysis

The trend of the data of the HP-SEC analysis are analogous to those of the UP-SEC and thus confirm these results.

Results and Discussion

Overall, all tested formulations proved to be stable. Similar results were obtained for vials and syringes.

5.3.3. Measurement of the Opalescence and Further Parameters

Opalescence, osmolality, pH-values and protein concentrations of all tested formulations remained essentially unchanged following 21 days of shaking for syringes on a horizontal shaker as well as for vials on a rocking shaker (see subsequent data). The lowest level of opalescence was observed in the buffer-free formulation F11 without any additional buffer like acetate or succinate. No observations could be made with regard to visual inspection. No significant difference can be observed by comparing the generated data of vials and syringes.

The increased opalescence level of F6 after 1 day and F10 after 5 days could not be confirmed by the results of the following sampling time points. Therefore, it is likely that a measuring error occurred and these results do not have relevance for the interpretation of the results.

TABLE 24

Shaking of formulations in syringe and vial: Initial values, values after 1 / 5 / 7 / 14 / 21
days of shaking and values after 21 days without (w/o) movement of opalescence,
osmolality, pH-values and protein conc. (shaking at room temperature).

| Formulation | Time | Opalescence (FNU) Syringe | Vial | Osmolality (mOsm/kg) Syringe | Vial | pH Syringe | Vial | Protein (mg/mL) Syringe | Vial |
|---|---|---|---|---|---|---|---|---|---|
| F1 | Initial | 9.0 | 8.1 | 307 | 306 | 5.6 | 5.7 | 150 | 152 |
| | 1 day | 8.1 | 8.3 | 304 | 305 | 5.7 | 5.7 | 151 | 151 |
| | 5 days | 7.6 | 9.2 | 307 | 305 | 5.7 | 5.8 | 151 | 151 |
| | 7 days | 8.5 | 9.0 | 307 | 306 | 5.7 | 5.7 | 148 | 150 |
| | 14 days | 8.6 | 8.3 | 305 | 307 | 5.7 | 5.7 | 152 | 151 |
| | 21 days | 8.8 | 8.6 | 304 | 306 | 5.8 | 5.7 | 150 | 149 |
| | 21 days* | 9.6 | 8.0 | 308 | 304 | 5.7 | 5.7 | 151 | 149 |
| F2 | Initial | 5.6 | 5.4 | 306 | 307 | 5.6 | 5.6 | 151 | 152 |
| | 1 day | 5.9 | 5.7 | 304 | 305 | 5.7 | 5.7 | 149 | 152 |
| | 5 days | 5.2 | 5.6 | 305 | 305 | 5.7 | 5.7 | 149 | 149 |
| | 7 days | 5.7 | 5.8 | 304 | 305 | 5.7 | 5.7 | 149 | 149 |
| | 14 days | 5.4 | 5.4 | 306 | 307 | 5.7 | 5.7 | 151 | 151 |
| | 21 days | 6.5 | 7.0 | 304 | 304 | 5.7 | 5.7 | 151 | 150 |
| | 21 days* | 5.7 | 4.8 | 309 | 305 | 5.7 | 5.7 | 150 | 151 |
| F3 | Initial | 12.8 | 11.3 | 298 | 289 | 5.6 | 5.7 | 154 | 152 |
| | 1 day | 13.0 | 12.2 | 289 | 282 | 5.7 | 5.8 | 151 | 149 |
| | 5 days | 12.7 | 12.7 | 291 | 286 | 5.6 | 5.7 | 153 | 151 |
| | 7 days | 12.2 | 13.3 | 292 | 291 | 5.7 | 5.7 | 153 | 149 |
| | 14 days | 12.2 | 11.9 | 293 | 291 | 5.7 | 5.7 | 152 | 151 |
| | 21 days | 12.7 | 12.2 | 291 | 290 | 5.7 | 5.7 | 153 | 151 |
| | 21 days* | 13.0 | 11.3 | 293 | 292 | 5.7 | 5.7 | 152 | 154 |
| F4 | Initial | 13.4 | 11.1 | 301 | 294 | 6.1 | 6.2 | 151 | 150 |
| | 1 day | 11.4 | 11.4 | 296 | 297 | 6.0 | 6.3 | 151 | 152 |
| | 5 days | 11.9 | 12.4 | 297 | 296 | 6.0 | 6.2 | 150 | 148 |
| | 7 days | 11.7 | 12.8 | 299 | 295 | 6.2 | 6.2 | 153 | 149 |
| | 14 days | 11.9 | 11.2 | 298 | 296 | 6.2 | 6.2 | 152 | 153 |
| | 21 days | 12.2 | 12.3 | 301 | 298 | 6.2 | 6.2 | 151 | 151 |
| | 21 days* | 12.9 | 11.5 | 297 | 299 | 6.2 | 6.2 | 153 | 152 |
| F5 | Initial | 5.9 | 4.9 | 310 | 306 | 5.6 | 5.7 | 156 | 154 |
| | 1 day | 5.6 | 5.3 | 306 | 303 | 5.7 | 5.7 | 154 | 153 |
| | 5 days | 5.7 | 5.8 | 305 | 305 | 5.6 | 5.7 | 154 | 154 |
| | 7 days | 5.5 | 6.0 | 309 | 304 | 5.7 | 5.7 | 153 | 151 |
| | 14 days | 4.9 | 5.0 | 306 | 305 | 5.7 | 5.7 | 156 | 157 |
| | 21 days | 5.4 | 7.5 | 306 | 308 | 5.7 | 5.7 | 155 | 154 |
| | 21 days* | 6.3 | 4.7 | 307 | 305 | 5.6 | 5.7 | 154 | 153 |
| F6 | Initial | 5.7 | 4.9 | 313 | 311 | 5.7 | 5.7 | 153 | 151 |
| | 1 day | 11.0 | 6.1 | 304 | 307 | 5.6 | 5.8 | 152 | 151 |
| | 5 days | 6.0 | 6.1 | 308 | 305 | 5.6 | 5.7 | 150 | 149 |
| | 7 days | 5.6 | 5.9 | 307 | 308 | 5.7 | 5.7 | 151 | 151 |
| | 14 days | 5.2 | 4.9 | 307 | 309 | 5.7 | 5.7 | 150 | 151 |

TABLE 24-continued

Shaking of formulations in syringe and vial: Initial values, values after 1 / 5 / 7 / 14 / 21
days of shaking and values after 21 days without (w/o) movement of opalescence,
osmolality, pH-values and protein conc. (shaking at room temperature).

| Formulation | Time | Opalescence (FNU) | | Osmolality (mOsm/kg) | | pH | | Protein (mg/mL) | |
|---|---|---|---|---|---|---|---|---|---|
| | | Syringe | Vial | Syringe | Vial | Syringe | Vial | Syringe | Vial |
| | 21 days | 5.7 | 6.5 | 311 | 310 | 5.7 | 5.7 | 152 | 152 |
| | 21 days* | 5.5 | 4.8 | 311 | 310 | 5.7 | 5.7 | 153 | 150 |
| F7 | Initial | 12.3 | 10.8 | 307 | 304 | 5.6 | 5.7 | 153 | 153 |
| | 1 day | 12.3 | 11.3 | 302 | 302 | 5.6 | 5.7 | 153 | 154 |
| | 5 days | 12.1 | 12.5 | 301 | 302 | 5.6 | 5.7 | 151 | 153 |
| | 7 days | 11.4 | 12.6 | 302 | 302 | 5.7 | 5.7 | 153 | 154 |
| | 14 days | 12.2 | 10.9 | 304 | 303 | 5.7 | 5.7 | 153 | 152 |
| | 21 days | 11.5 | 12.1 | 306 | 304 | 5.7 | 5.7 | 153 | 152 |
| | 21 days* | 12.6 | 10.6 | 305 | 303 | 5.6 | 5.7 | 153 | 153 |
| F8 | Initial | 7.0 | 6.1 | 295 | 290 | 5.9 | 6.0 | 151 | 151 |
| | 1 day | 6.7 | 7.3 | 290 | 287 | 5.9 | 6.0 | 151 | 150 |
| | 5 days | 6.9 | 7.6 | 289 | 286 | 5.9 | 6.0 | 150 | 150 |
| | 7 days | 6.5 | 7.1 | 293 | 297 | 6.0 | 6.0 | 150 | 151 |
| | 14 days | 6.5 | 6.6 | 294 | 289 | 6.0 | 6.0 | 151 | 149 |
| | 21 days | 7.0 | 6.5 | 293 | 292 | 6.0 | 6.0 | 150 | 150 |
| | 21 days* | 7.5 | 6.3 | 291 | 288 | 6.0 | 6.0 | 151 | 147 |
| F9 | Initial | 13.9 | 12.4 | 298 | 291 | 5.9 | 6.0 | 149 | 149 |
| | 1 day | 12.5 | 12.7 | 292 | 293 | 5.9 | 6.0 | 151 | 148 |
| | 5 days | 13.6 | 13.5 | 291 | 292 | 5.9 | 6.0 | 150 | 148 |
| | 7 days | 12.8 | 13.7 | 295 | 296 | 6.0 | 6.0 | 150 | 153 |
| | 14 days | 12.7 | 12.3 | 295 | 294 | 6.0 | 6.0 | 149 | 150 |
| | 21 days | 13.1 | 12.9 | 295 | 296 | 6.0 | 6.0 | 150 | 150 |
| | 21 days* | 13.8 | 12.4 | 294 | 297 | 6.0 | 6.0 | 152 | 149 |
| F10 | Initial | 7.1 | 6.3 | 301 | 295 | 6.0 | 6.0 | 148 | 149 |
| | 1 day | 6.7 | 6.5 | 295 | 293 | 5.9 | 6.0 | 149 | 148 |
| | 5 days | 11.1 | 8.3 | 292 | 291 | 5.9 | 6.0 | 146 | 147 |
| | 7 days | 6.5 | 7.5 | 296 | 296 | 6.0 | 6.0 | 149 | 148 |
| | 14 days | 6.1 | 6.1 | 297 | 298 | 6.0 | 6.0 | 151 | 148 |
| | 21 days | 6.6 | 6.5 | 295 | 295 | 6.0 | 6.0 | 149 | 149 |
| | 21 days* | 7.4 | 5.9 | 295 | 295 | 6.0 | 6.0 | 150 | 148 |
| F11 | Initial | 4.9 | 3.3 | 306 | 298 | 5.6 | 5.6 | 148 | 146 |
| | 1 day | 3.8 | 4.0 | 299 | 300 | 5.6 | 5.7 | 147 | 144 |
| | 5 days | 4.9 | 4.2 | 300 | 297 | 5.6 | 5.7 | 145 | 147 |
| | 7 days | 3.7 | 4.2 | 300 | 300 | 5.7 | 5.7 | 147 | 146 |
| | 14 days | 3.7 | 3.2 | 301 | 301 | 5.7 | 5.7 | 147 | 148 |
| | 21 days | 3.7 | 3.3 | 303 | 301 | 5.6 | 5.7 | 148 | 146 |
| | 21 days* | 5.2 | 3.2 | 302 | 298 | 5.6 | 5.7 | 146 | 147 |

*corresponds to no movement, whereas the other samples were shaken for the indicated amount of time.

Binding Activity

The results of the SPR (Biacore) measurements showed that the shaking does not influence the binding activity of the molecule for the syringes on a rocking shaker as well as for the vials on a horizontal shaker. Overall, the binding activity remained high in a range of 91-111% and the specific binding activity in a range of 98-107%.

Results and Discussion

The opalescence depends on the formulation composition and ranges from 5 FNU in an excipient-free or buffer-free respectively to 14 FNU, but did not significantly increase over time.

The pH value, osmolality, opalescence and protein concentrations as well as binding activity against IL-23 remained unchanged for all formulations over the entire study period.

5.4. Further Analytics and Results

In addition, further analytics were performed for the eleven formulations tested with the following results. Shaking type and times, storage and used syringes and vials were as described above.

The HP-SEC fragments contents remained essentially constant over the shaking time in vials and syringes. The fragments content was in a range of 0.3-0.5%. The UP-SEC LMW contents remained essentially constant over the shaking time in vials and syringes. The fragments content was in a range of 1.3-1.4%.

The weak cation exchange chromatography (WCX) showed that the percentage of the distribution of the main peak, APG and BPG remained at a constant level for all formulations tested during the study. The levels of the main peak, APG and BPG did not change significantly over shaking time. No differences between the formulations were observed.

The particle content measured by Micro Flow Imaging (MFI) remained essentially constant over the 21 days shaking time.

5.5. Summary

All in all, only minor differences in stability-indicating parameters were detected between formulations following exposure to shaking stress. For example, the formulations F3 and F7 showed highest monomer content (HP-SEC & UP-SEC) but they also showed the highest level of opalescence. It can be summarized that the formulations being tested in this study would be a viable formulation.

6. Comparison of Acetate and Succinate Buffer Systems with Different pH Values in Multiple Freeze/Thaw Cycles The freeze and thaw behavior of different formulations at 150 mg/mL risankizumab and its influence on product quality was evaluated. Therefore, the formulations were exposed to freezing and thawing stresses in mini bags at the intended target concentration of 150 mg/mL and a fill volume of 12 mL to simulate the conditions of bag-freezing in pilot or large scale. An overview of the experimental schedule is provided in FIG. 3.

In total eleven formulations that differ in pH, buffering strategy and tonicity agent plus an intermediate storage bulk were filled into mini-bags with a filling volume of 12 mL followed by a controlled freezing step to −40° C. Additionally bags were stored at 5° C. Note, the eleven formulations correspond to the ones tested in the previous example.

The freezing step was performed using a freeze-thaw setup provided by a classical freeze-dryer. Here, the mini-bags with a sample volume of 12 mL were frozen controlled with a freezing ramp of 0.5° C./min to −40° C. At this point the temperature remained constant over sixteen hours to ensure complete freezing of the sample volume. The thawing step was performed according to the freezing step with a heating rate of 0.5° C./min. The hold time at room temperature was set to four hours.

A complete freeze/thaw cycle (1×F/T) is defined as follows:

1. Freezing from room temperature to −40° (0.5° C./min)
2. Hold time of 16 hours at −40° C.
3. Thawing from −40° C. to room temperature (0.5° C./min)
4. Hold time of 4 hours at room temperature This procedure was conducted for 1× F/T, 3× F/T and 6× F/T. After completion of the final process cycle the bags were transferred into a freezer at −40° C. and stored until the samples were thawed and analyzed simultaneously.

6.1. Preparation of Formulations

The formulations were prepared as described in the prior example (see Table 21). A further formulation F12 was prepared which is excipient-free containing 0.02% PS20, pH 5.7. 12 mL sterile filtered protein solutions were filled under laminar flow into the sterilized primary packaging materials, which are Mini Flexboy bags having a volume of 15 mL. All bags were inspected for visual particles and results were recorded.

In each freeze-thaw run twelve bags were put on each plate within the freeze-dryer. In total 36 bags were freeze/thawed each run including three bags per formulation. The bags were distributed in a defined scheme to eliminate influences of the bag position within the freeze-dryer.

6.2. Analytics

After conducting all cycles according to the experimental plan above, the bags were thawed in an additional thawing step successively. This procedure had the advantage that the samples could be analyzed altogether. The bags were transferred into the precooled freeze-dryer at −40° C. followed by the thawing step. HP-SEC, UP-SEC, osmolality, pH, protein concentration, opalescence, binding activity and sub-visible particle measurements were performed. Following devices were used for analysis:

UV-Vis spectrophotometer Solo VPE: Conc. at 280 nm, baseline correction at 320 nm, extinction coefficient: 1.52; C Technologies, Inc., NJ, USA Opalescence: HACH Lange opalescence meter; filter: 400-600 nm; Hach Lange GmbH, Düsseldorf, Germany Ultra performance size exclusion chromatography (UP-SEC): UPLC26, H-Class UV-detection at 280 nm Waters, Milford, MA Charge heterogeneity by weak cation exchange chromatography (WCX): HPLC75; Fluorescence detection Extinction: 278 nm, Emission: 350 nm; Waters, Milford, MA IL-23 binding activity: Biacore T200 Chip: CM5 GE Healthcare, Chalfont St Giles, UK pH-meter: SevenGo-Mettler Toledo, Columbus, OH Particel sizer: Micro Flow Imaging™ Flow Microscope; By micro flow imaging (MFI); Brightwell Technologies Inc, Ottawa, ON, Canada Osmometer: Osmomat 030 By freezing point depression, Gonotec GmbH, Berlin, Germany Further details on the utilized analysis methods are described below.

6.3. Results 6.3.1. Measurement of the Menemer and HMW Content

Monomer content is a key quality attribute of protein stability and quality during stress-induced storage. HP-SBC and UP-SEC was used to determine levels of aggregate formation during freczo/thaw of the mini-bags. The subsequent table summarizes the results of the HP-SBC & UP-SEC analytic.

TABLE 25

| | | HP-SEC / UP-SEC: Initial values and values after 1 / 3 / 6 F/T cycles and three weeks at 5° C. in %. | | | | | |
|---|---|---|---|---|---|---|---|
| Formulation | Sampling time point | Aggregate HP-SEC % | Monomer HP-SEC % | Fragment HP-SEC % | Aggregate UP-SEC % | Monomer UP-SEC % | Fragment UP-SEC % |
| F1 | intial | 1.4 | 98.3 | 0.4 | 1.3 | 97.2 | 1.5 |
| | 1 × F/T | 1.5 | 98.1 | 0.4 | 1.4 | 97.3 | 1.3 |
| | 3 × F/T | 1.5 | 98.2 | 0 4 | 1.4 | 97.4 | 1.2 |
| | 6 × F/T | 1.5 | 98.1 | 0.4 | 1.4 | 97.4 | 1.3 |
| | 5° C. | 1.6 | 98.1 | 0.4 | 1.4 | 97.3 | 1.3 |
| F2 | inital | 1.4 | 98.3 | 0.3 | 1.3 | 97.2 | 1.5 |
| | 1 × F/T | 1.5 | 98.1 | 0.4 | 1.5 | 97.2 | 1.5 |
| | 3 × F/T | 1.4 | 98.2 | 0.4 | 1.5 | 97.2 | 1.3 |
| | 6 × F/T | 1.5 | 98.2 | 0.4 | 1.4 | 97.3 | 1.3 |
| | 5° C. | 1.5 | 98.1 | 0.4 | 1.4 | 97.3 | 1.3 |
| F3 | inital | 1.2 | 98.4 | 0.3 | 1.2 | 97.3 | 1.5 |
| | 1 × F/T | 1.3 | 98.3 | 0.4 | 1.3 | 97.4 | 1.3 |
| | 3 × F/T | 1.3 | 98.4 | 0.4 | 1.3 | 97.5 | 1.3 |
| | 6 × F/T | 1.4 | 98.3 | 0.4 | 1.3 | 97.5 | 1.3 |
| | 5° C. | 1.4 | 98.3 | 0.4 | 1.3 | 97.5 | 1.3 |
| F4 | inital | 1.6 | 99.0 | 0.3 | 1.8 | 96.8 | 1.5 |
| | 1 × F/T | 2.1 | 97.6 | 0.4 | 2.0 | 96.8 | 1.2 |
| | 3 × F/T | 1.9 | 97.7 | 0.4 | 1.9 | 96.8 | 1.3 |

TABLE 25-continued

HP-SEC / UP-SEC: Initial values and values after 1 / 3 / 6 F/T cycles and three weeks at 5° C. in %.

| Formulation | Sampling time point | Aggregate HP-SEC % | Monomer HP-SEC % | Fragment HP-SEC % | Aggregate UP-SEC % | Monomer UP-SEC % | Fragment UP-SEC % |
|---|---|---|---|---|---|---|---|
| | 6 × F/T | 2.1 | 97.5 | 0.4 | 1.9 | 96.8 | 1.3 |
| | 5° C. | 2.0 | 97.6 | 0.4 | 1.9 | 96.9 | 1.3 |
| F5 | inital | 1.6 | 98.0 | 0.3 | 1.3 | 97.2 | 1.5 |
| | 1 × F/T | 1.5 | 98.1 | 0.4 | 1.4 | 97.3 | 1.3 |
| | 3 × F/T | 1.4 | 98.2 | 0.4 | 1.4 | 97.3 | 1.3 |
| | 6 × F/T | 1.5 | 98.2 | 0.4 | 1.4 | 97.3 | 1.3 |
| | 5° C. | 1.5 | 98.2 | 0.4 | 1.4 | 97.3 | 1.3 |
| F6 | inital | 1.3 | 98.3 | 0.3 | 1.3 | 97.2 | 1.5 |
| | 1 × F/T | 1.5 | 98.1 | 0.4 | 1.4 | 97.3 | 1.3 |
| | 3 × F/T | 1.4 | 98.2 | 0.4 | 1.4 | 97.3 | 1.3 |
| | 6 × F/T | 1.5 | 98.2 | 0.4 | 1.4 | 97.3 | 1.3 |
| | 5° C. | 1.5 | 98.1 | 0.4 | 1.4 | 97.3 | 1.3 |
| F7 | inital | 1.3 | 98.4 | 0.3 | 1.2 | 97.3 | 1.5 |
| | 1 × F/T | 1.4 | 98.3 | 0.4 | 1.3 | 97.4 | 1.3 |
| | 3 × F/T | 1.3 | 98.3 | 0.4 | 1.3 | 97.5 | 1.3 |
| | 6 × F/T | 1.4 | 98.3 | 0.4 | 1.2 | 97.5 | 1.3 |
| | 5° C. | 1.4 | 98.3 | 0.4 | 1.3 | 97.5 | 1.3 |
| F8 | inital | 1.5 | 98.2 | 0.3 | 1.5 | 97.0 | 1.4 |
| | 1 × F/T | 1.8 | 97.8 | 0.4 | 1.7 | 97.0 | 1.3 |
| | 3 × F/T | 1.7 | 97.9 | 0.4 | 1.6 | 97.1 | 1.3 |
| | 6 × F/T | 1.7 | 97.9 | 0.4 | 1.6 | 97.1 | 1.3 |
| | 5° C. | 1.7 | 97.9 | 0.4 | 1.6 | 97.1 | 1.3 |
| F9 | inital | 1.5 | 98.2 | 0.3 | 1.3 | 97.2 | 1.5 |
| | 1 × F/T | 1.5 | 98.1 | 0.4 | 1.4 | 97.3 | 1.3 |
| | 3 × F/T | 1.4 | 98.2 | 0.4 | 1.4 | 97.3 | 1.3 |
| | 6 × F/T | 1.5 | 98.1 | 0.4 | 1.4 | 97.3 | 1.3 |
| | 5° C. | 1.5 | 98.1 | 0.4 | 1.4 | 97.3 | 1.3 |
| F10 | inital | 1.6 | 98.1 | 0.3 | 1.5 | 97.0 | 1.5 |
| | 1 × F/T | 1.7 | 97.9 | 0.4 | 1.6 | 97.1 | 1.3 |
| | 3 × F/T | 1.7 | 98.0 | 0.4 | 1.6 | 97.1 | 1.3 |
| | 6 × F/T | 1.7 | 98.0 | 0.4 | 1.6 | 97.1 | 1.3 |
| | 5° C. | 1.7 | 97.9 | 0.4 | 1.5 | 97.3 | 1.3 |
| F11 | inital | 1.4 | 98.3 | 0.3 | 1.3 | 97.3 | 1.5 |
| | 1 × F/T | 1.4 | 98.2 | 0.4 | 1.4 | 97.3 | 1.3 |
| | 3 × F/T | 1.4 | 98.2 | 0.4 | 1.4 | 97.3 | 1.3 |
| | 6 × F/T | 1.4 | 98.2 | 0.4 | 1.4 | 97.3 | 1.3 |
| | 5° C. | 1.4 | 98.2 | 0.4 | 1.4 | 97.3 | 1.3 |
| F12 | inital | 1.5 | 98.2 | 0.3 | 1.3 | 97.2 | 1.5 |
| | 1 × F/T | 1.7 | 98.0 | 0.4 | 1.6 | 97.1 | 1.3 |
| | 3 × F/T | 1.8 | 97.8 | 0.4 | 1.7 | 97.0 | 1.3 |
| | 6 × F/T | 2.0 | 97.6 | 0.4 | 1.9 | 96.8 | 1.3 |
| | 5° C. | 1.5 | 98.1 | 0.4 | 1.3 | 97.4 | 1.3 |

The data show that the formation of aggregates is mainly driven by the pH. By comparing the results after six F/T cycles it is obvious that formulations at pH 6.0 or 6.2 show a slightly increased HMW content of 0.2-0.6% in comparison to solutions formulated at pH 5.7. Formulations containing L-arginine like F3 and F7 showed the lowest level of aggregation after six F/T cycles. Generally, it can be summarized that the freeze/thaw stress does not significantly increase the HMW content in comparison to the results after 21 days at 5° C.

6.3.2. Measurement of the Opalescence and Further Parameters

Opalescence, osmolality, pH-values and protein concentrations of all tested formulations remained unchanged following 6 P/T cycles and after storage at 5° C. for three weeks. The lowest level of opelescence was observed in buffer-free formulations (F11 & F12).

TABLE 26

Initial values and values after 1 / 3 / 6 F/T cycles of opalescence in FNU, osmolality in mOsm/kg, pH-values and protein conc. in g/L.

| Formulation | Components | Sampling time point | Opalescence FNU | Osmolatity mOsmol · kg⁻¹ | pH | Protein conc. g · L⁻¹ |
|---|---|---|---|---|---|---|
| F1 | 10 mM acetate + | initial | 7.7 | 306 | 5.6 | 153 |
| | 6.5 mM succinate + | 1 × F/T | 8.0 | 307 | 5.6 | 150 |
| | 185 mM sorbitol + | 3 × F/T | 8.1 | 308 | 5.7 | 151 |
| | 0.02% PS20, | 6 × F/T | 8.1 | 307 | 5.7 | 151 |
| | pH 5.7 | 5° C. | 8.8 | 306 | 5.7 | 151 |

TABLE 26-continued

Initial values and values after 1 / 3 / 6 F/T cycles of opalescence in FNU, osmolality in
mOsm/kg, pH-values and protein conc. in g/L.

| Formulation | Components | Sampling time point | Opalescence FNU | Osmolality mOsmol · kg$^{-1}$ | pH | Protein conc. g · L$^{-1}$ |
|---|---|---|---|---|---|---|
| F2 | 10 mM acetate + | initial | 4.8 | 304 | 5.7 | 153 |
|  | 200 mM sorbitol + | 1 × F/T | 5.2 | 305 | 5.6 | 152 |
|  | 0.02% PS20, | 3 × F/T | 4..8 | 306 | 5.6 | 153 |
|  | pH 5.7 | 6 × F/T | 5.4 | 306 | 5.7 | 152 |
|  |  | 5° C. | 5.6 | 306 | 5.7 | 150 |
| F3 | 10 mM acetate + | initial | 11.1 | 292 | 5.7 | 153 |
|  | 50 mM L-arginie | 1 × F/T | 11.8 | 292 | 5.6 | 152 |
|  | HCl + 110 mM | 3 × F/T | 12.1 | 292 | 5.6 | 152 |
|  | sorbitol + 0.02% | 6 × F/T | 12.2 | 251 | 5.6 | 153 |
|  | PS20, pH 5.7 | 5° C. | 11.5 | 292 | 5.6 | 150 |
| F4 | 10 mM succinate + | initial | 10.6 | 306 | 6 1 | 154 |
|  | 185 mM sorbitol + | 1 × F/T | 11.1 | 296 | 6.1 | 150 |
|  | 0.02% PS20, | 3 × F/T | 12.1 | 300 | 6.1 | 151 |
|  | pH 6.2 | 6 × F/T | 11.3 | 301 | 6.1 | 151 |
|  |  | 5° C. | 11.3 | 300 | 6.1 | 151 |
| F5 | 10 mM acetate + | initial | 4.7 | 307 | 5.6 | 154 |
|  | 95 mM mannitol + | 1 × F/T | 4.9 | 302 | 5.6 | 151 |
|  | 95 mM trehalose + | 3 × F/T | 5.4 | 305 | 5.6 | 153 |
|  | 0.02% PS20, | 6 × F/T | 5.1 | 305 | 5.6 | 153 |
|  | pH 5.7 | 5° C. | 4.9 | 306 | 5.6 | 150 |
| F6 | 10 mM acetate + | initial | 4.5 | 309 | 5.0 | 152 |
|  | 185 mM trehlaose + | 1 × F/T | 4.7 | 306 | 5.6 | 152 |
|  | 0.02% PS20, | 3 × F/T | 5.0 | 109 | 5.6 | 152 |
|  | pH 5.7 | 6 × F/T | 4.8 | 309 | 5.6 | 151 |
|  |  | 5° C. | 4.7 | 309 | 5.5 | 150 |
| F7 | 10 mM acetate + | initial | 10.6 | 307 | 5.7 | 152 |
|  | 50 mM L-arginine | 1 × F/T | 11.2 | 303 | 5.6 | 151 |
|  | HCl + 110 mM | 3 × F/T | 11.8 | 301 | 5.6 | 151 |
|  | trehalose + 0.02% | 6 × F/T | 11.0 | 305 | 5.5 | 153 |
|  | PS20, pH 5.7 | 5° C | 12.0 | 304 | 5.6 | 152 |
| F8 | 44 mM succinate + | initial | 6.2 | 300 | 5.9 | 148 |
|  | 185 mM | 1 × F/T | 6.4 | 291 | 5.9 | 150 |
|  | trehalose + | 3 × F/T | 6.7 | 256 | 5.9 | 151 |
|  | 0.02% P520, | 6 × F/T | 6.3 | 295 | 5.9 | 152 |
|  | pH 6.0 | 5° C. | 6.2 | 296 | 5.9 | 151 |
| F9 | 4.4 mM succinate + | initial | 11.9 | 303 | 5.9 | 153 |
|  | 50 mM L | 1 × F/T | 12.4 | 294 | 5.9 | 151 |
|  | arginine HCl + | 3 × F/T | 12.9 | 296 | 5.8 | 153 |
|  | 110 mM trehalose + | 6 × F/T | 12.3 | 295 | 5.8 | 153 |
|  | 0.02% PS20, | 5° C. | 11.8 | 295 | 5.9 | 150 |
|  | pH 6.0 |  |  |  |  |  |
| F10 | 4.4 mM succinate + | initial | 6.0 | 314 | 5.9 | 153 |
|  | 95 mM mannitol + | 1 × F/T | 5 8 | 298 | 5.9 | 151 |
|  | 95 mM trehalose + | 3 × F/T | 6.6 | 298 | 5.8 | 150 |
|  | 0.02% PS20, | 6 × F/T | 6.1 | 298 | 5.8 | 153 |
|  | pH 6.0 | 5° C. | 5.9 | 301 | 5.9 | 150 |
| F11 | Buffer-free, 200 | initial | 3.4 | 322 | 5.6 | 154 |
|  | mM trehalose, | 1 × F/T | 3.3 | 305 | 5.6 | 150 |
|  | 0.02% PS20, | 3 × F/T | 3.7 | 306 | 5.6 | 151 |
|  | pH 5.7 | 6 × F/T | 3.6 | 305 | 5.7 | 153 |
|  |  | 5° C. | 3.6 | 306 | 5.5 | 152 |
| F12 | Excipient-free, | initial | 3.5 | 29 | 5.6 | 151 |
|  | 0.02% PS20, | 1 × F/T | 3.8 | 25 | 5.6 | 152 |
|  | pH 5.7 | 3 × F/T | 4.0 | 25 | 5.6 | 151 |
|  |  | 6 × F/T | 3.8 | 25 | 5.5 | 151 |
|  |  | 5° C. | 3.6 | 27 | 5.6 | 151 |

Binding Activity

The results of the SPR (Biacore) measurements of the IL23 binding activity show that the freeze/thaw cycles do not influence the binding activity of the molecule. The binding activity ranges between 96-117%.

Results and Discussion

The measured opalescence depended on the formulation. The pH value, osmolality, opalescence and protein concentrations as well as binding of IL-23 essentially remained unchanged and thus stable for all formulations over the entire investigation period regardless of the stress condition (F/T & hold time at 5° C.).

6.3.3. Measurement of Particles

The subsequent table summarizes the number of particles for each STP. No clear trends could be observed for all formulations being tested. The formulations F3, F7 and F9 show a slightly increased amount of SVP in comparison to other formulations being tested. This observation was mainly seen for the SVP≥2 μm and ≥10 μm.

TABLE 27

Subvisible Particles - MFI: Initial values and values after one, three and six F/T
cycles and three weeks at 5° C.

| Treatment | Particle size | Number of measured particles | | | | | | | | | | | |
| | | F1 | F2 | F3 | F4 | F5 | F6 | F7 | F8 | F9 | F10 | F11 | F12 |
|---|---|---|---|---|---|---|---|---|---|---|---|---|---|
| Initial | ≥2 μm | 505 | 1104 | 1604 | 723 | 508 | 1046 | 878 | 1259 | 622 | 1255 | 1314 | 673 |
| | ≥10 μm | 44 | 32 | 50 | 34 | 31 | 38 | 18 | 71 | 19 | 38 | 41 | 36 |
| | ≥25 μm | 2 | 2 | 2 | 2 | 2 | 3 | 2 | 7 | 2 | 1 | 2 | 2 |
| 1× F/T | ≥2 μm | 1443 | 660 | 2426 | 831 | 710 | 883 | 2784 | 1260 | 2557 | 1070 | 925 | 1759 |
| | ≥10 μm | 49 | 19 | 639 | 18 | 38 | 21 | 683 | 28 | 995 | 45 | 35 | 63 |
| | ≥25 μm | 1 | 0 | 6 | 2 | 5 | 2 | 1 | 2 | 8 | 4 | 1 | 2 |
| 3× F/T | ≥2 μm | 1485 | 836 | 2764 | 1440 | 717 | 656 | 3501 | 698 | 2708 | 901 | 520 | 1513 |
| | ≥10 μm | 79 | 42 | 898 | 56 | 49 | 44 | 604 | 34 | 950 | 60 | 30 | 59 |
| | ≥25 μm | 6 | 6 | 10 | 3 | 2 | 3 | 10 | 5 | 3 | 5 | 5 | 3 |
| 6× F/T | ≥2 μm | 1392 | 1008 | 4551 | 1214 | 714 | 1121 | 3265 | 1051 | 2752 | 810 | 925 | 1868 |
| | ≥10 μm | 81 | 41 | 1089 | 31 | 48 | 69 | 518 | 38 | 1209 | 60 | 43 | 54 |
| | ≥25 μm | 7 | 10 | 41 | 4 | 9 | 6 | 17 | 1 | 5 | 7 | 3 | 3 |
| 5° C. | ≥2 μm | 1780 | 1259 | 2222 | 1341 | 555 | 784 | 2148 | 879 | 2825 | 1343 | 983 | 2131 |
| | ≥10 μm | 121 | 37 | 439 | 54 | 32 | 35 | 599 | 17 | 815 | 50 | 38 | 80 |
| | ≥25 μm | 4 | 1 | 6 | 6 | 3 | 4 | 2 | 1 | 2 | 6 | 3 | 7 |

Results and Discussion

While for ≥2 μm particles similar trends are observed, a slight increase of particles having a size of ≥10 μm was observed for F3, F7 and F9 compared to others. For ≥25 μm particles, a slight increase for F3 after 6× F/T was observed. Overall, particle formation was no major issue during F/T for all tested formulations.

6.4. Further Analytics and Results

In addition, further analytics were performed for the twelve formulations tested with the following results (freeze/thaw cycles were as described above).

The weak cation exchange chromatography (WCX) showed that the percentage of the distribution of the main peak, APG and BPG remained at a constant level for all formulations tested during the study. The levels of the main peak, APG and BPG did not change significantly over 6 freeze/thaw cycles. The main peak ranged from 65-67%, the APG content from 21-23% the BPG content from about 11-14%. No differences between the formulations were observed.

6.5. Summary of Results

The results can be summarized as follows:

Visual inspection: After six F/T cycles, no observations could be made during visual inspection for all formulations.

SVP: Regarding the sub-visible particle level no major issues could be observed. There was a slight increase for F3, F7 and F9 compared to other formulations but significantly below specifications of Pharmacopeia.

HP-SEC & UP-SEC: For the test methods with a focus on protein integrity like HP-SEC and UP-SEC F3 turned out to be the most stable formulation and F4 as the least stable. F12 without any buffer or excipients exhibited an acceptable stability during freeze/thaw cycles.

IEC: For the results of the IEC no discrimination for any formulation could be observed. The F/T-cycles do not negatively influence the contribution of APG and BPG.

Opalescence: The opalescence depends on the formulation and ranges from 4 FNU in an excipient-free or buffer-free formulation to 13 FNU.

The pH value, osmolality, opalescence and protein concentrations as well as binding remained unchanged for all formulations over the entire investigation period regardless of the stress condition (F/T & hold time at 5° C.).

It can be summarized that most of the formulations being tested in this example are viable formulations for a 150 mg/mL formulation. Only minor effects of the freeze/thaw stress on protein stability were observed. Due to medical concern with formulations containing sorbitol, these formulations may be found less advantageous in order to also address fructose-intolerant patients. Nevertheless, for other patients sorbitol-containing solutions may be found useful. All in all, only minor differences in stability-indicating parameters could be detected between formulations following exposure to F/T. For example the formulation F3 was most stable in monomer content (HP-SEC) but contrarily an increased level of subvisible particles could be detected.

7. Impact of the pH on the Formulation Stability

The impact of the pH value on the stability of 150 mg/mL risankizumab formulations were tested with the formulations shown in Table 28.

TABLE 28

Composition of formulations.

| Formulation | pH | Acetate | Trehalose | Polysorbate 20 |
|---|---|---|---|---|
| F1 | 5.0 | 10 mM | 185 mM | 0.2 mg/mL |
| F2 | 5.2 | | | |
| F3 | 5.5 | | | |
| F4 | 5.7 | | | |
| F5 | 5.9 | | | |
| F6 | 6.2 | | | |

7.1. Preparation of Formulations

The formulations were prepared as described above.

7.2. Analytics

Measurements of the samples were performed at 1, 3, 6, 9, 12, 18, 24 and 36 months storage, as well as initially before storage. Various methods for analysis were used, including HIC, UP-SEC, IEC, as well as viscosity, break loose and gliding force and binding specificity measurements. Further details on the utilized analysis methods are described below.

7.3. Results 7.3.1. Measurement of the Monomer Content

The monomer content was measured as in the previous examples using UP-SEC analysis, the results are shown in Table 29.

TABLE 29

| | | UP-SEC-Monomer-measurements in % of the formulations having different pH-values. | | | | | |
| Storage condition | Storage time, months | F1 | F2 | F3 | F4 | F5 | F6 |
|---|---|---|---|---|---|---|---|
| initial | 0 | 98.3 | 98.3 | 98.2 | 98.0 | 97.8 | 97.3 |
| 5° C. | 3 | 98.1 | 98.1 | 97.9 | 97.7 | 97.4 | 96.8 |
| 5° C. | 6 | 98.0 | 98.0 | 97.8 | 97.6 | 97.4 | 96.9 |
| 5° C. | 9 | 97.5 | 97.5 | 97.3 | 97.2 | 97.0 | 96.5 |
| 5° C. | 12 | 97.5 | 97.5 | 97.4 | 97.2 | 97.0 | 96.5 |
| 5° C. | 18 | 97.6 | 97.6 | 97.5 | 97.4 | 97.2 | 96.8 |
| 5° C. | 24 | 97.3 | 97.4 | 97.3 | 97.2 | 97.0 | 96.6 |
| 5° C. | 36 | 97.1 | 97.0 | 97.0 | 96.9 | 96.8 | 96.0 |
| 25° C. | 1 | 97.6 | 97.6 | 97.4 | 97.2 | 97.0 | 96.4 |
| 25° C. | 3 | 96.4 | 96.6 | 96.5 | 96.4 | 96.1 | 95.7 |
| 25° C. | 6 | 95.1 | 95.4 | 95.7 | 95.7 | 95.5 | 95.1 |
| 25° C. | 9 | 93.4 | 94.0 | 94.4 | 94.5 | 94.4 | 94.0 |
| 25° C. | 12 | 92.3 | 93.1 | 93.8 | 93.9 | 93.9 | 93.5 |
| 40° C. | 1 | 94.2 | 94.6 | 94.9 | 94.8 | 94.7 | 94.3 |
| 40° C. | 3 | 87.6 | 89.0 | 90.3 | 90.6 | 90.8 | 90.7 |

Results and Discussion

The monomer content measurements show that the tested formulations were stable over the tested range of pH values from pH 5.0 to 6.2. Therefore, a broad range of pH values is applicable in order to obtain high stability formulations of 150 mg/mL risankizumab. High monomer values were obtained for pH values around 5.7, whereas relatively low monomer contents were measured for more acidic conditions of about pH 5.0 (see for instance last measurement points of pH 5.0 at 25° C. or 40° C.). Hence, formulations of high concentrations of risankizumab (here 150 mg/mL) having a pH of about 5.7 proved to be particularly advantageous, in particular in the provided formulations of the present example.

7.3.2. Measurement of the HMW Content

Also the HMW content of the formulations was determined using UP-SEC, whereby following results were obtained:

TABLE 30

| | | UP-SEC-HMW measurements in % of the formulations having different pH-values. | | | | | |
| Storage condition | Storage time, months | F1 | F2 | F3 | F4 | F5 | F6 |
|---|---|---|---|---|---|---|---|
| initial | 0 | 0.8 | 0.9 | 1.1 | 1.2 | 1.4 | 1.9 |
| 5° C. | 3 | 1.0 | 1.1 | 1.3 | 1.4 | 1.8 | 2.4 |
| 5° C. | 6 | 1.1 | 1.2 | 1.4 | 1.6 | 1.8 | 2.3 |
| 5° C. | 9 | 1.3 | 1.4 | 1.6 | 1.7 | 1.9 | 2.4 |
| 5° C. | 12 | 1.4 | 1.4 | 1.6 | 1.7 | 2.0 | 2.4 |
| 5° C. | 18 | 1.4 | 1.5 | 1.6 | 1.7 | 1.9 | 2.3 |
| 5° C. | 24 | 1.8 | 1.8 | 1.9 | 2.1 | 2.3 | 2.7 |
| 5° C. | 36 | 1.8 | 1.9 | 2.0 | 2.1 | 2.3 | 2.8 |
| 25° C. | 1 | 1.3 | 1.4 | 1.6 | 1.8 | 2.1 | 2.7 |
| 25° C. | 3 | 1.7 | 1.8 | 2.1 | 2.3 | 2.6 | 3.0 |
| 25° C. | 6 | 2.1 | 2.2 | 2.3 | 2.4 | 2.6 | 3.1 |
| 25° C. | 9 | 2.6 | 2.6 | 2.9 | 2.8 | 3.0 | 3.4 |
| 25° C. | 12 | 2.9 | 2.9 | 2.8 | 3.0 | 3.1 | 3.5 |
| 40° C. | 1 | 2.5 | 2.5 | 2.7 | 2.9 | 3.1 | 3.6 |
| 40° C. | 3 | 4.9 | 4.5 | 4.3 | 4.5 | 4.6 | 4.8 |

Results and Discussion

The HMW content correlates with the monomer measurements. Overall, the tested formulations were stable over a range of pH values. Particular low increases of the HMW contents were obtained for pH values around 5.7. However, higher pH values (e.g. a pH of 6.2) appear to have led to slightly higher HMW values.

7.3.3. Measurement of the LMW Content

The LMW content was measured by UP-SEC analysis, which revealed following results:

TABLE 31

| | | UP-SEC-LMW-measurements in % of the formulations having different pH-values. | | | | | |
| Storage condition | Storage time, months | F1 | F2 | F3 | F4 | F5 | F6 |
|---|---|---|---|---|---|---|---|
| initial | 0 | 0.8 | 0.8 | 0.8 | 0.8 | 0.8 | 0.8 |
| 5° C. | 3 | 0.9 | 0.8 | 0.8 | 0.8 | 0.8 | 0.8 |
| 5° C. | 6 | 0.9 | 0.8 | 0.9 | 0.9 | 0.8 | 0.8 |
| 5° C. | 9 | 1.2 | 1.2 | 1.1 | 1.1 | 1.1 | 1.1 |
| 5° C. | 12 | 1.1 | 1.1 | 1.1 | 1.0 | 1.0 | 1.0 |
| 5° C. | 18 | 1.0 | 0.9 | 0.9 | 0.9 | 0.9 | 0.9 |
| 5° C. | 24 | 0.9 | 0.8 | 0.8 | 0.7 | 0.7 | 0.7 |
| 5° C. | 36 | 1.1 | 1.1 | 1.0 | 1.0 | 0.9 | 1.2 |
| 25° C. | 1 | 1.2 | 1.1 | 1.0 | 1.0 | 1.0 | 1.0 |
| 25° C. | 3 | 1.8 | 1.6 | 1.4 | 1.4 | 1.4 | 1.3 |
| 25° C. | 6 | 2.8 | 2.4 | 2.0 | 1.9 | 1.9 | 1.8 |
| 25° C. | 9 | 4.1 | 3.5 | 2.7 | 2.8 | 2.7 | 2.6 |
| 25° C. | 12 | 4.8 | 4.1 | 3.4 | 3.1 | 3.0 | 3.0 |
| 40° C. | 1 | 3.3 | 2.9 | 2.5 | 2.3 | 2.2 | 2.1 |
| 40° C. | 3 | 7.5 | 6.5 | 5.4 | 5.0 | 4.7 | 4.5 |

Results and Discussion

The LMW content correlates with the monomer measurements. Particular low increases of the LMW contents were obtained for pH values around 5.7. However, lower pH values appear to have led to slightly higher LMW values. Overall, the tested formulations were stable over a range of pH values.

7.3.4. Measurement of Species by Ion Exchange Chromatography (IEC)

Measurement of the ionic species was performed by ionic exchange chromatography. The results were then sorted into the main peak, acidic peak groups (APG) and basic peak groups (BPG).

TABLE 32

| | | IEC measurements of the main peak in % of the formulations having different pH-values. | | | | | |
| Storage condition | Storage time, months | F1 | F2 | F3 | F4 | F5 | F6 |
|---|---|---|---|---|---|---|---|
| initial | 0 | 72 | 71 | 71 | 72 | 72 | 71 |
| 5° C. | 3 | 71 | 71 | 71 | 71 | 70 | 70 |
| 5° C. | 6 | 70 | 70 | 70 | 70 | 70 | 70 |
| 5° C. | 12 | 68 | 70 | 71 | 71 | 71 | 71 |
| 5° C. | 18 | 67 | 69 | 70 | 70 | 71 | 70 |
| 5° C. | 24 | 65 | 67 | 68 | 69 | 69 | 68 |
| 5° C. | 36 | 65 | 66 | 68 | 69 | 69 | 69 |
| 25° C. | 1 | 68 | 68 | 69 | 69 | 69 | 69 |
| 25° C. | 3 | 61 | 62 | 63 | 64 | 64 | 65 |
| 25° C. | 6 | 52 | 54 | 57 | 58 | 59 | 60 |
| 25° C. | 12 | 39 | 43 | 48 | 50 | 51 | 53 |
| 40° C. | 1 | 46 | 48 | 50 | 52 | 54 | 55 |
| 40° C. | 3 | 25 | 26 | 28 | 31 | 33 | 35 |

TABLE 33

IEC measurements of APG in % of the formulations having different pH-values.

| Storage condition | Storage time, months | F1 | F2 | F3 | F4 | F5 | F6 |
|---|---|---|---|---|---|---|---|
| initial | 0 | 22 | 22 | 22 | 22 | 22 | 22 |
| 5° C. | 3 | 22 | 22 | 23 | 23 | 23 | 23 |
| 5° C. | 6 | 23 | 23 | 23 | 23 | 23 | 23 |
| 5° C. | 12 | 20 | 20 | 20 | 20 | 21 | 21 |
| 5° C. | 18 | 22 | 22 | 23 | 23 | 23 | 23 |
| 5° C. | 24 | 20 | 21 | 21 | 21 | 22 | 22 |
| 5° C. | 36 | 21 | 22 | 22 | 22 | 23 | 23 |
| 25° C. | 1 | 23 | 24 | 24 | 24 | 24 | 24 |
| 25° C. | 3 | 27 | 28 | 28 | 27 | 28 | 27 |
| 25° C. | 6 | 32 | 33 | 33 | 33 | 32 | 32 |
| 25° C. | 12 | 34 | 37 | 39 | 39 | 38 | 38 |
| 40° C. | 1 | 37 | 38 | 39 | 38 | 37 | 37 |
| 40° C. | 3 | 55 | 59 | 61 | 60 | 59 | 58 |

TABLE 34

IEC measurements of BPG in % of the formulations having different pH-values.

| Storage condition | Storage time, months | F1 | F2 | F3 | F4 | F5 | F6 |
|---|---|---|---|---|---|---|---|
| initial | 0 | 6 | 6 | 7 | 6 | 7 | 7 |
| 5° C. | 3 | 7 | 7 | 7 | 7 | 7 | 7 |
| 5° C. | 6 | 7 | 7 | 7 | 7 | 7 | 7 |
| 5° C. | 12 | 12 | 10 | 9 | 9 | 8 | 8 |
| 5° C. | 18 | 11 | 9 | 8 | 7 | 7 | 6 |
| 5° C. | 24 | 15 | 13 | 11 | 10 | 9 | 9 |
| 5° C. | 36 | 15 | 12 | 10 | 9 | 8 | 8 |
| 25° C. | 1 | 9 | 8 | 8 | 7 | 8 | 8 |
| 25° C. | 3 | 12 | 11 | 9 | 9 | 8 | 8 |
| 25° C. | 6 | 16 | 13 | 10 | 9 | 9 | 8 |
| 25° C. | 12 | 27 | 20 | 14 | 11 | 10 | 9 |
| 40° C. | 1 | 17 | 14 | 11 | 10 | 9 | 9 |
| 40° C. | 3 | 20 | 15 | 10 | 9 | 8 | 7 |

Results and Discussion

The IEC measurements show overall that the tested formulations were stable. All pH values led to high contents of the main peak. Noteworthy, an intermediate pH value of 5.7 and pH values around 5.7 showed a good compromise in comparison to the highest and lowest tested pH values, which showed an increase in APG or BPG species, respectively. Therefore, a pH of approximately 5.7 proved to be advantageous.

7.3.5. Measurement of Species by Hydrophobic Interaction Chromatography (HIC)

Measurement of the variants/subspecies of risankizumab was performed by hydrophobic interaction chromatography (HIC). The results were then sorted into the main peak, pre-peaks and post-peaks.

TABLE 35

HIC measurements of the main peak in % of the formulations having different pH-values.

| Storage condition | Storage time, months | F1 | F2 | F3 | F4 | F5 | F6 |
|---|---|---|---|---|---|---|---|
| initial | 0 | 96.8 | 96.7 | 96.7 | 96.7 | 96.4 | 96.0 |
| 5° C. | 3 | 96.7 | 96.7 | 96.7 | 96.6 | 96.3 | 95.8 |

TABLE 35-continued

HIC measurements of the main peak in % of the formulations having different pH-values.

| Storage condition | Storage time, months | F1 | F2 | F3 | F4 | F5 | F6 |
|---|---|---|---|---|---|---|---|
| 5° C. | 6 | 96.7 | 96.7 | 96.7 | 96.5 | 96.5 | 95.9 |
| 5° C. | 12 | 97.2 | 97.2 | 97.1 | 97.1 | 96.9 | 96.6 |
| 5° C. | 18 | 96.0 | 96.1 | 96.2 | 96.1 | 95.9 | 95.6 |
| 5° C. | 24 | 96.7 | 96.7 | 96.9 | 96.8 | 96.7 | 96.5 |
| 5° C. | 36 | 95.3 | 95.4 | 95.7 | 95.7 | 95.7 | 95.4 |
| 25° C. | 1 | 96.2 | 96.1 | 96.1 | 95.9 | 95.7 | 95.3 |
| 25° C. | 3 | 95.4 | 95.3 | 95.4 | 95.4 | 95.1 | 94.7 |
| 25° C. | 6 | 94.7 | 95.0 | 95.1 | 95.1 | 95.1 | 94.8 |
| 25° C. | 12 | 93.8 | 94.1 | 94.6 | 94.7 | 94.7 | 94.4 |
| 40° C. | 1 | 93.6 | 94.2 | 94.3 | 94.2 | 94.2 | 93.6 |
| 40° C. | 3 | 88.5 | 89.8 | 90.4 | 90.8 | 90.7 | 90.7 |

TABLE 36

HIC measurements of pre-peaks in % of the formulations having different pH-values.

| Storage condition | Storage time, months | F1 | F2 | F3 | F4 | F5 | F6 |
|---|---|---|---|---|---|---|---|
| initial | 0 | 1.8 | 1.7 | 1.7 | 1.6 | 1.6 | 1.6 |
| 5° C. | 3 | 1.9 | 1.9 | 1.8 | 1.8 | 1.8 | 1.8 |
| 5° C. | 6 | 1.9 | 1.9 | 1.7 | 1.8 | 1.6 | 1.7 |
| 5° C. | 12 | 1.6 | 1.5 | 1.4 | 1.3 | 1.3 | 1.3 |
| 5° C. | 18 | 2.1 | 2.0 | 1.8 | 1.8 | 1.7 | 1.6 |
| 5° C. | 24 | 1.8 | 1.7 | 1.5 | 1.4 | 1.4 | 1.4 |
| 5° C. | 36 | 2.2 | 2.0 | 1.7 | 1.5 | 1.5 | 1.4 |
| 25° C. | 1 | 2.1 | 2.1 | 2.0 | 1.9 | 2.0 | 1.9 |
| 25° C. | 3 | 2.8 | 2.7 | 2.4 | 2.3 | 2.3 | 2.5 |
| 25° C. | 6 | 3.3 | 3.0 | 2.7 | 2.5 | 2.4 | 2.3 |
| 25° C. | 12 | 4.1 | 3.6 | 3.1 | 2.8 | 2.7 | 2.6 |
| 40° C. | 1 | 3.7 | 3.3 | 3.1 | 3.0 | 2.8 | 3.0 |
| 40° C. | 3 | 7.5 | 6.4 | 6.1 | 5.6 | 5.5 | 5.4 |

TABLE 37

HIC measurements of post-peaks in % of the formulations having different pH-values.

| Storage condition | Storage time, months | F1 | F2 | F3 | F4 | F5 | F6 |
|---|---|---|---|---|---|---|---|
| initial | 0 | 1.5 | 1.6 | 1.6 | 1.7 | 2.0 | 2.4 |
| 5° C. | 3 | 1.4 | 1.4 | 1.6 | 1.7 | 1.9 | 2.5 |
| 5° C. | 6 | 1.4 | 1.4 | 1.6 | 1.7 | 1.9 | 2.3 |
| 5° C. | 12 | 1.2 | 1.2 | 1.4 | 1.6 | 1.7 | 2.1 |
| 5° C. | 18 | 1.9 | 1.9 | 2.0 | 2.1 | 2.4 | 2.8 |
| 5° C. | 24 | 1.5 | 1.6 | 1.6 | 1.7 | 1.9 | 2.1 |
| 5° C. | 36 | 2.5 | 2.6 | 2.6 | 2.8 | 2.8 | 3.2 |
| 25° C. | 1 | 1.8 | 1.8 | 2.0 | 2.2 | 2.3 | 2.9 |
| 25° C. | 3 | 1.8 | 1.9 | 2.2 | 2.2 | 2.6 | 2.9 |
| 25° C. | 6 | 2.1 | 2.1 | 2.3 | 2.4 | 2.5 | 2.9 |
| 25° C. | 12 | 2.0 | 2.1 | 2.2 | 2.4 | 2.5 | 2.9 |
| 40° C. | 1 | 2.7 | 2.6 | 2.6 | 2.8 | 2.9 | 3.5 |
| 40° C. | 3 | 4.1 | 3.8 | 3.5 | 3.6 | 3.8 | 3.9 |

Results and Discussion

The HIC measurements show overall that the tested formulations were stable. All pH values led to high contents of the main peak. Noteworthy, an intermediate pH value of 5.7 and pH values around 5.7 showed a good compromise in comparison to the highest and lowest tested pH values, which showed an increase in pre- and post-peaks, respectively.

7.3.6. Binding Activity

Measurement of the binding activity of risankizumab against IL-23 was performed using the Biacore T200. Following results were obtained:

TABLE 38

| | | | | | | | |
|---|---|---|---|---|---|---|---|
| Binding activity in % of the formulations having different pH-values. | | | | | | | |
| Storage condition | Storage time, months | F1 | F2 | F3 | F4 | F5 | F6 |
| initial | 0 | 103 | 103 | 103 | 106 | 105 | 107 |
| 5° C. | 6 | 101 | 104 | 102 | 103 | 104 | 103 |
| 5° C. | 12 | 94 | 97 | 96 | 93 | 97 | 99 |
| 5° C. | 18 | 104 | 102 | 102 | 106 | 105 | 105 |
| 5° C. | 24 | 102 | 96 | 101 | 100 | 97 | 102 |
| 5° C. | 36 | 95 | 97 | 96 | 95 | 96 | 98 |
| 25° C. | 3 | 109 | 107 | 106 | 106 | 103 | 103 |
| 25° C. | 6 | 105 | 99 | 99 | 100 | 103 | 103 |
| 25° C. | 12 | 93 | 101 | 93 | 94 | 92 | 97 |
| 40° C. | 3 | 98 | 100 | 100 | 98 | 97 | 101 |

TABLE 39

| | | | | | | | |
|---|---|---|---|---|---|---|---|
| Specific binding activity in % of the formulations having different pH-values. | | | | | | | |
| Storage condition | Storage time, months | F1 | F2 | F3 | F4 | F5 | F6 |
| initial | 0 | 100 | 100 | 100 | 100 | 100 | 100 |
| 5° C. | 6 | 100 | 99 | 99 | 99 | 99 | 99 |
| 5° C. | 12 | 99 | 100 | 100 | 100 | 100 | 100 |
| 5° C. | 18 | 99 | 99 | 99 | 100 | 100 | 100 |
| 5° C. | 24 | 99 | 99 | 99 | 99 | 99 | 99 |
| 5° C. | 36 | 100 | 100 | 100 | 100 | 100 | 100 |
| 25° C. | 3 | 99 | 99 | 99 | 99 | 99 | 99 |
| 25° C. | 6 | 98 | 98 | 99 | 98 | 99 | 98 |
| 25° C. | 12 | 98 | 98 | 98 | 98 | 98 | 98 |
| 40° C. | 3 | 96 | 96 | 97 | 97 | 98 | 98 |

Results and Discussion

The binding activity measurement show overall high values of the tested formulations. Hence, the tested formulations stabilize risankizumab such that a high binding activity at a pH range from 5.0 to 6.2 was achieved.

7.3.7. Measurement of the Opalescence

Furthermore, the opalescence of the formulations was measured. The opalescence slightly changes over the time of analysis but remained overall highly constant ranging from 3 to 11. The results indicate that the formulations are overall stable. Noteworthy, lower pH values in general showed lower opalescence (3 to 6 FNU for pH 5.0) than higher pH values (7 to 11 FNU for pH 6.2). The intermediate pH of 5.7 had a opalescence ranging from 5 to 7 FNU, indicating that providing formulations having a pH of about 5.7 is advantageous, in particular in formulations according to the present example.

7.3.8. Measurement of the Viscosity and Syringe Gliding and Break Loose Forces

As further parameters, the viscosity and the syringe forces were measured, which include the average and maximal gliding force, as well as the break loose force. Following results were obtained:

TABLE 40

| | | | | | | | |
|---|---|---|---|---|---|---|---|
| Measurement of the viscosity in mPas of the tested formulations having different pH-values over time. | | | | | | | |
| Storage condition | Storage time, months | F1 | F2 | F3 | F4 | F5 | F6 |
| initial | 0 | 8.5 | 8.8 | 9.2 | 9.6 | 9.9 | 10.3 |
| 5° C. | 6 | 8.5 | 8.6 | 9.0 | 9.2 | 9.5 | 10.0 |
| 5° C. | 12 | 8.7 | 8.7 | 8.9 | 9.3 | 9.7 | 10.1 |
| 5° C. | 24 | 8.8 | 9.0 | 9.3 | 9.5 | 9.4 | 10.4 |
| 5° C. | 36 | 8.6 | 8.7 | 8.9 | 9.4 | 9.8 | 10.3 |
| 25° C. | 6 | 8.7 | 8.8 | 8.9 | 9.2 | 9.5 | 10.0 |
| 25° C. | 12 | 8.7 | 8.5 | 9.0 | 9.3 | 9.7 | 10.3 |

TABLE 41

| | | | | | | | |
|---|---|---|---|---|---|---|---|
| Measurement of the maximal gliding force in N of the tested formulations having different pH-values over time. | | | | | | | |
| Storage condition | Storage time, months | F1 | F2 | F3 | F4 | F5 | F6 |
| initial | 0 | 6.3 | 5.9 | 6.0 | 6.6 | 6.0 | 7.1 |
| 5° C. | 3 | 6.4 | 6.9 | 6.3 | 6.5 | 6.5 | 7.0 |
| 5° C. | 6 | 8.4 | 7.1 | 6.3 | 6.3 | 6.2 | 6.7 |
| 5° C. | 9 | 7.7 | 8.5 | 6.4 | 6.3 | 7.1 | 6.9 |
| 5° C. | 12 | 9.4 | 7.6 | 6.6 | 6.9 | 7.3 | 6.8 |
| 5° C. | 18 | 9.2 | 10.4 | 8.4 | 6.5 | 6.9 | 7.0 |
| 5° C. | 24 | 9.0 | 8.2 | 7.7 | 7.7 | 6.9 | 6.6 |
| 5° C. | 36 | 9.2 | 8.3 | 7.7 | 7.7 | 6.9 | 7.1 |
| 25° C. | 1 | 7.0 | 8.6 | 7.3 | 6.4 | 6.0 | 5.6 |
| 25° C. | 3 | 11.8 | 10.0 | 8.5 | 7.3 | 8.3 | 6.8 |
| 25° C. | 6 | 12.4 | 11.9 | 11.0 | 11.2 | 8.4 | 7.2 |
| 25° C. | 9 | 12.9 | 13.3 | 13.2 | 10.7 | 11.1 | 8.4 |
| 25° C. | 12 | 13.6 | 16.7 | 13.7 | 11.9 | 12.5 | 10.2 |
| 40° C. | 1 | 10.8 | 10.3 | 11.8 | 8.7 | 7.9 | 7.2 |
| 40° C. | 3 | 18.1 | 20.9 | 20.6 | 18.0 | 17.1 | 13.4 |

TABLE 42

| | | | | | | | |
|---|---|---|---|---|---|---|---|
| Measurement of the average gliding force in N of the tested formulations having different pH-values over time. | | | | | | | |
| Storage condition | Storage time, months | F1 | F2 | F3 | F4 | F5 | F6 |
| initial | 0 | 5.9 | 5.6 | 5.6 | 6.1 | 5.7 | 6.5 |
| 5° C. | 3 | 5.9 | 6.3 | 5.8 | 6.0 | 6.1 | 6.5 |
| 5° C. | 6 | 7.4 | 6.5 | 5.9 | 5.9 | 5.9 | 6.4 |
| 5° C. | 9 | 6.9 | 7.7 | 6.0 | 5.9 | 6.6 | 6.5 |
| 5° C. | 12 | 8.1 | 6.8 | 6.2 | 6.5 | 6.8 | 6.4 |
| 5° C. | 18 | 8.1 | 9.2 | 7.6 | 6.1 | 6.5 | 6.6 |
| 5° C. | 24 | 7.9 | 7.2 | 7.0 | 7.1 | 6.4 | 6.2 |
| 5° C. | 36 | 8.0 | 7.6 | 7.1 | 7.1 | 6.5 | 6.7 |
| 25° C. | 1 | 6.5 | 7.5 | 6.6 | 6.0 | 5.7 | 5.4 |
| 25° C. | 3 | 9.8 | 8.8 | 7.7 | 6.9 | 7.6 | 6.4 |
| 25° C. | 6 | 10.1 | 9.7 | 9.0 | 9.6 | 7.6 | 6.8 |
| 25° C. | 9 | 10.6 | 11.1 | 10.8 | 8.6 | 9.3 | 7.6 |
| 25° C. | 12 | 10.8 | 13.5 | 10.8 | 9.7 | 9.9 | 8.6 |
| 40° C. | 1 | 9.2 | 8.5 | 9.6 | 7.5 | 7.1 | 6.6 |
| 40° C. | 3 | 14.1 | 15.8 | 14.5 | 12.9 | 12.5 | 10.5 |

TABLE 43

Measurement of the break loose force in N of the tested
formulations having different pH-values over time.

| Storage condition | Storage time, months | F1 | F2 | F3 | F4 | F5 | F6 |
|---|---|---|---|---|---|---|---|
| initial | 0 | 3.9 | 3.9 | 4.1 | 4.1 | 4.1 | 4.1 |
| 5° C. | 3 | 4.9 | 4.9 | 5.2 | 5.1 | 5.1 | 5.0 |
| 5° C. | 6 | 4.4 | 4.4 | 4.5 | 4.6 | 4.6 | 4.6 |
| 5° C. | 9 | 4.0 | 4.0 | 4.0 | 4.2 | 4.1 | 4.1 |
| 5° C. | 12 | 4.7 | 4.6 | 4.6 | 4.6 | 4.7 | 4.7 |
| 5° C. | 18 | 4.7 | 4.6 | 4.7 | 4.8 | 4.8 | 4.9 |
| 5° C. | 24 | 4.6 | 4.4 | 4.6 | 4.6 | 4.6 | 4.9 |
| 5° C. | 36 | 4.5 | 4.5 | 4.7 | 4.7 | 4.7 | 4.6 |
| 25° C. | 1 | 4.4 | 4.6 | 4.7 | 5.0 | 4.6 | 4.4 |
| 25° C. | 3 | 5.5 | 5.5 | 5.7 | 5.7 | 5.7 | 5.5 |
| 25° C. | 6 | 5.4 | 5.3 | 5.2 | 5.4 | 5.2 | 5.4 |
| 25° C. | 9 | 5.4 | 5.2 | 5.3 | 5.0 | 5.0 | 5.0 |
| 25° C. | 12 | 5.4 | 5.3 | 5.3 | 5.3 | 5.3 | 5.4 |
| 40° C. | 1 | 5.4 | 5.3 | 5.4 | 5.5 | 5.4 | 5.3 |
| 40° C. | 3 | 7.0 | 6.7 | 6.7 | 6.2 | 6.5 | 6.1 |

Results and Discussion

The viscosity measurements revealed a slightly higher viscosity for higher pH values. Thus lower pH values, such as pH 5.7, may be found advantageous in order to obtain formulations having a lower viscosity. Note, the mechanical measurements of the gliding and break loose force revealed overall very similar performance.

7.4. Further Analytics and Results

In addition, further analytics were performed for the six formulations tested with the following results. Storage times and temperatures were as described above.

The protein concentration remained essentially constant over the storage time of 36, 24, 12 and 3 months at the different storage temperatures tested, respectively 5° C., 25° C. and 40° C. Small deviations of protein concentration (145-155 mg/ml (24 months) and 145-158 mg/mL (36 months)) are due to analytical variations.

The pH value remained essentially constant over the storage time of 36, 24, 12 and 3 months at the different storage temperatures tested, respectively 5° C., 25° C. and 40° C. Measured pH values were thus in a range from 4.9-6.3.

The osmolality remained essentially constant over the storage time of 36, 24, 12 and 3 months at the different storage temperatures tested, respectively 5° C., 25° C. and 40° C. The tested values ranged from 301-323 mOsm/kg.

The protein related particles and foreign particles remained essentially constantly low over the storage time at the different storage temperatures tested.

7.5. Summary of Results

The formulations were stable at all tested pH values over long storage times of up to 24 and 36 months. While temperatures appeared to have an impact on the stability (i.e. higher temperatures inducing more instability related effects), all formulations led to sufficient stability even at high temperatures.

In summary, a pH value of 5.7 and values around 5.7 (e.g. 5.5, 5.9) appeared under the used test conditions to result in an advantageous compromise regarding the storage parameters. For instance, the UP-SEC measurements showed intermediate to low HMW and LMW values for pH 5.7, while the highest and lowest pH each showed highest HMW and LMW contents, respectively. Similar results were obtained in the IEC and HIC measurements.

8. Impact of the Acetate Concentration on the Formulation Stability

Formulations containing different concentrations of acetate (see Table 44) were stored over different time points at three different temperatures (5° C., 25° C. and 40° C.).

TABLE 44

Composition of formulations.

| Formulation | Acetate/ mM | PS20 | Trehalose | pH |
|---|---|---|---|---|
| F1 | 0 | 0.2 mg/mL | 185 mM | 5.7 |
| F2 | 5 | | | |
| F3 | 10 | | | |
| F4 | 15 | | | |
| F5 | 20 | | | |

8.1. Preparation of Formulations

The formulations were prepared as described above.

8.2. Analytics

Measurements of the samples were performed at 1, 3, 6, 9, 12, 18, 24 and 36 months storage, as well as initially before storage. The storage temperatures were adjusted to 5° C., 25° C. or 40° C. Analytics were performed by measurement using an UP-SEC for monomer, HMW and LMW content and Biacore for the binding activity. Furthermore, the required forces for gliding and break loose force were measured, as well as the osmolality, opalescence and the pH value. Further details on the utilized analysis methods are described below.

8.3. Results 8.3.1. Measurement of the Monomer Content

UP-SEC analysis was performed to measure the monomer content. Following results were obtained.

TABLE 45

UP-SEC-Monomer-measurements in % of formulations
comprising varying amounts of acetate.

| Storage condition | Storage time, months | F1 | F2 | F3 | F4 | F5 |
|---|---|---|---|---|---|---|
| 5° C. | 0 | 97.9 | 97.9 | 97.9 | 98.0 | 98.0 |
| 5° C. | 3 | 97.6 | 97.6 | 97.7 | 97.7 | 97.7 |
| 5° C. | 6 | 97.5 | 97.5 | 97.6 | 97.6 | 97.5 |
| 5° C. | 9 | 97.2 | — | 97.3 | — | 97.3 |
| 5° C. | 12 | 97.2 | 97.2 | 97.3 | 97.3 | 97.3 |
| 5° C. | 18 | 97.4 | 97.4 | 97.4 | 97.4 | 97.5 |
| 5° C. | 24 | 97.2 | 97.2 | 97.3 | 97.2 | 97.3 |
| 5° C. | 36 | 97.0 | 97.0 | 97.1 | 97.1 | 97.0 |
| 25° C. | 0 | 97.9 | 97.9 | 97.9 | 98.0 | 98.0 |
| 25° C. | 1 | 97.3 | — | 97.3 | — | 97.4 |
| 25° C. | 3 | 96.4 | 96.4 | 96.4 | 96.4 | 96.4 |
| 25° C. | 6 | 95.7 | 95.7 | 95.7 | 95.7 | 95.6 |
| 25° C. | 9 | 94.7 | — | 94.6 | — | 94.6 |
| 25° C. | 12 | 94.1 | 94.1 | 94.1 | 94.1 | 94.1 |
| 40° C. | 0 | 97.9 | 97.9 | 97.9 | 98.0 | 98.0 |
| 40° C. | 1 | 95.2 | — | 95.2 | — | 95.2 |
| 40° C. | 3 | 90.9 | 90.8 | 90.8 | 90.7 | 90.8 |

Results and Discussion

The monomer measurements show that the formulation is stable over a range of acetate contents, indicating stability for buffer containing and buffer-free formulations with 150 mg/mL risankizumab and formulations according to the present example.

8.3.2. Measurement of the HMW Content

Also the HMW content of the formulations was determined via UP-SEC analysis with following results:

TABLE 46

| | | | | | | |
|---|---|---|---|---|---|---|
| UP-SEC-HMW measurements in % of formulations comprising varying amounts of acetate. | | | | | | |
| Storage condition | Storage time, months | F1 | F2 | F3 | F4 | F5 |
| 5° C. | 0 | 1.3 | 1.3 | 1.3 | 1.3 | 1.2 |
| 5° C. | 3 | 1.5 | 1.5 | 1.5 | 1.5 | 1.5 |
| 5° C. | 6 | 1.7 | 1.6 | 1.6 | 1.6 | 1.6 |
| 5° C. | 9 | 1.7 | — | 1.6 | — | 1.6 |
| 5° C. | 12 | 1.9 | 1.8 | 1.8 | 1.7 | 1.7 |
| 5° C. | 18 | 1.7 | 1.7 | 1.7 | 1.7 | 1.6 |
| 5° C. | 24 | 2.0 | 2.0 | 2.0 | 2.0 | 2.0 |
| 5° C. | 36 | 2.2 | 2.1 | 2.1 | 2.1 | 2.1 |
| 25° C. | 0 | 1.3 | 1.3 | 1.3 | 1.3 | 1.2 |
| 25° C. | 1 | 1.7 | — | 1.7 | — | 1.7 |
| 25° C. | 3 | 2.3 | 2.2 | 2.2 | 2.2 | 2.2 |
| 25° C. | 6 | 2.5 | 2.5 | 2.4 | 2.5 | 2.5 |
| 25° C. | 9 | 2.7 | — | 2.7 | — | 2.7 |
| 25° C. | 12 | 2.9 | 2.9 | 2.9 | 2.9 | 2.9 |
| 40° C. | 0 | 1.3 | 1.3 | 1.3 | 1.3 | 1.2 |
| 40° C. | 1 | 2.7 | — | 2.6 | — | 2.7 |
| 40° C. | 3 | 4.3 | 4.4 | 4.4 | 4.4 | 4.4 |

Results and Discussion

The HMW content measurements show that the formulation is stable over a range of acetate contents, indicating stability for buffer containing and buffer-free formulations with 150 mg/mL risankizumab and formulations according to the present example.

8.3.3. Measurement of the LMW Content

For LMW content measurements UP-SEC analysis was performed. Following results were obtained.

TABLE 47

| | | | | | | |
|---|---|---|---|---|---|---|
| UP-SEC-LMW-measurements in % of formulations comprising varying amounts of acetate. | | | | | | |
| Storage condition | Storage time, months | F1 | F2 | F3 | F4 | F5 |
| 5° C. | 0 | 0.8 | 0.9 | 0.9 | 0.8 | 0.8 |
| 5° C. | 3 | 0.9 | 0.9 | 0.9 | 0.8 | 0.8 |
| 5° C. | 6 | 0.8 | 0.9 | 0.9 | 0.9 | 0.9 |
| 5° C. | 9 | 1.1 | — | 1.1 | — | 1.1 |
| 5° C. | 12 | 1.0 | 1.0 | 1.0 | 1.0 | 1.0 |
| 5° C. | 18 | 0.9 | 0.9 | 0.9 | 0.9 | 0.9 |
| 5° C. | 24 | 0.8 | 0.8 | 0.8 | 0.8 | 0.8 |
| 5° C. | 36 | 0.9 | 0.9 | 0.8 | 0.9 | 0.9 |
| 25° C. | 0 | 0.8 | 0.9 | 0.9 | 0.8 | 0.8 |
| 25° C. | 1 | 1.0 | — | 1.0 | — | 0.9 |
| 25° C. | 3 | 1.4 | 1.4 | 1.4 | 1.4 | 1.4 |
| 25° C. | 6 | 1.8 | 1.8 | 1.9 | 1.8 | 1.9 |
| 25° C. | 9 | 2.7 | — | 2.7 | — | 2.7 |
| 25° C. | 12 | 3.0 | 3.0 | 3.0 | 3.0 | 3.0 |
| 40° C. | 0 | 0.8 | 0.9 | 0.9 | 0.8 | 0.8 |
| 40° C. | 1 | 2.2 | — | 2.2 | — | 2.2 |
| 40° C. | 3 | 4.8 | 4.8 | 4.8 | 4.8 | 4.9 |

The LMW measurements show that the formulation is stable over a range of acetate contents, indicating stability for buffer containing and buffer-free formulations.

8.3.4. Measurement of Binding Activity

In order to analyze whether the acetate content has an influence on the binding activity of risankizumab to IL-23, Biacore analysis was performed. The measurements of the binding activity show high binding activity against human IL-23 for all tested formulations and storage times ranging from 92-105% binding activity and 97-100% specific binding activity. These results support the advantageous stability of the tested formulations and indicate that acetate containing and buffer-free formulations are applicable according to the present disclosure.

8.3.5. Measurement of Osmolality

As the acetate content also has an influence on the osmolality of the formulation, this parameter was measured. The results are shown in Table 48.

TABLE 48

| | | | | | | |
|---|---|---|---|---|---|---|
| Osmolality in mOsm/kg of the formulations at different temperatures and storage times of formulations comprising varying amounts of acetate. | | | | | | |
| Storage condition | Storage time, months | F1 | F2 | F3 | F4 | F5 |
| 5° C. | 0 | 288 | 293 | 309 | 322 | 335 |
| 5° C. | 3 | 290 | 294 | 310 | 324 | 335 |
| 5° C. | 6 | 291 | 296 | 311 | 322 | 334 |
| 5° C. | 9 | 304 | — | 309 | — | 333 |
| 5° C. | 12 | 292 | 293 | 305 | 320 | 333 |
| 5° C. | 18 | 284 | 287 | 305 | 322 | 330 |
| 5° C. | 24 | 290 | 290 | 306 | 322 | 333 |
| 5° C. | 36 | 288 | 291 | 306 | 322 | 334 |
| 25° C. | 0 | 288 | 293 | 309 | 322 | 335 |
| 25° C. | 1 | 290 | — | 309 | — | 335 |
| 25° C. | 3 | 288 | 293 | 311 | 322 | 334 |
| 25° C. | 6 | 290 | 295 | 313 | 324 | 334 |
| 25° C. | 9 | 295 | — | 311 | — | 333 |
| 25° C. | 12 | 294 | 294 | 309 | 312 | 333 |
| 40° C. | 0 | 288 | 293 | 309 | 322 | 335 |
| 40° C. | 1 | 287 | — | 308 | — | 334 |
| 40° C. | 3 | 291 | 297 | 314 | 324 | 338 |

The measurements show that the osmolality varies from about 290 to 338 mOsm/kg depending on the amount of added acetate. The more acetate was added, the higher the measured osmolality. An osmolality of approximately 310 mOsm/kg is typically desired and an acetate concentration of 10 mM resulted in the tested formulations in a desired osmolality of around 310 mOsm/kg (measured range from 305 to 314 mOsm/kg). In case another concentration of acetate is required or desired, it may be advantageous to modify the content of the other compounds of the formulation (e.g., another excipient such as trehalose) to adjust the osmolality to approximately 310 mOsm/kg.

8.3.6. Measurement of Opalescence

The opalescence of the formulations of the present example was also measured to evaluate the stability. The measured opalescence is overall the same for the different formulations ranging between 4-9 FNU. Higher concentrations of acetate led to a slightly higher opalescence of 7-9 FNU for 20 mM acetate than lower concentrations (4-6 FNU for 0 mM acetate). All formulations according to the present example were stable in view of the measured opalescence.

8.3.7. Measurement of pH

In order to determine the pH stability of the formulations comprising varying amounts of buffer, i.e. acetate in this example, the pH values were measured over the time of storage at different temperatures. The results are shown in the subsequent table.

TABLE 49

Measured pH value for the formulations containing
varying amounts of acetate at 5, 25 or 40° C.
over varying storage times.

| Storage condition | Storage time, months | F1 | F2 | F3 | F4 | F5 |
|---|---|---|---|---|---|---|
| 5° C. | 0 | 5.8 | 5.8 | 5.8 | 5.8 | 5.8 |
| 5° C. | 3 | 5.8 | 5.8 | 5.7 | 5.8 | 5.8 |
| 5° C. | 6 | 5.8 | 5.8 | 5.8 | 5.8 | 5.8 |
| 5° C. | 9 | 5.8 | — | 5.8 | — | 5.8 |
| 5° C. | 12 | 5.7 | 5.8 | 5.8 | 5.7 | 5.8 |
| 5° C. | 18 | 5.7 | 5.8 | 5.8 | 5.8 | 5.7 |
| 5° C. | 24 | 5.8 | 5.8 | 5.8 | 5.8 | 5.8 |
| 5° C. | 36 | 5.8 | 5.8 | 5.8 | 5.8 | 5.8 |
| 25° C. | 0 | 5.8 | 5.8 | 5.8 | 5.8 | 5.8 |
| 25° C. | 1 | 5.8 | — | 5.7 | — | 5.7 |
| 25° C. | 3 | 5.8 | 5.7 | 5.8 | 5.8 | 5.7 |
| 25° C. | 6 | 5.8 | 5.8 | 5.8 | 5.8 | 5.8 |
| 25° C. | 9 | 5.8 | — | 5.8 | — | 5.8 |
| 25° C. | 12 | 5.7 | 5.8 | 5.7 | 5.7 | 5.8 |
| 40° C. | 0 | 5.8 | 5.8 | 5.8 | 5.8 | 5.8 |
| 40° C. | 1 | 5.8 | — | 5.8 | — | 5.7 |
| 40° C. | 3 | 5.7 | 5.7 | 5.7 | 5.8 | 5.7 |

Results and Discussion

The measurements of the pH value demonstrate that the pH is overall kept constant for the tested formulations according to the present example. Therefore, for all acetate contents, including a formulation comprising no acetate, the formulations were stable regarding the pH value.

8.3.8. Measurement of Gliding and Break Loose Forces

The maximal and average gliding force were measured as well as the break loose force for syringes containing the different formulations according to the present example. The results of these measurements are shown below.

TABLE 50

Maximum gliding force in N, initially and after the
indicated storage time at 5° C., 25° C. or 40° C. of
formulations comprising varying amounts of acetate.

| Storage condition | Storage time, months | F1 | F2 | F3 | F4 | F5 |
|---|---|---|---|---|---|---|
| 5° C. | 0 | 6.9 | 6.3 | 6.6 | 7.1 | 6.7 |
| 5° C. | 3 | 7.3 | 7.0 | 6.3 | 7.4 | 7.6 |
| 5° C. | 6 | 7.5 | 6.9 | 6.6 | 7.0 | 6.4 |
| 5° C. | 9 | 8.1 | — | 7.1 | — | 6.6 |
| 5° C. | 12 | 7.5 | 7.0 | 7.1 | 6.7 | 7.1 |
| 5° C. | 18 | 7.9 | 8.8 | 6.1 | 5.9 | 7.0 |
| 5° C. | 24 | 8.8 | 7.7 | 7.1 | 7.4 | 5.9 |
| 5° C. | 36 | 7.8 | 9.3 | 7.0 | 7.4 | 7.1 |
| 25° C. | 0 | 6.9 | 6.3 | 6.6 | 7.1 | 6.7 |
| 25° C. | 1 | 8.1 | — | 5.9 | — | 5.9 |
| 25° C. | 3 | 9.9 | 8.2 | 6.9 | 7.8 | 7.3 |
| 25° C. | 6 | 12.5 | 12.5 | 8.5 | 8.2 | 7.1 |
| 25° C. | 9 | 13.9 | — | 11.8 | — | 10.5 |
| 25° C. | 12 | 18.4 | 14.7 | 14.5 | 13.1 | 10.8 |
| 40° C. | 0 | 6.9 | 6.3 | 6.6 | 7.1 | 6.7 |
| 40° C. | 1 | 11.8 | — | 11.5 | — | 7.6 |
| 40° C. | 3 | 25.1 | 24.0 | 16.4 | 15.6 | 14.2 |

TABLE 51

Average gliding force in N, initially and after the
indicated storage time at 5° C., 25° C. or 40° C. of
formulations comprising varying amounts of acetate.

| Storage condition | Storage time, months | F1 | F2 | F3 | F4 | F5 |
|---|---|---|---|---|---|---|
| 5° C. | 0 | 6.3 | 6.0 | 6.2 | 6.6 | 6.2 |
| 5° C. | 3 | 6.5 | 6.4 | 6.0 | 6.8 | 6.9 |
| 5° C. | 6 | 7.0 | 6.5 | 6.2 | 6.6 | 6.1 |
| 5° C. | 9 | 7.2 | — | 6.6 | — | 6.2 |
| 5° C. | 12 | 6.9 | 6.5 | 6.6 | 6.3 | 6.7 |
| 5° C. | 18 | 7.2 | 7.9 | 5.8 | 5.7 | 6.6 |
| 5° C. | 24 | 8.2 | 7.2 | 6.6 | 7.0 | 5.6 |
| 5° C. | 36 | 7.0 | 8.1 | 6.6 | 6.8 | 6.7 |
| 25° C. | 0 | 6.3 | 6.0 | 6.2 | 6.6 | 6.2 |
| 25° C. | 1 | 7.3 | — | 5.5 | — | 5.7 |
| 25° C. | 3 | 8.2 | 7.5 | 6.5 | 6.9 | 6.7 |
| 25° C. | 6 | 10.5 | 10.5 | 7.6 | 7.6 | 6.7 |
| 25° C. | 9 | 11.1 | — | 9.5 | — | 9.1 |
| 25° C. | 12 | 14.0 | 11.9 | 11.5 | 10.2 | 8.9 |
| 40° C. | 0 | 6.3 | 6.0 | 6.2 | 6.6 | 6.2 |
| 40° C. | 1 | 9.5 | — | 8.8 | — | 6.8 |
| 40° C. | 3 | 17.2 | 16.2 | 11.9 | 12.0 | 10.4 |

TABLE 52

Break loose force in N, initially and after the indicated storage
time at 5° C., 25° C. or 40° C. of formulations comprising
varying amounts of acetate.

| Storage condition | Storage time, months | F1 | F2 | F3 | F4 | F5 |
|---|---|---|---|---|---|---|
| 5° C. | 0 | 4.1 | 4.0 | 3.9 | 3.8 | 4.1 |
| 5° C. | 3 | 4.5 | 4.6 | 4.3 | 4.4 | 4.4 |
| 5° C. | 6 | 4.5 | 4.3 | 4.3 | 4.1 | 4.4 |
| 5° C. | 9 | 4.2 | — | 4.5 | — | 4.3 |
| 5° C. | 12 | 4.5 | 4.4 | 4.3 | 4.3 | 4.3 |
| 5° C. | 18 | 4.6 | 4.5 | 4.7 | 4.5 | 4.5 |
| 5° C. | 24 | 4.7 | 4.6 | 4.6 | 4.6 | 4.7 |
| 5° C. | 36 | 4.5 | 4.6 | 4.7 | 4.5 | 4.6 |
| 25° C. | 0 | 4.1 | 4.0 | 3.9 | 3.8 | 4.1 |
| 25° C. | 1 | 4.3 | — | 4.3 | — | 4.7 |
| 25° C. | 3 | 5.0 | 5.4 | 5.0 | 4.8 | 5.2 |
| 25° C. | 6 | 5.1 | 5.4 | 5.1 | 5.0 | 5.2 |
| 25° C. | 9 | 5.2 | — | 5.2 | — | 4.7 |
| 25° C. | 12 | 5.5 | 5.7 | 5.5 | 5.1 | 5.4 |
| 40° C. | 0 | 4.1 | 4.0 | 3.9 | 3.8 | 4.1 |
| 40° C. | 1 | 5.2 | — | 5.0 | — | 5.3 |
| 40° C. | 3 | 6.3 | 6.0 | 6.0 | 5.9 | 6.0 |

Results and Discussion

The measurements of the gliding force and break loose force show that all formulations are stable and the gliding and break loose forces do not significantly increase over time. Noteworthy, the formulations that do not comprise acetate (F1) or very low concentrations of acetate (F2) show higher forces, indicating that it is useful to add buffer, such as acetate, particularly when aiming at minimizing the required forces applied to a syringe.

8.4. Further Analytics and Results

In addition, further analytics were performed for the five formulations tested with the following results. Storage times and temperatures were as described above.

The IEC main peak, APG and BPG content remained constant over 24 and 36 months at 5° C. No differences between the formulations were observed regarding the main peak, APG and BGP.

The HIC main peak content remained constant over 24 months at 5° C. in a range of 96.8-97.2%, as well as 1.4-1.7% pre peak and 1.5-1.9% post peak. Over 36 months at 5° C. HIC main peak contents in a range of 96.3-97.2% were obtained, as well as 1.4-1.7% pre peak and 1.5-2.2% post peak. At 25° C. for up to 12 months storage time main peak contents between 94.3-97.1% were obtained, as well as 1.4-3.0% pre peak and 1.5-2.7% post peak. At 40° C. for up to 3 months storage time main peak contents between 92.0-97.1% were obtained, as well as 1.4-4.6% pre peak and 1.5-3.4% post peak. No differences between the formulations were observed regarding the main peak, pre peak and post peak.

The protein concentration remained essentially constant up to a storage time of 24 and 36 months at the different storage temperatures tested. Small deviations of protein concentration are due to analytical variations, leading to ranges of 147-155 mg/mL (24 months) and 147-157 mg/mL (36 months).

The dynamic viscosity remained essentially constant up to a storage time of 24 and 36 months at the different storage temperatures tested. The dynamic viscosity was in a range of 8.9-10.0 mPas.

The protein related particles and foreign particles remained essentially constantly low over the storage time at the different storage temperatures tested.

8.5. Summary of Results

The tested formulations show overall comparable high stability. Therefore, both acetate containing and buffer-free formulations are suitable for the formulations according to the present disclosure. In view of the required force to be applied to the syringes, solutions containing a buffer such as an acetate buffer have proven to be advantageous over buffer-free formulations. Moreover, in order to achieve an osmolality of 310 mOsm/kg, an acetate content of 10 mM has proven to be suitable considering the other compounds present in the formulation according to the present example.

IV. Example 3: Analysis of Further Excipients

1. Influence of the PS20 Content in Shaking Experiments

Formulations were prepared (see Table 53) wherein the PS20 (polysorbate 20) content was varied from 0, 0.05, 0.075, 0.1, 0.2, 0.3 to 0.5 mg/mL and analyzed during shaking times of 0, 1, 5, 7, 14 and 21 days.

TABLE 53

Composition of formulations.

| Formulation | PS20/ mg/mL | Acetate | Trehalose | pH |
|---|---|---|---|---|
| F1 | 0.0 | 10 mM | 185 mM | 5.7 |
| F2 | 0.05 | | | |
| F3 | 0.075 | | | |
| F4 | 0.1 | | | |
| F5 | 0.2 | | | |
| F6 | 0.3 | | | |
| F7 | 0.5 | | | |

1.1. Preparation of Formulations

The formulations were prepared as described above. The formulations were packaged in 2R vials (1.0 mL) or pre-filled syringes (PFS, Neopak, 1.0 mL) for each formulation, as well as for the control and non-shaken formulations.

1.2. Analytics

Measurements of the samples were performed on day 0, 1, 5, 7, 14 and 21. Therefore, the total shaking duration was 21 days for both vial and PFS. The shaking was performed at room temperature (25° C.) at 200 U/min for vials (Orbital shaker) and the movement is adjusted to respective viscosity to ensure air bubble movement for PFS (Tilting shaker (Vari Mix Platform Rocker)). All samples were protected from light. The opalescence of the formulations was measured at the indicated measurement points. Further details on the utilized analysis methods are described below.

1.3. Results

Measurement of the Opalescence

To measure the stability of the formulations containing varying amounts of PS20 and subjected to a shaking stress, the opalescence was measured at different time points. The results obtained by the opalescence measurements are shown below:

TABLE 54

Opalescence in FNU of the formulations having varying amounts of PS20 in syringes.

| | | | Shaking time, days. Storage/shaking condition | | | | | |
|---|---|---|---|---|---|---|---|---|
| Formulation | PS20, g/l | 0 initial | 1 rocking shaker | 3 rocking shaker | 7 rocking shaker | 14 rocking shaker | 21 rocking shaker | no movement |
| F1_S | 0.00 | 8.18 | 8.26 | 8.48 | 11.00 | 15.20 | 19.96 | 7.13 |
| F2_S | 0.05 | 5.72 | 5.82 | 5.70 | 5.78 | 5.86 | 5.83 | 4.97 |
| F3_S | 0.08 | 5.90 | 5.95 | 5.68 | 6.53 | 6.13 | 5.67 | 5.49 |
| F4_S | 0.10 | 5.61 | 5.19 | 5.94 | 6.12 | 6.10 | 6.01 | 5.47 |
| F5_S | 0.20 | 6.32 | 5.93 | 5.60 | 6.12 | 6.33 | 6.30 | 5.12 |
| F6_S | 0.30 | 6.22 | 6.23 | 5.75 | 5.55 | 5.75 | 5.87 | 5.06 |
| F7_S | 0.50 | 6.10 | 5.77 | 5.61 | 6.01 | 7.33 | 5.78 | 5.32 |

TABLE 55

Opalescence in FNU of the formulations having varying amounts of PS20 in vials.

| | | | Shaking time, days. Storage/shaking conditon | | | | | |
|---|---|---|---|---|---|---|---|---|
| Formulation | PS20, g/l | 0 initial | 1 horizontal shaker | 3 horizontal shaker | 7 horizontal shaker | 14 horizontal shaker | 21 horizontal shaker | no movement |
| F1_V | 0.00 | 6.83 | 8.29 | 8.37 | 10.72 | 14.52 | 22.50 | 7.96 |
| F2_V | 0.05 | 6.70 | 5.70 | 6.10 | 5.45 | 5.91 | 5.72 | 5.46 |
| F3_V | 0.08 | 5.84 | 5.47 | 6.57 | 5.85 | 6.26 | 6.86 | 6.21 |
| F4_V | 0.10 | 5.67 | 5.10 | 6.24 | 5.39 | 5.75 | 6.28 | 5.81 |
| F5_V | 0.20 | 7.23 | 6.21 | 5.94 | 6.07 | 5.58 | 6.87 | 6.89 |
| F6_V | 0.30 | 6.60 | 5.20 | 5.89 | 5.36 | 5.78 | 5.61 | 5.66 |
| F7_V | 0.50 | 5.70 | 5.62 | 5.61 | 5.81 | 5.54 | 5.48 | 5.89 |

1.4. Summary of Results

The shaking study clearly revealed that formulations that do not comprise PS20 significantly increased in opalescence over the shaking time of 21 days. In contrast, all formulations that comprised PS20, i.e. even the lowest amount of 0.05 g/L, showed no increase in opalescence over time. The results substantiate the importance of a surfactant such as the non-ionic surfactant PS20 in formulations according to the present disclosure, in particular formulations comprising 150 mg/mL risankizumab.

2. Influence of the PS20 Content During Storage

The prepared formulations (see Table 53) were analyzed over different time points stored at three different temperatures (5° C., 25° C. and 40° C.).

2.1. Analytics

Measurements of the samples were performed at 1, 3, 6, 9, 12, 18, 24 and 36 months storage, as well as initially before storage. UP-SEC analysis was performed in order to determine the monomer, HMW and LMW contents. Moreover, sub-visible particle content, gliding force and break loose force were measured. Further details on the utilized analysis methods are described below.

2.2. Results 2.2.1. Measurement of the Monomer Content

The stability of the formulations was assessed by measuring the monomer content using the UP-SEC analysis. The results are shown below.

TABLE 56

UP-SEC-Monomer-measurements in % of formulations comprising varying amounts of PS20.

| Storage condition | Storage time, months | F1 | F2 | F3 | F4 | F5 | F6 | F7 |
|---|---|---|---|---|---|---|---|---|
| initial | 0 | 97.9 | 97.9 | 97.9 | 97.9 | 97.8 | 97.8 | 97.8 |
| 5° C. | 3 | 97.5 | 97.5 | 97.6 | 97.5 | 97.5 | 97.5 | 97.5 |
| 5° C. | 6 | 97.3 | 97.3 | 97.3 | 97.3 | 97.3 | 97.3 | 97.2 |
| 5° C. | 9 | 97.1 | 97.1 | 97.1 | 97.1 | 97.1 | 97.1 | 97.1 |
| 5° C. | 12 | 97.2 | 97.2 | 97.2 | 97.2 | 97.2 | 97.2 | 97.2 |
| 5° C. | 18 | 97.4 | 97.3 | 97.3 | 97.5 | 97.4 | 97.4 | 97.4 |
| 5° C. | 24 | 97.1 | 97.2 | 97.2 | 97.1 | 97.2 | 97.1 | 97.2 |
| 5° C. | 36 | 96.8 | 96.9 | 96.9 | 96.9 | 97.0 | 97.0 | 97.0 |
| 25° C. | 1 | 97.2 | 97.2 | 97.2 | 97.2 | 97.2 | 97.2 | 97.2 |
| 25° C. | 3 | 96.2 | 96.2 | 96.3 | 96.2 | 96.2 | 96.3 | 96.2 |
| 25° C. | 6 | 95.2 | 95.3 | 95.4 | 95.4 | 95.4 | 95.4 | 95.4 |
| 25° C. | 9 | 94.2 | 94.4 | 94.5 | 94.5 | 94.5 | 94.5 | 94.5 |
| 25° C. | 12 | 93.5 | 93.8 | 93.9 | 93.9 | 94.0 | 94.0 | 93.9 |
| 40° C. | 1 | 94.9 | 94.9 | 94.9 | 94.9 | 94.9 | 94.8 | 94.8 |
| 40° C. | 3 | 89.6 | 90.1 | 90.4 | 90.3 | 90.4 | 90.4 | 89.7 |

Results and Discussion

The monomer measurements show that the formulation is stable over a range of PS20 contents. Particular high monomer values were obtained for PS20 contents around 0.2 mg/mL.

2.2.2. Measurement of the HMW Content

The stability of the formulations was further assessed by measuring the HMW content, again using UP-SEC. The results are shown below.

TABLE 57

UP-SEC HMW measurements in % of formulations comprising varying amounts of PS20.

| Storage condition | Storage time, months | F1 | F2 | F3 | F4 | F5 | F6 | F7 |
|---|---|---|---|---|---|---|---|---|
| initial | 0 | 1.3 | 1.4 | 1.4 | 1.4 | 1.4 | 1.4 | 1.4 |
| 5° C. | 3 | 1.7 | 1.7 | 1.7 | 1.7 | 1.7 | 1.7 | 1.7 |
| 5° C. | 6 | 1.9 | 1.9 | 1.9 | 1.9 | 1.9 | 1.9 | 1.9 |
| 5° C. | 9 | 1.8 | 1.8 | 1.8 | 1.8 | 1.8 | 1.8 | 1.8 |
| 5° C. | 12 | 1.0 | 1.0 | 1.0 | 1.0 | 1.0 | 1.0 | 1.0 |
| 5° C. | 18 | 1.7 | 1.8 | 1.8 | 1.7 | 1.7 | 1.7 | 1.7 |
| 5° C. | 24 | 2.1 | 2.1 | 2.0 | 2.1 | 2.1 | 2.1 | 2.1 |
| 5° C. | 36 | 2.3 | 2.2 | 2.2 | 2.2 | 2.2 | 2.2 | 2.2 |
| 25° C. | 1 | 1.9 | 1.9 | 1.9 | 1.9 | 1.9 | 1.9 | 1.9 |
| 25° C. | 3 | 2.4 | 2.4 | 2.4 | 2.4 | 2.4 | 2.4 | 2.5 |
| 25° C. | 6 | 2.9 | 2.8 | 2.8 | 2.8 | 2.8 | 2.8 | 2.8 |
| 25° C. | 9 | 3.0 | 2.9 | 2.8 | 2.8 | 2.8 | 2.8 | 2.8 |
| 25° C. | 12 | 3.2 | 3.1 | 3.1 | 3.1 | 3.0 | 3.0 | 3.1 |
| 40° C. | 1 | 2.9 | 2.9 | 2.9 | 2.9 | 2.9 | 2.9 | 3.0 |
| 40° C. | 3 | 5.1 | 4.9 | 4.7 | 4.7 | 4.7 | 4.7 | 5.3 |

Results and Discussion

The HMW content correlates with the monomer measurements. Overall, the tested formulations were stable over a range of PS20 contents. Particular low increases of the HMW contents were obtained for PS20 contents of 0.2 mg/mL. However, highest and lowest tested PS20 contents appear to have led to slightly higher HMW values.

2.2.3. Measurement of the LMW Content

Also the LMW contents were measured using an UP-SEC and following results were obtained:

TABLE 58

UP-SEC-LMW-measurements in % of formulations comprising varying amounts of PS20.

| Storage condition | Storage time, months | F1 | F2 | F3 | F4 | F5 | F6 | F7 |
|---|---|---|---|---|---|---|---|---|
| initial | 0 | 0.8 | 0.8 | 0.8 | 0.8 | 0.8 | 0.8 | 0.8 |
| 5° C. | 3 | 0.8 | 0.8 | 0.8 | 0.8 | 0.8 | 0.8 | 0.8 |
| 5° C. | 6 | 0.8 | 0.8 | 0.8 | 0.8 | 0.8 | 0.8 | 0.8 |
| 5° C. | 9 | 1.1 | 1.1 | 1.1 | 1.1 | 1.1 | 1.1 | 1.1 |
| 5° C. | 12 | 1.9 | 1.8 | 1.8 | 1.8 | 1.8 | 1.8 | 1.8 |
| 5° C. | 18 | 0.8 | 1.0 | 1.0 | 0.8 | 0.9 | 0.9 | 0.9 |
| 5° C. | 24 | 0.8 | 0.8 | 0.8 | 0.8 | 0.8 | 0.8 | 0.8 |
| 5° C. | 36 | 0.9 | 0.9 | 0.9 | 0.9 | 0.9 | 0.9 | 0.9 |
| 25° C. | 1 | 1.0 | 1.0 | 1.0 | 1.0 | 1.0 | 1.0 | 0.9 |
| 25° C. | 3 | 1.4 | 1.3 | 1.3 | 1.4 | 1.4 | 1.3 | 1.3 |
| 25° C. | 6 | 1.9 | 1.9 | 1.8 | 1.8 | 1.8 | 1.8 | 1.8 |
| 25° C. | 9 | 2.8 | 2.7 | 2.7 | 2.7 | 2.7 | 2.7 | 2.7 |
| 25° C. | 12 | 3.3 | 3.1 | 3.1 | 3.1 | 3.0 | 3.0 | 3.0 |
| 40° C. | 1 | 2.2 | 2.3 | 2.2 | 2.2 | 2.2 | 2.3 | 2.3 |
| 40° C. | 3 | 5.3 | 5.1 | 5.0 | 5.0 | 4.9 | 4.9 | 5.0 |

Results and Discussion

The LMW content correlates with the monomer measurements. Overall, the tested formulations were stable over a range of PS20 contents. Particular low increases of the LMW contents were obtained for PS 20 contents of 0.2 mg/mL. The lowest tested PS20 content (see F1) appears to have led to slightly higher LMW values.

2.2.4. Measurement of the Opalescence

Moreover, the opalescence was measured for the formulations containing the varying amounts of PS20. The results are depicted below.

TABLE 59

Opalescence measurements in FNU of formulations comprising varying amounts of PS20.

| Storage condition | Storage time, months | F1 | F2 | F3 | F4 | F5 | F6 | F7 |
|---|---|---|---|---|---|---|---|---|
| initial | 0 | 8 | 6 | 6 | 6 | 6 | 6 | 6 |
| 5° C. | 3 | 7 | 6 | 6 | 6 | 7 | 6 | 6 |
| 5° C. | 6 | 6 | 6 | 6 | 6 | 7 | 6 | 6 |
| 5° C. | 9 | 12 | 5 | 7 | 6 | 6 | 7 | 8 |
| 5° C. | 12 | 11 | 10 | 8 | 7 | 7 | 6 | 7 |
| 5° C. | 18 | 19 | 9 | 12 | 8 | 7 | 7 | 6 |
| 5° C. | 24 | 13 | 6 | 7 | 7 | 7 | 7 | 7 |
| 5° C. | 36 | 12 | 6 | 7 | 7 | 7 | 7 | 7 |
| 25° C. | 1 | 6 | 6 | 5 | 6 | 5 | 6 | 6 |
| 25° C. | 3 | 6 | 6 | 6 | 6 | 6 | 6 | 6 |
| 25° C. | 6 | 6 | 6 | 6 | 7 | 7 | 7 | 7 |
| 25° C. | 9 | 6 | 6 | 6 | 7 | 6 | 7 | 8 |
| 25° C. | 12 | 7 | 7 | 7 | 7 | 8 | 7 | 9 |
| 40° C. | 1 | 7 | 6 | 6 | 6 | 6 | 7 | 6 |
| 40° C. | 3 | 7 | 6 | 6 | 7 | 7 | 7 | 8 |

Results and Discussion

The measurements show that at higher temperatures of 25 and 40° C. all formulations led to no increase in opalescence. However, at a temperature of 5° C. and later storage time points (e.g. 18, 24 and 36 months), formulation F1 (no PS20) showed an increase in opalescence. Hence, incorporating a surfactant such as the non-ionic surfactant PS20 is advantageous.

2.2.5. Measurement of the Sub-Visible Particle Content

The formulations were analyzed in regard to their sub-visible particle content (≥2 µm, ≥10 µm and ≥25 µm) over 24 and 36 months stored at 5° C.

TABLE 60

Measurement of the sub-visible particle content of particles with a size of ≥2, ≥10 and ≥25 µm stored for up to 24 and 36 months at 5° C. of formulations comprising varying amounts of PS20.

| Treat- ment | Particle size | Number of measured particles | | | | | | |
|---|---|---|---|---|---|---|---|---|
| | | F1 | F2 | F3 | F4 | F5 | F6 | F7 |
| Initial | ≥2 µm | 58318 | 1876 | 4832 | 3607 | 7780 | 5121 | 6578 |
| | ≥10 µm | 6061 | 70 | 99 | 88 | 312 | 111 | 278 |
| | ≥25 µm | 183 | 9 | 5 | 2 | 31 | 9 | 26 |
| 5° C., 3 months | ≥2 µm | 41237 | 1442 | 4559 | 9475 | 14173 | 10810 | 4201 |
| | ≥10 µm | 3650 | 48 | 170 | 225 | 177 | 224 | 94 |
| | ≥25 µm | 196 | 2 | 6 | 15 | 1 | 3 | 1 |
| 5° C., 6 months | ≥2 µm | 51615 | 4949 | 3580 | 5282 | 11069 | 16838 | 18125 |
| | ≥10 µm | 3501 | 38 | 48 | 45 | 71 | 105 | 131 |
| | ≥25 µm | 29 | 0 | 2 | 0 | 1 | 6 | 1 |
| 5° C., 9 months | ≥2 µm | 70311 | 11911 | 6453 | 6982 | 35316 | 6358 | 10660 |
| | ≥10 µm | 5195 | 42 | 17 | 60 | 60 | 33 | 79 |
| | ≥25 µm | 122 | 1 | 0 | 2 | 0 | 2 | 9 |
| 5° C., 12 months | ≥2 µm | 58322 | 16911 | 9064 | 28517 | 7761 | 15372 | 41782 |
| | ≥10 µm | 4529 | 121 | 183 | 360 | 141 | 132 | 295 |
| | ≥25 µm | 184 | 2 | 7 | 7 | 1 | 0 | 6 |
| 5° C., 18 months | ≥2 µm | 28849 | 4496 | 5760 | 9250 | 7025 | 18772 | 20556 |
| | ≥10 µm | 2939 | 79 | 84 | 123 | 56 | 181 | 232 |
| | ≥25 µm | 181 | 2 | 6 | 1 | 3 | 2 | 6 |
| 5° C., 24 months | ≥2 µm | 61469 | 5862 | 9427 | 7969 | 17688 | 37040 | 3688 |
| | ≥10 µm | 5407 | 84 | 163 | 197 | 355 | 290 | 148 |
| | ≥25 µm | 66 | 1 | 9 | 9 | 6 | 3 | 5 |
| 5° C., 36 months | ≥2 µm | 17157 | 4306 | 7984 | 12335 | 16377 | 21911 | 14799 |
| | ≥10 µm | 2255 | 49 | 54 | 146 | 172 | 136 | 65 |
| | ≥25 µm | 257 | 1 | 2 | 8 | 5 | 2 | 3 |

Results and Discussion

The measurements of the sub-visible particle content show that all formulations are stable at 5° C. for up to 24 and 36 months. Only formulations without PS20 (F1) appeared to result in some particle formation, substantiating that it is advantageous to add a surfactant such as the non-ionic surfactant PS20 to the formulations according to the present disclosure.

2.2.6. Measurement of the Gliding Force and Break Loose Force

The maximal and average gliding force as well as the break loose force were measured for the formulations comprising varying amounts of PS20. The results of the measurements are shown below.

TABLE 61

Maximal gliding force in N. The formulations comprised varying amounts of PS20.

| Storage condition | Storage time, months | F1 | F2 | F3 | F4 | F5 | F6 | F7 |
|---|---|---|---|---|---|---|---|---|
| initial | 0 | 7.2 | 7.1 | 6.2 | 6.5 | 6.4 | 6.3 | 6.9 |
| 5° C. | 3 | 7.8 | 7.4 | 8.1 | 6.8 | 6.8 | 6.5 | 6.4 |
| 5° C. | 6 | 7.7 | 7.0 | 6.7 | 6.6 | 6.1 | 6.5 | 6.7 |
| 5° C. | 9 | 8.7 | 6.4 | 7.4 | 7.6 | 6.7 | 6.6 | 8.2 |
| 5° C. | 12 | 7.1 | 7.5 | 6.7 | 7.2 | 5.9 | 6.7 | 7.3 |
| 5° C. | 18 | 8.9 | 7.4 | 6.1 | 6.9 | 6.1 | 7.4 | 7.1 |
| 5° C. | 24 | 8.1 | 6.2 | 7.6 | 8.0 | 7.2 | 6.7 | 7.1 |
| 5° C. | 36 | 9.2 | 8.5 | 9.1 | 7.0 | 7.5 | 6.7 | 7.2 |
| 25° C. | 1 | 7.4 | 6.5 | 6.4 | 6.8 | 6.6 | 6.1 | 6.2 |
| 25° C. | 3 | 8.1 | 7.0 | 7.4 | 7.7 | 7.0 | 7.7 | 7.7 |
| 25° C. | 6 | 8.1 | 7.3 | 9.4 | 8.9 | 9.9 | 9.6 | 10.8 |
| 25° C. | 9 | 7.2 | 11.9 | 10.2 | 9.8 | 11.2 | 11.3 | 12.6 |
| 25° C. | 12 | 8.4 | 11.1 | 12.0 | 13.6 | 12.8 | 15.1 | 16.1 |
| 40° C. | 1 | 7.7 | 8.1 | 9.2 | 11.2 | 8.7 | 9.5 | 8.6 |

TABLE 62

Average gliding force in N. The formulations comprised varying amounts of PS20.

| Storage condition | Storage time, months | F1 | F2 | F3 | F4 | F5 | F6 | F7 |
|---|---|---|---|---|---|---|---|---|
| initial | 0 | 6.5 | 6.5 | 5.8 | 6.1 | 5.9 | 5.9 | 6.4 |
| 5° C. | 3 | 7.1 | 6.7 | 7.3 | 6.3 | 6.2 | 6.0 | 6.0 |
| 5° C. | 6 | 6.8 | 6.5 | 6.3 | 6.2 | 5.7 | 6.1 | 6.2 |
| 5° C. | 9 | 7.5 | 6.1 | 6.7 | 6.9 | 6.3 | 6.1 | 7.2 |
| 5° C. | 12 | 6.4 | 6.8 | 6.4 | 6.8 | 5.7 | 6.2 | 6.7 |
| 5° C. | 18 | 7.9 | 7.0 | 5.8 | 6.4 | 5.8 | 6.8 | 6.6 |
| 5° C. | 24 | 7.2 | 5.9 | 7.0 | 7.3 | 6.7 | 6.4 | 6.6 |
| 5° C. | 36 | 7.8 | 7.7 | 8.2 | 6.6 | 6.8 | 6.4 | 6.6 |
| 25° C. | 1 | 6.7 | 6.0 | 6.0 | 6.4 | 6.2 | 5.8 | 5.8 |
| 25° C. | 3 | 7.4 | 6.5 | 6.9 | 7.2 | 6.3 | 7.0 | 7.2 |
| 25° C. | 6 | 7.3 | 6.9 | 8.4 | 7.8 | 8.0 | 8.3 | 9.2 |
| 25° C. | 9 | 6.4 | 10.0 | 8.5 | 8.6 | 9.1 | 9.5 | 9.9 |
| 25° C. | 12 | 7.7 | 9.6 | 10.0 | 11.2 | 10.5 | 12.1 | 12.4 |
| 40° C. | 1 | 6.9 | 7.0 | 7.9 | 9.2 | 7.0 | 8.0 | 7.5 |

TABLE 63

Break loose force in N. The formulations comprised varying amounts of PS20.

| Storage condition | Storage time, months | F1 | F2 | F3 | F4 | F5 | F6 | F7 |
|---|---|---|---|---|---|---|---|---|
| initial | 0 | 4.1 | 4.3 | 4.2 | 4.1 | 4.2 | 4.3 | 4.1 |
| 5° C. | 3 | 4.7 | 4.6 | 4.8 | 4.8 | 4.6 | 4.7 | 4.7 |
| 5° C. | 6 | 4.6 | 4.3 | 4.5 | 4.5 | 4.5 | 4.5 | 4.7 |
| 5° C. | 9 | 3.8 | 4.1 | 4.0 | 4.1 | 3.9 | 4.2 | 4.2 |
| 5° C. | 12 | 4.5 | 4.5 | 4.5 | 4.7 | 4.7 | 4.3 | 4.5 |
| 5° C. | 18 | 4.6 | 4.9 | 4.8 | 4.6 | 4.7 | 4.6 | 4.7 |
| 5° C. | 24 | 5.0 | 5.1 | 4.8 | 4.7 | 4.8 | 4.6 | 4.8 |
| 5° C. | 36 | 4.2 | 4.3 | 4.3 | 4.0 | 4.0 | 4.5 | 4.6 |
| 25° C. | 1 | 4.8 | 4.8 | 4.6 | 4.7 | 4.7 | 4.4 | 4.7 |
| 25° C. | 3 | 5.1 | 5.4 | 5.3 | 5.5 | 5.4 | 5.2 | 5.4 |
| 25° C. | 6 | 5.1 | 5.1 | 5.1 | 5.3 | 4.9 | 5.1 | 5.3 |
| 25° C. | 9 | 4.4 | 4.9 | 4.4 | 5.0 | 5.0 | 4.9 | 5.0 |
| 25° C. | 12 | 5.4 | 5.4 | 5.4 | 5.7 | 5.3 | 5.6 | 5.3 |
| 40° C. | 1 | 5.0 | 5.0 | 5.0 | 5.2 | 5.1 | 4.9 | 5.0 |
| 40° C. | 3 | 5.9 | 5.8 | 6.1 | 6.3 | 6.0 | 6.0 | 6.4 |

Results and Discussion

The measurements of the gliding force revealed relatively high gliding forces for high contents of PS20 of 0.5 g/L in comparison to the lower contents. While a content of 0 g/L showed lowest increase in gliding force, an intermediate concentration of 0.2 g/L showed a good compromise between high and low gliding force. Noteworthy, essentially no differences between the formulations in respect to the break loose force were observed.

2.3. Further Analytics and Results

In addition, further analytics were performed for the seven formulations tested with the following results. Storage times and temperatures were as described above.

The IEC main peak, APG and BPG content remained constant over 24 and 36 months at 5° C. No differences between the formulations were observed regarding the main peak, APG and BGP.

The HIC main peak content remained constant over 24 months at 5° C. in a range of 96.5-97.3%, as well as 1.4-1.7% pre peak and 1.4-1.9% post peak. Over 36 months at 5° C. HIC main peak contents in a range of 95.9-97.3% were obtained, as well as 1.4-1.7% pre peak and 1.4-2.4% post peak. At 25° C. for up to 12 months storage time main peak contents between 93.9-96.8% were obtained, as well as 1.4-3.0% pre peak and 1.7-2.7% post peak. At 40° C. for up to 3 months storage time main peak contents between 90.3-95.2% were obtained, as well as 2.5-6.0% pre peak and 2.3-3.7% post peak. No differences between the formulations were observed regarding the main peak, pre peak and post peak.

The specific binding activity remained essentially constant up to a storage time of 24 and 36 months at the different storage temperatures tested. The specific binding activity was in a range of 97-101%.

The protein concentration remained essentially constant up to a storage time of 24 and 36 months at the different storage temperatures tested. Small deviations of protein concentration are due to analytical variations, leading to ranges of 147-155 mg/mL (24 months) and 147-159 mg/mL (36 months).

The pH value remained essentially constant up to a storage time of 24 and 36 months at the different storage temperatures tested. The pH was in a range of 5.7-5.9.

The osmolality remained essentially constant up to a storage time of 24 and 36 months at the different storage temperatures tested. The tested values ranged from 305-322 mOsm/kg.

The dynamic viscosity remained essentially constant up to a storage time of 24 and 36 months at the different storage temperatures tested. The dynamic viscosity was in a range of 9.2-11.0 mPas.

The protein related particles and foreign particles remained essentially constantly low over the storage time at the different storage temperatures tested.

2.4. Summary of Results

In summary, the tested formulations were stable over long term storage up to 24 and 36 months at temperatures ranging from 5° C. up to 40° C. In particular, formulations comprising a surfactant such as PS20 were found to be stable, whereas formulation lacking PS20 showed some formation of sub-visible particles and an increase in opalescence. Also the LMW content was slightly increased for formulations lacking PS20. A particularly suitable content of a surfactant such as the non-ionic surfactant PS20 appeared to be 0.2 g/L under the tested conditions.

3. Variation of the Trehalose Content

In this example the trehalose concentration was varied from 145, 165, 185, 205 to 225 mM and analyzed over different time points stored at three different temperatures (5° C., 25° C. and 40° C.). The prepared formulations are shown in Table 64.

TABLE 64

| Composition of formulations. | | | | |
| --- | --- | --- | --- | --- |
| Formulation | Trehalose/ mM | PS20/ mg/mL | Acetate/mM | pH |
| F1 | 145 | 0.2 | 10 | 5.7 |
| F2 | 165 | | | |
| F3 | 185 | | | |
| F4 | 205 | | | |
| F5 | 225 | | | |

3.1. Analytics

Measurements of the samples were performed at 1, 3, 6, 9, 12, 18, 24 and 36 months storage, as well as initially before storage. Further details on the utilized analysis methods are described below.

3.2. Results 3.2.1. Measurement of the Monomer Content

The stability of the formulations comprising varying trehalose amounts was assessed by measuring the monomer content using an UP-SEC analysis, revealing the results shown below.

TABLE 65

| UP-SEC-Monomer-measurements in % of formulations comprising different amounts of trehalose. | | | | | | |
| --- | --- | --- | --- | --- | --- | --- |
| Storage condition | Storage time, months | F1 | F2 | F3 | F4 | F5 |
| 5° C. | 0 | 98.1 | 98.0 | 98.0 | 98.1 | 98.0 |
| 5° C. | 3 | 97.7 | 97.7 | 97.7 | 97.7 | 97.6 |
| 5° C. | 6 | 97.6 | 97.5 | 97.5 | 97.5 | 97.5 |
| 5° C. | 9 | 97.2 | — | 97.2 | — | 97.1 |
| 5° C. | 12 | 97.2 | 97.3 | 97.2 | 97.3 | 97.2 |
| 5° C. | 18 | 97.5 | 97.5 | 97.4 | 97.4 | 97.3 |
| 5° C. | 24 | 97.2 | 97.1 | 97.2 | 97.2 | 97.1 |
| 5° C. | 36 | 97.0 | 97.0 | 97.0 | 97.0 | 96.9 |
| 25° C. | 0 | 98.1 | 98.0 | 98.0 | 98.1 | 98.0 |
| 25° C. | 1 | 97.2 | — | 97.3 | — | 97.2 |
| 25° C. | 3 | 96.5 | 96.5 | 96.4 | 96.4 | 96.3 |
| 25° C. | 6 | 95.7 | 95.6 | 95.6 | 95.6 | 95.6 |
| 25° C. | 9 | 94.6 | — | 94.6 | — | 94.6 |
| 25° C. | 12 | 94.1 | 94.1 | 94.1 | 94.1 | 94.1 |
| 40° C. | 0 | 98.1 | 98.0 | 98.0 | 98.1 | 98.0 |
| 40° C. | 1 | 95.0 | — | 95.0 | — | 95.0 |
| 40° C. | 3 | 90.7 | 90.8 | 90.8 | 90.7 | 90.8 |

Results and Discussion

The monomer measurements show that the formulation is stable over a range of trehalose contents, indicating stability over a range of trehalose contents.

3.2.2. Measurement of the HMW Content

The HMW contents of the formulations were measured using UP-SEC. The results of the analysis are shown below.

TABLE 66

| | Storage time, months | | | | | |
|---|---|---|---|---|---|---|
| Storage condition | | F1 | F2 | F3 | F4 | F5 |

UP-SEC HMW measurements in % of formulations comprising different amounts of trehalose.

| Storage condition | Storage time, months | F1 | F2 | F3 | F4 | F5 |
|---|---|---|---|---|---|---|
| 5° C. | 0 | 1.1 | 1.1 | 1.1 | 1.1 | 1.2 |
| 5° C. | 3 | 1.4 | 1.4 | 1.5 | 1.4 | 1.5 |
| 5° C. | 6 | 1.5 | 1.6 | 1.6 | 1.6 | 1.6 |
| 5° C. | 9 | 1.7 | — | 1.7 | — | 1.8 |
| 5° C. | 12 | 1.8 | 1.8 | 1.8 | 1.8 | 1.9 |
| 5° C. | 18 | 1.7 | 1.7 | 1.7 | 1.7 | 1.8 |
| 5° C. | 24 | 2.0 | 2.0 | 2.0 | 2.0 | 2.1 |
| 5° C. | 36 | 2.1 | 2.1 | 2.2 | 2.2 | 2.2 |
| 25° C. | 0 | 1.1 | 1.1 | 1.1 | 1.1 | 1.2 |
| 25° C. | 1 | 1.7 | — | 1.7 | — | 1.7 |
| 25° C. | 3 | 2.2 | 2.2 | 2.2 | 2.2 | 2.3 |
| 25° C. | 6 | 2.4 | 2.4 | 2.5 | 2.4 | 2.5 |
| 25° C. | 9 | 2.7 | — | 2.7 | — | 2.8 |
| 25° C. | 12 | 2.9 | 3.0 | 3.0 | 3.0 | 3.0 |
| 40° C. | 0 | 1.1 | 1.1 | 1.1 | 1.1 | 1.2 |
| 40° C. | 1 | 2.8 | — | 2.7 | — | 2.8 |
| 40° C. | 3 | 4.4 | 4.3 | 4.3 | 4.3 | 4.4 |

Results and Discussion

The HMW content measurements show that the formulation is stable over a range of trebalose contents.

3.2.3. Measurement of the LMW Content.

Also the LMW content was measured vis UP-SBC for the formulations comprising varying amounts of trebalose. The results are shown below.

TABLE 67

UP-SEC-LMW-measurements in % of formulations comprising different amounts of trehalose.

| Storage condition | Storage time, months | F1 | F2 | F3 | F4 | F5 |
|---|---|---|---|---|---|---|
| 5° C. | 0 | 0.9 | 0.9 | 0.9 | 0.9 | 0.9 |
| 5° C. | 3 | 0.9 | 0.9 | 0.9 | 0.9 | 0.9 |
| 5° C. | 6 | 0.9 | 0.9 | 0.9 | 0.9 | 0.9 |
| 5° C. | 9 | 1.1 | — | 1.1 | — | 1.1 |
| 5° C. | 12 | 1.0 | 1.0 | 1.0 | 1.0 | 1.0 |
| 5° C. | 18 | 0.9 | 0.9 | 0.9 | 0.9 | 0.9 |
| 5° C. | 24 | 0.8 | 0.8 | 0.8 | 0.8 | 0.8 |
| 5° C. | 36 | 0.9 | 0.8 | 0.9 | 0.9 | 0.9 |
| 25° C. | 0 | 0.9 | 0.9 | 0.9 | 0.9 | 0.9 |
| 25° C. | 1 | 1.1 | — | 1.0 | — | 1.0 |
| 25° C. | 3 | 1.4 | 1.4 | 1.4 | 1.4 | 1.4 |
| 25° C. | 6 | 1.9 | 1.9 | 1.9 | 1.9 | 1.9 |
| 25° C. | 9 | 2.6 | — | 2.6 | — | 2.6 |
| 25° C. | 12 | 2.9 | 2.9 | 2.9 | 3.0 | 2.9 |
| 40° C. | 0 | 0.9 | 0.9 | 0.9 | 0.9 | 0.9 |
| 40° C. | 1 | 2.3 | — | 2.3 | — | 2.3 |
| 40° C. | 3 | 4.9 | 4.9 | 4.9 | 4.9 | 4.9 |

Results and Discussion

The LMW measurements show that the formulation is stable over a range of trehalose contents.

3.2.4. Measurement of Binding Activity

The binding activity of the risankizumab comprised in the formulations according to the present disclosure was measured. The measurements of antigen binding show high binding activity to IL-23 for all tested formulations ranging from 92-122% binding activity and 96-100% specific binding activity. These results support the advantageous stability of the tested formulations and indicate that trehalose containing formulations at various concentrations are applicable according to the present disclosure.

3.2.5. Measurement of the Osmolality

The osmolality was measured in order to assure that the tested formulations have a suitable osmolality for injection. The results are shown below:

TABLE 68

Measured osmolality in mOsm/kg of the formulations comprising varying amounts of trehalose.

| Storage condition | Storage time, months | F1 | F2 | F3 | F4 | F5 |
|---|---|---|---|---|---|---|
| 5° C. | 0 | 246 | 274 | 309 | 337 | 376 |
| 5° C. | 3 | 247 | 277 | 307 | 340 | 378 |
| 5° C. | 6 | 247 | 275 | 309 | 338 | 375 |
| 5° C. | 9 | 251 | — | 310 | — | 380 |
| 5° C. | 12 | 245 | 274 | 305 | 335 | 375 |
| 5° C. | 18 | 248 | 271 | 303 | 340 | 370 |
| 5° C. | 24 | 248 | 277 | 308 | 339 | 376 |
| 5° C. | 36 | 248 | 275 | 307 | 338 | 374 |
| 25° C. | 0 | 246 | 274 | 309 | 337 | 376 |
| 25° C. | 1 | 248 | — | 307 | — | 373 |
| 25° C. | 3 | 252 | 287 | 311 | 338 | 378 |
| 25° C. | 6 | 246 | 276 | 310 | 335 | 371 |
| 25° C. | 9 | 253 | — | 310 | — | 380 |
| 25° C. | 12 | 241 | 278 | 302 | 336 | 377 |
| 40° C. | 0 | 246 | 274 | 309 | 337 | 376 |
| 40° C. | 1 | 245 | | 310 | | 373 |
| 40° C. | 3 | 249 | 278 | 312 | 340 | 379 |

The osmolality values range from around 245 to 380 mOsm/kg for trehalose concentrations from 145 to 225 mM. As an optimal osmolality is around 310 mOsm/kg, it can be advantageous to provide formulations having such osmolality. This can for instance be achieved using a trehalose concentration of 185 mM in combination with the formulation according to the present example.

3.3. Further Analytics and Results

In addition, further analytics were performed for the five formulations tested (storage times and temperatures were as described above).

The IEC main peak, APG and BPG content remained constant over 24 and 36 months at 5° C. No differences between the formulations were observed regarding the main peak, APG and BGP.

The HIC main peak content remained constant over 24 months at 5° C. in a range of 96.4-97.4%, as well as 1.4-1.8% pre peak and 1.2-2.0% post peak. Over 36 months at 5° C. HIC main peak contents in a range of 96.0-97.4% were obtained, as well as 1.4-1.8% pre peak and 1.2-2.3% post peak. At 25° C. for up to 12 months storage time main peak contents between 94.2-97.4% were obtained, as well as 1.4-3.0% pre peak and 1.2-2.8% post peak. At 40° C. for up to 3 months storage time main peak contents between 90.3-97.4% were obtained, as well as 1.4-5.9% pre peak and 1.2-3.7% post peak. No differences between the formulations were observed regarding the main peak, pre peak and post peak.

The protein concentration remained essentially constant up to a storage time of 24 and 36 months at the different storage temperatures tested. Small deviations of protein concentration are due to analytical variations, leading to ranges of 145-153 mg/ml (24 months) and 148-158 mg/mL (36 months).

The pH value remained essentially constant up to a storage time of 24 and 36 months at the different storage temperatures tested. The pH was in a range of 5.7-5.9.

The opalescence remained essentially constant up to a storage time of 24 and 36 months at the different storage temperatures tested. The opalescence was in a range of 5-9 FNU.

The dynamic viscosity remained essentially constant up to a storage time of 24 and 36 months at the different storage temperatures tested. The dynamic viscosity was in a range of 8.9-10.3 mPas.

The gliding forces remained constant over 24 months at 5° C. in a range of 6.5-7.7 N (maximum) and 5.8-7.4 N (average), as well 3.9-5.0 N for break loose force. Over 36 months at 5° C. gliding forces remained constant in a range of 6.1-8.5 N (maximum) and 5.8-7.7 N (average), as well 3.9-5.0 N for break loose force. At 25° C. for up to 12 months storage time gliding forces range between 6.7-15.7 N (maximum) and 6.2-12.4 N (average), as well as 3.9-5.6 N for the break loose force. At 40° C. for up to 3 months storage time gliding forces range between 8.7-23.1 N (maximum) and 7.3-16.4 N (average), as well as 5.1-6.6 N for the break loose force.

The protein related particles and foreign particles remained essentially constantly low over the storage time at the different storage temperatures tested.

3.4. Summary of the Results

In summary, all tested formulations were stable, substantiating that the trehalose concentration can be varied while maintaining a high stability. Therefore, the indicated trehalose concentrations can be flexibly applied in order to produce stable protein formulations of 150 mg/mL risankizumab.

V. Example 4: Analysis of Further Parameters of a Specific Formulation

In view of the results of the prior examples, a particularly suitable formulation comprises the following compounds:

150 mg/mL risankizumab,
10 mM acetate buffer,
185 mM trehalose, and
0.2 mg/mL PS20;
wherein the formulation has a pH of 5.7.

The appearance of this formulation was clear to slightly opalescent and essentially free of foreign particles. The osmolality was about 310 mOsm/kg. The formulation is particularly suitable for injection, especially for subcutaneous injection. Moreover, a viscosity of about 9.6 mPas was measured, making it suitable for injection using a syringe. The conductivity at 20° C. was about 1.53 mS/cm, the density at 20° C. was about 1.067 g/cm³ and the density at 4° C. was about 1.071 g/cm³.

This 150 mg/ml risankizumab formulation may be provided as follows:

| Ingredient | Concentration [mmol/L] | Concentration [g/l] | Function | In an embodiment wherein this formulation is provided in a syringe (V = 1 ml) the Nominal Amount [mg/syringe] is as follows |
|---|---|---|---|---|
| Risankizumab | 1.00 | 150 | Drug substance | 150 |
| Sodium acetate trihydrate | 9.10 | 1.24 | Buffer | 1.24 |
| Acetic acid | 0.900 | 0.0540 | Buffer | 0.0540 |
| Trehalose dihydrate | 185 | 70.0 | Adjustment tonicity | 70.0 |
| Polysorbate 20 | 0.163 | 0.200 | Surfactant | 0.200 |

LIST OF ABBREVIATIONS

| Abbreviation | Full form |
|---|---|
| APG | Acidic peak group |
| AUC | Area under curve |
| BPG | Basic peak group |
| CGE | Capillary gel electrophoresis |
| FNU | Formazine nephelometric units |
| F/T | Freeze/thaw |
| HIC | Hydrophobic interaction chromatography |
| HMW | High molecular weight |
| HP-SEC | High pressure size exclusion chromatography |
| IEC | Ion exchange chromatography |
| IL-23 | Interleukin-23 |
| LMW | Low molecular weight |
| MFI | Micro flow imaging |
| mOsm/kg | Milliosmole/kilogram |
| mPas | Millipascal second |
| mS/cm | Millisiemens per centimeter |
| PS20 | Polysorbate 20 |
| RALS | Right-angle light scattering |
| r.h. | Relative humidity |
| rhIL-23 | Recombinant human interleukin-23 |
| SEC | Size exclusion chromatography |
| SPR | Surface plasmon resonance |
| STP | Sampling time point |
| SVP | Sub-visible particles |
| UF/DF | Ultrafiltration/Diafiltration |
| U/min | Revolutions per minute |
| UP-SEC | Ultra-performance size exclusion chromatography |
| WCX | Weak cation exchange chromatography |

The invention claimed is:

1. A stable liquid aqueous pharmaceutical formulation comprising a) 150 mg/ml of risankizumab;

b) 185 mM trehalose;

c) 0.2 mg/ml polysorbate 20; and d) 10 mM acetate buffer;

wherein the pH of the stable liquid aqueous pharmaceutical formulation is in the range of 5.5 to 5.9, and wherein the viscosity of the formulation is less than 20.0 mPas measured at 20° C. following storage of the formulation for 12 months at 5° C.

2. The stable liquid aqueous pharmaceutical formulation of claim 1, wherein the pH of the formulation is 5.5.

3. The stable liquid aqueous pharmaceutical formulation of claim 1, wherein the pH of the formulation is 5.7.

4. The stable liquid aqueous pharmaceutical formulation of claim 1, wherein the pH of the formulation is 5.9.

5. A stable liquid aqueous pharmaceutical formulation, comprising:

a) risankizumab at a concentration from 150 mg/ml to 192.3 mg/ml;

b) 185 mM trehalose;

c) 0.2 mg/ml polysorbate 20; and d) 10 mM acetate buffer, wherein the pH of the stable liquid aqueous pharmaceutical formulation is in the range of 5.5 to 5.9, and wherein the viscosity of the formulation is less than 20.0 mPas measured at 20° C.

6. The stable liquid aqueous pharmaceutical formulation of claim 5, wherein the pH of the formulation is 5.5.

7. The stable liquid aqueous pharmaceutical formulation of claim 5, wherein the pH of the formulation is 5.7.

8. The stable liquid aqueous pharmaceutical formulation of claim 5, wherein the pH of the formulation is 5.9.

* * * * *

SEQUENCE LISTING

```
<160> NUMBER OF SEQ ID NOS: 2

<210> SEQ ID NO 1
<211> LENGTH: 214
<212> TYPE: PRT
<213> ORGANISM: Artificial Sequence
<220> FEATURE:
```

```
<223> OTHER INFORMATION: Antibody light chain

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asp Val Ala Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Arg Thr Asp Phe Thr Leu Thr Ile Ser Ser Leu Gln Pro
65                  70                  75                  80

Glu Asp Val Ala Asp Tyr Phe Cys His Gln Tyr Ser Ser Tyr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 2
<211> LENGTH: 449
<212> TYPE: PRT
<213> ORGANISM: Artificial Sequence
<220> FEATURE:
<223> OTHER INFORMATION: Antibody heavy chain

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Gln
            20                  25                  30

Thr Ile His Trp Met Arg Gln Ala Pro Gly Gln Gly Leu Glu Trp Ile
        35                  40                  45

Gly Tyr Ile Tyr Pro Arg Asp Asp Ser Pro Lys Tyr Asn Glu Asn Phe
    50                  55                  60

Lys Gly Lys Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Pro Asp Arg Ser Gly Tyr Ala Trp Phe Ile Tyr Trp Gly Gln
            100                 105                 110

Gly Thr Leu Val Thr Val Ser Ser Ala Ser Thr Lys Gly Pro Ser Val
            115                 120                 125
```

-continued

```
Phe Pro Leu Ala Pro Ser Ser Lys Ser Thr Ser Gly Gly Thr Ala Ala
    130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
        180             185             190

Ser Ser Ser Leu Gly Thr Gln Thr Tyr Ile Cys Asn Val Asn His Lys
        195             200             205

Pro Ser Asn Thr Lys Val Asp Lys Arg Val Glu Pro Lys Ser Cys Asp
    210             215             220

Lys Thr His Thr Cys Pro Pro Cys Pro Ala Pro Glu Ala Ala Gly Gly
225             230             235             240

Pro Ser Val Phe Leu Phe Pro Pro Lys Pro Lys Asp Thr Leu Met Ile
            245             250             255

Ser Arg Thr Pro Glu Val Thr Cys Val Val Val Asp Val Ser His Glu
            260             265             270

Asp Pro Glu Val Lys Phe Asn Trp Tyr Val Asp Gly Val Glu Val His
        275             280             285

Asn Ala Lys Thr Lys Pro Arg Glu Glu Gln Tyr Asn Ser Thr Tyr Arg
    290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
            325             330             335

Lys Thr Ile Ser Lys Ala Lys Gly Gln Pro Arg Glu Pro Gln Val Tyr
            340             345             350

Thr Leu Pro Pro Ser Arg Glu Glu Met Thr Lys Asn Gln Val Ser Leu
        355             360             365

Thr Cys Leu Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
        435             440             445

Gly
```